(12) United States Patent
Fowler et al.

(10) Patent No.: US 6,268,196 B1
(45) Date of Patent: *Jul. 31, 2001

(54) METHOD AND COMPOSITIONS FOR TREATING CELLULOSE CONTAINING FABRICS USING TRUNCATED CELLULASE ENZYME COMPOSITIONS

(75) Inventors: Timothy Fowler, San Carlos; Kathleen A. Clarkson; Michael Ward, both of San Francisco; Katherine D. Collier, Redwood City; Edmund Larenas, Moss Beach, all of CA (US)

(73) Assignee: Genencor International, Inc., Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/382,452

(22) Filed: Feb. 1, 1995

Related U.S. Application Data

(63) Continuation-in-part of application No. 08/169,948, filed on Dec. 17, 1993.

(51) Int. Cl.$^7$ .............................. C12N 9/42; C12S 11/00
(52) U.S. Cl. ..................... 435/209; 435/263; 435/264; 2/1
(58) Field of Search .................................. 435/209, 263, 435/264; 2/1

(56) References Cited

FOREIGN PATENT DOCUMENTS

| | | |
|---|---|---|
| 0 307 564 | 3/1989 | (EP) . |
| WO 90/09436 | 8/1990 | (WO) . |
| WO 91/04673 | 4/1991 | (WO) . |
| WO 91/10732 | 7/1991 | (WO) . |
| WO 91/18090 | 11/1991 | (WO) . |
| WO 92/06165 | 4/1992 | (WO) . |
| WO 92/06184 | 4/1992 | (WO) . |
| WO 92/06209 | 4/1992 | (WO) . |
| WO 93/20714 | 10/1993 | (WO) . |
| WO 94/07998 | 4/1994 | (WO) . |
| WO 95/02675 | 1/1995 | (WO) . |
| WO 95/16782 | 6/1995 | (WO) . |

OTHER PUBLICATIONS

Ong, E., et al. (1989) Tibtech 7, 239–243.*

Penttila, M, et al. (1986) Gene 45, 253–263.*

Aho, S. (1991) FEBS Lett. 291 (1), 45–49.*

*Aho, et al. "Structural and functional analysis of *Trichoderma reesei* endoglucanase I expressed in yeast *Saccaromyces cerevisiae*", *FEBS Letters* 291(1):45–49 (1991).

*Ong et al., "The cellulose–binding domains of cellulases: tools for biotechnology" *Trends Biotechnol* 7(9):239–243 (1989).

Bedford, M., "Feed Enzymes in Barley–Based Diets" *J. or the Science of Food and Agriculture* 63(1):107–108 (1993).

R. Michael Tyndall, "Improving the Softness and Surface Appearance of Cotton Fabrics and Garments by Treatment with Cellulase Enzymes," *Textile Chemist and Colorist*, (24):Jun. 23–26, 1996.

* cited by examiner

*Primary Examiner*—Charles L. Patterson, Jr.
(74) *Attorney, Agent, or Firm*—Lynn Marcus-Werner; Genecor International, Inc.

(57) ABSTRACT

Improved methods of treating cellulose containing fabrics with cellulase comprising contacting the cellulose fabrics with truncated cellulase enzyme. Treatment of cellulose containing fabrics with cellulase core domains of the invention are disclosed as offering specific advantages of reduced redeposition of dye and increased abrasion.

48 Claims, 24 Drawing Sheets

```
AAGCTTAGCCAAGAACAATAGCCGATAAAGATAGCCTCATTAAACGGAAT
                                                   50
GAGCTAGTAGGCAAAGTCAGCGAATGTGTATATATAAAGGTTCGAGGTCC
                                                   100
GTGCCTCCCTCATGCTCTCCCCATCTACTCATCAACTCAGATCCTCCAGG
                                                   150
AGACTTGTACACCATNTTTTGAGGCACAGAAACCCAATAGTCAACCGCGG
                                                   200
ACTGGCATCATGTATCGGAAGTTGGCCGTCATCTCGGCCTTCTTGGCCAC
                                                   250
            Met Tyr Arg Lys Leu Ala Val Ile Ser Ala Phe Leu Ala Thr
AGCTCGTGCTCAGTCGGCCTGCACTCTCCAATCGGAGACTCACCCGCCTC
                                                   300
 Ala Arg Ala Gln Ser Ala Cys Thr Leu Gln Ser Glu Thr His Pro Pro
TGACATGGCAGAAATGCTCGTCTGGTGGCACTTGCACTCAACAGACAGGC
                                                   350
Leu Thr Trp Gln Lys Cys Ser Ser Gly Gly Thr Cys Thr Gln Gln Thr Gly
TCCGTGGTCATCGACGCCAACTGGCGCTGGACTCACGCTACGAACAGCAG
                                                   400
 Ser Val Val Ile Asp Ala Asn Trp Arg Trp Thr His Ala Thr Asn Ser Ser
CACGAACTGCTACGATGGCAACACTTGGAGCTCGACCCTATGTCCTGACA
                                                   450
     Thr Asn Cys Tyr Asp Gly Asn Thr Trp Ser Ser Thr Leu Cys Pro Asp
ACGAGACCTGCGCGAAGAACTGCTGTCTGGACGGTGCCGCCTACGCGTCC
                                                   500
Asn Glu Thr Cys Ala Lys Asn Cys Cys Leu Asp Gly Ala Ala Tyr Ala Ser
ACGTACGGAGTTACCACGAGCGGTAACAGCCTCTCCATTGGCTTTGTCAC
                                                   550
 Thr Tyr Gly Val Thr Thr Ser Gly Asn Ser Leu Ser Ile Gly Phe Val Thr
CCAGTCTGCGCAGAAGAACGTTGGCGCTCGCCTTTACCTTATGGCGAGCG
                                                   600
   Gln Ser Ala Gln Lys Asn Val Gly Ala Arg Leu Tyr Leu Met Ala Ser
ACACGACCTACCAGGAATTCACCCTGCTTGGCAACGAGTTCTCTTTCGAT
                                                   650
Asp Thr Thr Tyr Gln Glu Phe Thr Leu Leu Gly Asn Glu Phe Ser Phe Asp
GTTGATGTTTCGCAGCTGCCGTAAGTGACTTACCATGAACCCCTGACGTA
                                                   700
 Val Asp Val Ser Gln Leu Pro
TCTTCTTGTGGGCTCCCAGCTGACTGGCCAATTTAAGGTGCGGCTTGAAC
                                                   750
                                     Cys Gly Leu Asn
GGAGCTCTCTACTTCGTGTCCATGGACGCGGATGGTGGCGTGAGCAAGTA
                                                   800
 Gly Ala Leu Tyr Phe Val Ser Met Asp Ala Asp Gly Gly Val Ser Lys Tyr
```

FIG._1A

```
                TCCCACCAACACCGCTGGCGCCAAGTACGGCACGGGGTACTGTGACAGCC
                                                                    850
        Pro Thr Asn Thr Ala Gly Ala Lys Tyr Gly Thr Gly Tyr Cys Asp Ser
                AGTGTCCCCGCGATCTGAAGTTCATCAATGGCCAGGCCAACGTTGAGGGC
                                                                    900
        Gln Cys Pro Arg Asp Leu Lys Phe Ile Asn Gly Gln Ala Asn Val Glu Gly
                TGGGAGCCGTCATCCAACAACGCAAACACGGGCATTGGAGGACACGGAAG
                                                                    950
        Trp Glu Pro Ser Ser Asn Asn Ala Asn Thr Gly Ile Gly Gly His Gly Ser
                CTGCTGCTCTGAGATGGATATCTGGGAGGCCAACTCCATCTCCGAGGCTC
                                                                    1000
        Cys Cys Ser Glu Met Asp Ile Trp Glu Ala Asn Ser Ile Ser Glu Ala
                TTACCCCCCACCCTTGCACGACTGTCGGCCAGGAGATCTGCGAGGGTGAT
                                                                    1050
Leu Thr Pro His Pro Cys Thr Thr Val Gly Gln Glu Ile Cys Glu Gly Asp
                GGGTGCGGCGGAACTTACTCGATAACAGATATGGCGGCACTTGCGATCC
                                                                    1100
        Gly Cys Gly Gly Thr Tyr Ser Asp Asn Arg Tyr Gly Gly Thr Cys Asp Pro
                CGATGGCTGCGACTGGAACCCATACCGCCTGGGCAACACCAGCTTCTACG
                                                                    1150
        Asp Gly Cys Asp Trp Asn Pro Tyr Arg Leu Gly Asn Thr Ser Phe Tyr
                GCCCTGGCTCAAGCTTTACCCTCGATACCACCAAGAAATTGACCGTTGTC
                                                                    1200
Gly Pro Gly Ser Ser Phe Thr Leu Asp Thr Thr Lys Lys Leu Thr Val Val
                ACCCAGTTCGAGACGTCGGGTGCCATCAACCGATACTATGTCCAGAATGG
                                                                    1250
        Thr Gln Phe Glu Thr Ser Gly Ala Ile Asn Arg Tyr Tyr Val Gln Asn Gly
                CGTCACTTTCCAGCAGCCCAACGCCGAGCTTGGTAGTTACTCTGGCAACG
                                                                    1300
        Val Thr Phe Gln Gln Pro Asn Ala Glu Leu Gly Ser Tyr Ser Gly Asn
                AGCTCAACGATGATTACTGCACAGCTGAGGAGGCAGAATTCGGCGGATCC
                                                                    1350
        Glu Leu Asn Asp Asp Tyr Cys Thr Ala Glu Glu Ala Glu Phe Gly Gly Ser
                TCTTTCTCAGACAAGGGCGGCCTGACTCAGTTCAAGAAGGCTACCTCTGG
                                                                    1400
        Ser Phe Ser Asp Lys Gly Gly Leu Thr Gln Phe Lys Lys Ala Thr Ser Gly
                CGGCATGGTTCTGGTCATGAGTCTGTGGGATGATGTGAGTTTGATGGACA
                                                                    1450
        Gly Met Val Leu Val Met Ser Leu Trp Asp Asp
                AACATGCGCGTTGACAAAGAGTCAAGCAGCTGACTGAGATGTTACAGTAC
                                                                    1500
                                                                    Tyr
                TACGCCAACATGCTGTGGCTGGACTCCACCTACCCGACAAACGAGACCTC
                                                                    1550
        Tyr Ala Asn Met Leu Trp Leu Asp Ser Thr Tyr Pro Thr Asn Glu Thr Ser
```

FIG._1B

```
CTCCACACCCGGTGCCGTGCGCGGAAGCTGCTCCACCAGCTCCGGTGTCC
                                                    1600
 Ser Thr Pro Gly Ala Val Arg Gly Ser Cys Ser Thr Ser Ser Gly Val
CTGCTCAGGTCGAATCTCAGTCTCCCAACGCCAAGGTCACCTTCTCCAAC
                                                    1650
 Pro Ala Gln Val Glu Ser Gln Ser Pro Asn Ala Lys Val Thr Phe Ser Asn
ATCAAGTTCGGACCCATTGGCAGCACCGGCAACCCTAGCGGCGGCAACCC
                                                    1700
  Ile Lys Phe Gly Pro Ile Gly Ser Thr Gly Asn Pro Ser Gly Gly Asn Pro
TCCCGGCGGAAACCGTGGCACCACCACCACCCGCCGCCCAGCCACTACCA
                                                    1750
  Pro Gly Gly Asn Arg Gly Thr Thr Thr Thr Arg Arg Pro Ala Thr Thr
CTGGAAGCTCTCCCGGACCTACCCAGTCTCACTACGGCCAGTGCGGCGGT
                                                    1800
Thr Gly Ser Ser Pro Gly Pro Thr Gln Ser His Tyr Gly Gln Cys Gly Gly
ATTGGCTACAGCGGCCCCACGGTCTGCGCCAGCGGCACAACTTGCCAGGT
                                                    1850
 Ile Gly Tyr Ser Gly Pro Thr Val Cys Ala Ser Gly Thr Thr Cys Gln Val
CCTGAACCCTTACTACTCTCAGTGCCTGTAAAGCTCCGTGCGAAAGCCTG
                                                    1900
 Leu Asn Pro Tyr Tyr Ser Gln Cys Leu  •
ACGCACCGGTAGATTCTTGGTGAGCCCGTATCATGACGGCGGCGGGAGCT
                                                    1950
ACATGGCCCCGGGTGATTTATTTTTTTTGTATCTACTTCTGACCCTTTTC
                                                    2000
AAATATACGGTCAACTCATCTTTCACTGGAGATGCGGCCTGCTTGGTATT
                                                    2050
GCGATGTTGTCAGCTTGGCAAATTGTGGCTTTCGAAAACACAAAACGATT
                                                    2100
CCTTAGTAGCCATGCATTTTAAGATAACGGAATAGAAGAAAGAGGAAATT
                                                    2150
AAAAAAAAAAAAAAAAACAAACATCCCGTTCATAACCCGTAGAATCGCCGC
                                                    2200
TCTTCGTGTATCCCAGTACCA
                    → 2221
```

```
GAATTCTAGGCTAGGTATGCGAGGCACGCGGATCTAGGGCAGACTGGGCA
                                                    50
TTGCATAGCTATGGTGTAGTAGAACTCCCGTCAACGGCTATTCTCACCTA
                                                    100
GACTTTCCCCTTCGAACTGACAAGTTGTTATATTGCCTGTGTACCAAGCG
                                                    150
CTAATGTGGACAGGATTAATGCCAGAGTTCATTAGCCTCAAGTAGAGCCT
                                                    200
ATTTCCTCGCCGGAAAGTCATCTCTCTTATTGCATTTCTGCCTTCCACTA
                                                    250
ACTCAGGGTGCAGCGCAACACTACACGCAACATATCACATTTATTAGCCG
                                                    300
TGCAACAAGGCTATTCTACGAAAAATGCTACACTCCACATGTTAAAGGCG
                                                    350
CATTCAACCAGCTTCTTTATTGGGTAATATACAGCCAGGCGGGGATGAAG
                                                    400
CTCATTAGCCGCCACTCAAGGCTATACAATGTTGCCAACTCTCCGGGCTT
                                                    450
TATCCTGTGCTCCCGAATACCACATCGTGATGATGCTTCAGCGCACGGAA
                                                    500
GTCACAGACACCGCCTGTATAAAAGGGGGACTGTGACCCTGTATGAGGCG
                                                    550
CAACATGGTCTCACAGCAGCTCACCTGAAGAGGCTTGTAAGATCACCCTC
                                                    600
TGTGTATTGCACCATGATTGTCGGCATTCTCACCACGCTGGCTACGCTGG
                                                    650
            Met Ile Val Gly Ile Leu Thr Thr Leu Ala Thr Leu
CCACACTCGCAGCTAGTGTGCCTCTAGAGGAGCGGCAAGCTTGCTCAAGC
                                                    700
Ala Thr Leu Ala Ala Ser Val Pro Leu Glu Glu Arg Gln Ala Cys Ser Ser
GTCTGGTAATTATGTGAACCCTCTCAAGAGACCCAAATACTGAGATATGT
                                                    750
Val Trp
CAAGGGGCCAATGTGGTGGCCAGAATTGGTCGGGTCCGACTTGCTGTGCT
                                                    800
        Gly Gln Cys Gly Gly Gln Asn Trp Ser Gly Pro Thr Cys Cys Ala
TCCGGAAGCACATGCGTCTACTCCAACGACTATTACTCCCAGTGTCTTCC
                                                    850
Ser Gly Ser Thr Cys Val Tyr Ser Asn Asp Tyr Tyr Ser Gln Cys Leu Pro
CGGCGCTGCAAGCTCAAGCTCGTCCACGCGCGCCGCGTCGACGACTTCTC
                                                    900
Gly Ala Ala Ser Ser Ser Ser Ser Thr Arg Ala Ala Ser Thr Thr Ser
GAGTATCCCCCACAACATCCCGGTCGAGCTCCGCGACGCCTCCACCTGGT
                                                    950
Arg Val Ser Pro Thr Thr Ser Arg Ser Ser Ser Ala Thr Pro Pro Pro Gly
```

FIG._2A

```
                TCTACTACTACCAGAGTACCTCCAGTCGGATCGGGAACCGCTACGTATTC
                                                                              1000
  Ser Thr Thr Thr Arg Val Pro Pro Val Gly Ser Gly Thr Ala Thr Tyr Ser
                AGGCAACCCTTTTGTTGGGGTCACTCCTTGGGCCAATGCATATTACGCCT
                                                                              1050
    Gly Asn Pro Phe Val Gly Val Thr Pro Trp Ala Asn Ala Tyr Tyr Ala
                CTGAAGTTAGCAGCCTCGCTATTCCTAGCTTGACTGGAGCCATGGCCACT
                                                                              1100
  Ser Glu Val Ser Ser Leu Ala Ile Pro Ser Leu Thr Gly Ala Met Ala Thr
                GCTGCAGCAGCTGTCGCAAAGGTTCCCTCTTTTATGTGGCTGTAGGTCCT
                                                                              1150
    Ala Ala Ala Ala Val Ala Lys Val Pro Ser Phe Met Trp Leu
                CCCGGAACCAAGGCAATCTGTTACTGAAGGCTCATCATTCACTGCAGAGA
                                                                              1200
                                                                      Asp
                TACTCTTGACAAGACCCCTCTCATGGAGCAAACCTTGGCCGACATCCGCA
                                                                              1250
    Thr Leu Asp Lys Thr Pro Leu Met Glu Gln Thr Leu Ala Asp Ile Arg
                CCGCCAACAAGAATGGCGGTAACTATGCCGGACAGTTTGTGGTGATAGAC
                                                                              1300
  Thr Ala Asn Lys Asn Gly Gly Asn Tyr Ala Gly Gln Phe Val Val Ile Asp
                TTGCCGGATCGCGATTGCGCTGCCCTTGCCTCGAATGGCGAATACTCTAT
                                                                              1350
    Leu Pro Asp Arg Asp Cys Ala Ala Leu Ala Ser Asn Gly Glu Tyr Ser Ile
                TGCCGATGGTGGCGTCGCCAAATATAAGAACTATATCGACACCATTCGTC
                                                                              1400
    Ala Asp Gly Gly Val Ala Lys Tyr Lys Asn Tyr Ile Asp Thr Ile Arg
                AAATTGTCGTGGAATATTCCGATATCCGGACCCTCCTGGTTATTGGTATG
                                                                              1450
  Gln Ile Val Val Glu Tyr Ser Asp Ile Arg Thr Leu Leu Val Ile
                AGTTTAAACACCTGCCTCCCCCCCCCCTTCCCTTCCTTTCCCGCCGGCAT
                                                                              1500
                CTTGTCGTTGTGCTAACTATTGTTCCCTCTTCCAGAGCCTGACTCTCTTG
                                                                              1550
                                                      Glu Pro Asp Ser Leu
                CCAACCTGGTGACCAACCTCGGTACTCCAAAGTGTGCCAATGCTCAGTCA
                                                                              1600
  Ala Asn Leu Val Thr Asn Leu Gly Thr Pro Lys Cys Ala Asn Ala Gln Ser
                GCCTACCTTGAGTGCATCAACTACGCCGTCACACAGCTGAACCTTCCAAA
                                                                              1650
    Ala Tyr Leu Glu Cys Ile Asn Tyr Ala Val Thr Gln Leu Asn Leu Pro Asn
                TGTTGCGATGTATTTGGACGCTGGCCATGCAGGATGGCTTGGCTGGCCGG
                                                                              1700
    Val Ala Met Tyr Leu Asp Ala Gly His Ala Gly Trp Leu Gly Trp Pro
```

FIG._2B

```
                  CAAACCAAGACCCGGCCGCTCAGCTATTTGCAAATGTTTACAAGAATGCA
                  |----|----|----|----|----|----|----|----|----|----| 1750
     Ala Asn Gln Asp Pro Ala Ala Gln Leu Phe Ala Asn Val Tyr Lys Asn Ala
                  TCGTCTCCGAGAGCTCTTCGCGGATTGGCAACCAATGTCGCCAACTACAA
                  |----|----|----|----|----|----|----|----|----|----| 1800
     Ser Ser Pro Arg Ala Leu Arg Gly Leu Ala Thr Asn Val Ala Asn Tyr Asn
                  CGGGTGGAACATTACCAGCCCCCATCGTACACGCAAGGCAACGCTGTCT
                  |----|----|----|----|----|----|----|----|----|----| 1850
       Gly Trp Asn Ile Thr Ser Pro Pro Ser Tyr Thr Gln Gly Asn Ala Val
                  ACAACGAGAAGCTGTACATCCACGCTATTGGACCTCTTCTTGCCAATCAC
                  |----|----|----|----|----|----|----|----|----|----| 1900
     Tyr Asn Glu Lys Leu Tyr Ile His Ala Ile Gly Pro Leu Leu Ala Asn His
                  GGCTGGTCCAACGCCTTCTTCATCACTGATCAAGGTCGATCGGGAAAGCA
                  |----|----|----|----|----|----|----|----|----|----| 1950
     Gly Trp Ser Asn Ala Phe Phe Ile Thr Asp Gln Gly Arg Ser Gly Lys Gln
                  GCCTACCGGACAGCAACAGTGGGGAGACTGGTGCAATGTGATCGGCACCG
                  |----|----|----|----|----|----|----|----|----|----| 2000
       Pro Thr Gly Gln Gln Gln Trp Gly Asp Trp Cys Asn Val Ile Gly Thr
                  GATTTGGTATTCGCCCATCCGCAAACACTGGGGACTCGTTGCTGGATTCG
                  |----|----|----|----|----|----|----|----|----|----| 2050
     Gly Phe Gly Ile Arg Pro Ser Ala Asn Thr Gly Asp Ser Leu Leu Asp Ser
                  TTTGTCTGGGTCAAGCCAGGCGGCGAGTGTGACGGCACCAGCGACAGCAG
                  |----|----|----|----|----|----|----|----|----|----| 2100
     Phe Val Trp Val Lys Pro Gly Gly Glu Cys Asp Gly Thr Ser Asp Ser Ser
                  TGCGCCACGATTTGACTCCCACTGTGCGCTCCAGATGCCTTGCAACCGG
                  |----|----|----|----|----|----|----|----|----|----| 2150
       Ala Pro Arg Phe Asp Ser His Cys Ala Leu Pro Asp Ala Leu Gln Pro
                  CGCCTCAAGCTGGTGCTTGGTTCCAAGCCTACTTTGTGCAGCTTCTCACA
                  |----|----|----|----|----|----|----|----|----|----| 2200
     Ala Pro Gln Ala Gly Ala Trp Phe Gln Ala Tyr Phe Val Gln Leu Leu Thr
                  AACGCAAACCCATCGTTCCTGTAAGGCTTTCGTGACCGGGCTTCAAACAA
                  |----|----|----|----|----|----|----|----|----|----| 2250
     Asn Ala Asn Pro Ser Phe Leu •
                  TGATGTGCGATGGTGTGGTTCCCGGTTGGCGGAGTCTTTGTCTACTTTGG
                  |----|----|----|----|----|----|----|----|----|----| 2300
                  TTGTCTGTCGCAGGTCGGTAGACCGCAAATGAGCAACTGATGGATTGTTG
                  |----|----|----|----|----|----|----|----|----|----| 2350
                  CCAGCGATACTATAATTCACATGGATGGTCTTTGCGATCAGTAGCTAGTG
                  |----|----|----|----|----|----|----|----|----|----| 2400
                  AGAGAGAGAGAACATCTATCCACAATGTCGAGTGTCTATTAGACATACTC
                  |----|----|----|----|----|----|----|----|----|----| 2450
                  CGAGAATAAAGTCAACTGTGTCTGTGATCTAAAGATCGATTCGGCAGTCG
                  |----|----|----|----|----|----|----|----|----|----| 2500
                  AGTAGCGTATAACAACTCCGAGTACCAGCAAAAGCACGTCGTGACAGGAG
                  |----|----|----|----|----|----|----|----|----|----| 2550
                  CAGGCTTTGCCAACTGCGCAACCTTGCTTGAATGAGGATACACGGGGTGC
                  |----|----|----|----|----|----|----|----|----|----| 2600
```

FIG._2C

```
AACATGGCTGTACTGATCCATCGCAACCAAAATTTCTGTTTATAGATCAA
                                                  2650
GCTGGTAGATTCCAATTACTCCACCTCTTGCGCTTCTCCATGACATGTAA
                                                  2700
GTGCACGTAGGAAACCATACCCAAATTGCCTACAGCTGCGGAGCATGAGC
                                                  2750
CTATGGCGATCAGTCTGGTCATGTTAACCAGCCTGTGCTCTGACGTTAAT
                                                  2800
GCAGAATAGAAAGCCGCGGTTGCAATGCAAATGATGATGCCTTTGCAGAA
                                                  2850
ATGGCTTGCTCGCTGACTGATACCAGTAACAACTTTGCTTGGCCGTCTAG
                                                  2900
CGCTGTTGATTGTATTCATCACAACCTCGTCTCCCTCCTTTGGGTTGAGC
                                                  2950
TCTTTGGATGGCTTTCCAAACGTTAATAGCGCGTTTTTCTCCACAAAGTA
                                                  3000
TTCGTATGGACGCGCTTTTGGCTGTATTGCGTGAGCTACCAGCAGCCCAA
                                                  3050
TTGGCGAAGTCTTGAGCCGCACTCGCATAGAATAATTGATTGCGCATTTG
                                                  3100
ATGCGATTTTGAGCGGCTGTTTCAGGCGACATTTCGCCGCCTTTATTTG
                                                  3150
CTCCATTATATCATCGATGGCATGTCCAATAGCCCGGTGATAGTCTTGTC
                                                  3200
GAATATGGCTGTCGTGGATAACCCATCGGCAGCAGATGATAATGATTCCG
                                                  3250
CAGCACAAGCTCGTATGTGGGTAGCAGAAGAACTGAGCGAGATCTTCGAG
                                                  3300
GGCGTAACTCTGCATATCCGATTGGCCTGCTGCCACATGTCATTTTGCTT
                                                  3350
CGGTTTCTTTTCTGTTGAGTTCTTGTATTTGGGTGAAAGTAACATGGTGT
                                                  3400
ATGACGAGAGACATTGGTGGTAAGAAAAAATTTCACCTCCTCTTAGTGCA
                                                  3450
GGACTGACTCTCAAAATCTATATGCAAATGTGTCGTGTAACACCCTTCGC
                                                  3500
ATGAGCGCTGACCGTACCCTACCATTTCGCCCCACTCATGATAGCAGAAG
                                                  3550
AGACATATTAATTCGGCAATGCTACGAAAGTCTGCAGGCTATGCTTAAAT
                                                  3600
AAACGCTTGCCACAGAAGCCGACAGTTTATTGTTACTACTTACTATACTG
                                                  3650
TATTATTGTTGCTCACATAAGGCGGTGAACCATTGGTTCACACGACGCCT
                                                  3700
GACGAGGTAAATTACTCTCTCGTAGGGCTGCCAAGGTAGGTCCCAACCCC
                                                  3750
GTATCCTCGGTCGAGGGTGCGAGGTTCTTTGGTCCTTCCCTCTTTGGTAA
                                                  3800
```

FIG._2D

```
AGCCCAGTAGCGTGTTTGAATCAGTTCACAATCTCTCCTAAACACAGTCC
|----|----|----|----|----|----|----|----|----|----| 3850
GACACTAGGTAGGTACGTTGTAATAGCAACTCAAACATGTAATTCGTTTC
|----|----|----|----|----|----|----|----|----|----| 3900
AAGGCAGGAACATTTTATAAACTTCCCTGCGATTTAATCAATAAAGATCC
|----|----|----|----|----|----|----|----|----|----| 3950
TAGTCCAATCGTATACTACCTACCTAGCTAAGGTAGGTAGGTAGTTCGTG
|----|----|----|----|----|----|----|----|----|----| 4000
GGAACCTGGTCGCTAATTCACGCAACCCACTTTGCGCTCTTCGCCTGGCC
|----|----|----|----|----|----|----|----|----|----| 4050
GTCGTTGAAGGTAAAGCAGTTGTACCCATCACCTAACTCAACCGACACCG
|----|----|----|----|----|----|----|----|----|----| 4100
TTGATCTGCTCAAGGCAGTTTTC
|----|----|----|--→ 4123
```

```
TGTGTTGAAATCCAACTTATAAAGACAACAACCGCAAACTTTGTCTTGTG
                                                    50
CCATCAGATTGTTGCCAAGCACCGTCCCCCCCCCTATCTTAGTCCTTCT
                                                    100
TGTTGTCCCAAAATGGCGCCCTCAGTTACACTGCCGTTGACCACGGCCAT
                                                    150
           Met Ala Pro Ser Val Thr Leu Pro Leu Thr Thr Ala Ile
CCTGGCCATTGCCCGGCTCGTCGCCGCCCAGCAACCGGGTACCAGCACCC
                                                    200
 Leu Ala Ile Ala Arg Leu Val Ala Ala Gln Gln Pro Gly Thr Ser Thr
CCGAGGTCCATCCCAAGTTGACAACCTACAAGTGTACAAAGTCCGGGGGG
                                                    250
Pro Glu Val His Pro Lys Leu Thr Thr Tyr Lys Cys Thr Lys Ser Gly Gly
   TGCGTGGCCCAGGACACCTCGGTGGTCCTTGACTGGAACTACCGCTGGAT
                                                    300
  Cys Val Ala Gln Asp Thr Ser Val Val Leu Asp Trp Asn Tyr Arg Trp Met
GCACGACGCAAACTACAACTCGTGCACCGTCAACGGCGGCGTCAACACCA
                                                    350
    His Asp Ala Asn Tyr Asn Ser Cys Thr Val Asn Gly Gly Val Asn Thr
CGCTCTGCCCTGACGAGGCGACCTGTGGCAAGAACTGCTTCATCGAGGGC
                                                    400
Thr Leu Cys Pro Asp Glu Ala Thr Cys Gly Lys Asn Cys Phe Ile Glu Gly
   GTCGACTACGCCGCCTCGGGCGTCACGACCTCGGGCAGCAGCCTCACCAT
                                                    450
 Val Asp Tyr Ala Ala Ser Gly Val Thr Thr Ser Gly Ser Ser Leu Thr Met
GAACCAGTACATGCCCAGCAGCTCTGGCGGCTACAGCAGCGTCTCTCCTC
                                                    500
    Asn Gln Tyr Met Pro Ser Ser Ser Gly Gly Tyr Ser Ser Val Ser Pro
GGCTGTATCTCCTGGACTCTGACGGTGAGTACGTGATGCTGAAGCTCAAC
                                                    550
Arg Leu Tyr Leu Leu Asp Ser Asp Gly Glu Tyr Val Met Leu Lys Leu Asn
   GGCCAGGAGCTGAGCTTCGACGTCGACCTCTCTGCTCTGCCGTGTGGAGA
                                                    600
 Gly Gln Glu Leu Ser Phe Asp Val Asp Leu Ser Ala Leu Pro Cys Gly Glu
GAACGGCTCGCTCTACCTGTCTCAGATGGACGAGAACGGGGGCGCCAACC
                                                    650
   Asn Gly Ser Leu Tyr Leu Ser Gln Met Asp Glu Asn Gly Gly Ala Asn
AGTATAACACGGCCGGTGCCAACTACGGGAGCGGCTACTGCGATGCTCAG
                                                    700
 Gln Tyr Asn Thr Ala Gly Ala Asn Tyr Gly Ser Gly Tyr Cys Asp Ala Gln
TGCCCCGTCCAGACATGGAGGAACGGCACCCTCAACACTAGCCACCAGGG
                                                    750
  Cys Pro Val Gln Thr Trp Arg Asn Gly Thr Leu Asn Thr Ser His Gln Gly
CTTCTGCTGCAACGAGATGGATATCCTGGAGGGCAACTCGAGGGCGAATG
                                                    800
     Phe Cys Cys Asn Glu Met Asp Ile Leu Glu Gly Asn Ser Arg Ala Asn
```

FIG._3A

```
CCTTGACCCCTCACTCTTGCACGGCCACGGCCTGCGACTCTGCCGGTTGC
                                                    850
Ala Leu Thr Pro His Ser Cys Thr Ala Thr Ala Cys Asp Ser Ala Gly Cys
GGCTTCAACCCCTATGGCAGCGGCTACAAAAGGTGAGCCTGATGCCACTA
                                                    900
Gly Phe Asn Pro Tyr Gly Ser Gly Tyr Lys Ser
CTACCCCTTTCCTGGCGCTCTCGCGGTTTTCCATGCTGACATGGTTTTCC
                                                    950

AGCTACTACGGCCCCGGAGATACCGTTGACACCTCCAAGACCTTCACCAT
                                                    1000
  Tyr Tyr Gly Pro Gly Asp Thr Val Asp Thr Ser Lys Thr Phe Thr Ile
CATCACCCAGTTCAACACGGACAACGGCTCGCCCTCGGGCAACCTTGTGA
                                                    1050
Ile Thr Gln Phe Asn Thr Asp Asn Gly Ser Pro Ser Gly Asn Leu Val
GCATCACCCGCAAGTACCAGCAAAACGGCGTCGACATCCCCAGCGCCCAG
                                                    1100
Ser Ile Thr Arg Lys Tyr Gln Gln Asn Gly Val Asp Ile Pro Ser Ala Gln
CCCGGCGGCGACACCATCTCGTCCTGCCCGTCCGCCTCAGCCTACGGCGG
                                                    1150
Pro Gly Gly Asp Thr Ile Ser Ser Cys Pro Ser Ala Ser Ala Tyr Gly Gly
CCTCGCCACCATGGGCAAGGCCCTGAGCAGCGGCATGGTGCTCGTGTTCA
                                                    1200
Leu Ala Thr Met Gly Lys Ala Leu Ser Ser Gly Met Val Leu Val Phe
GCATTTGGAACGACAACAGCCAGTACATGAACTGGCTCGACAGCGGCAAC
                                                    1250
Ser Ile Trp Asn Asp Asn Ser Gln Tyr Met Asn Trp Leu Asp Ser Gly Asn
GCCGGCCCCTGCAGCAGCACCGAGGGCAACCCATCCAACATCCTGGCCAA
                                                    1300
Ala Gly Pro Cys Ser Ser Thr Glu Gly Asn Pro Ser Asn Ile Leu Ala Asn
CAACCCCAACACGCACGTCGTCTTCTCCAACATCCGCTGGGGAGACATTG
                                                    1350
Asn Pro Asn Thr His Val Val Phe Ser Asn Ile Arg Trp Gly Asp Ile
GGTCTACTACGAACTCGACTGCGCCCCGCCCCCGCCTGCGTCCAGCACG
                                                    1400
Gly Ser Thr Thr Asn Ser Thr Ala Pro Pro Pro Pro Ala Ser Ser Thr
ACGTTTTCGACTACACCGAGGAGCTCGACGACTTCGAGCAGCCCGAGCTG
                                                    1450
Thr Phe Ser Thr Thr Pro Arg Ser Ser Thr Thr Ser Ser Ser Pro Ser Cys
CACGCAGACTCACTGGGGGCAGTGCGGTGGCATTGGGTACAGCGGGTGCA
                                                    1500
Thr Gln Thr His Trp Gly Gln Cys Gly Gly Ile Gly Tyr Ser Gly Cys
AGACGTGCACGTCGGGCACTACGTGCCAGTATAGCAACGACTGTTCGTAT
                                                    1550
Lys Thr Cys Thr Ser Gly Thr Thr Cys Gln Tyr Ser Asn Asp
```

FIG._3B

```
CCCCATGCCTGACGGGAGTGATTTTGAGATGCTAACCGCTAAAATACAGA
                                                  1600
                                              Tyr
CTACTCGCAATGCCTTTAGAGCGTTGACTTGCCTCTGGTCTGTCCAGACG
                                                  1650
Tyr Ser Gln Cys Leu •
GGGGCACGATAGAATGCGGGCACGCAGGGA
                             1680
```

```
TGCCATTTCTGACCTGGATAGGTTTTCCTATGGTCATTCCTATAAGAGAC
                                                   50
ACGCTCTTTCGTCGGCCCGTAGATATCAGATTGGTATTCAGTCGCACAGA
                                                   100
CGAAGGTGAGTTGATCCTCCAACATGAGTTCTATGAGCCCCCCCCTTGCC
                                                   150
CCCCCCCGTTCACCTTGACCTGCAATGAGAATCCCACCTTTTACAAGAGC
                                                   200
ATCAAGAAGTATTAATGGCGCTGAATAGCCTCTGCTCGATAATATCTCCC
                                                   250
CGTCATCGACAATGAACAAGTCCGTGGCTCCATTGCTGCTTGCAGCGTCC
                                                   300
```

Met Asn Lys Ser Val Ala Pro Leu Leu Leu Ala Ala Ser
```
ATACTATATGGCGGCGCCGTCGCACAGCAGACTGTCTGGGGCCAGTGTGG
                                                   350
```
Ile Leu Tyr Gly Gly Ala Val Ala Gln Gln Thr Val Trp Gly Gln Cys Gly
```
AGGTATTGGTTGGAGCGGACCTACGAATTGTGCTCCTGGCTCAGCTTGT
                                                   400
```
Gly Ile Gly Trp Ser Gly Pro Thr Asn Cys Ala Pro Gly Ser Ala Cys
```
CGACCCTCAATCCTTATTATGCGCAATGTATTCCGGGAGCCACTACTATC
                                                   450
```
Ser Thr Leu Asn Pro Tyr Tyr Ala Gln Cys Ile Pro Gly Ala Thr Thr Ile
```
ACCACTTCGACCCGGCCACCATCCGGTCCAACCACCACCACCAGGGCTAC
                                                   500
```
Thr Thr Ser Thr Arg Pro Pro Ser Gly Pro Thr Thr Thr Thr Arg Ala Thr
```
CTCAACAAGCTCATCAACTCCACCCACGAGCTCTGGGGTCCGATTTGCCG
                                                   550
```
Ser Thr Ser Ser Ser Thr Pro Pro Thr Ser Ser Gly Val Arg Phe Ala
```
GCGTTAACATCGCGGGTTTTGACTTTGGCTGTACCACAGAGTGAGTACCC
                                                   600
```
Gly Val Asn Ile Ala Gly Phe Asp Phe Gly Cys Thr Thr Asp
```
TTGTTTCCTGGTGTTGCTGGCTGGTTGGGCGGGTATACAGCGAAGCGGAC
                                                   650
GCAAGAACACCGCCGGTCCGCCACCATCAAGATGTGGGTGGTAAGCGGCG
                                                   700
GTGTTTTGTACAACTACCTGACAGCTCACTCAGGAAATGAGAATTAATGG
                                                   750
AAGTCTTGTTACAGTGGCACTTGCGTTACCTCGAAGGTTTATCCTCCGTT
                                                   800
```
                                  Gly Thr Cys Val Thr Ser Lys Val Tyr Pro Pro Leu
```
GAAGAACTTCACCGGCTCAAACAACTACCCCGATGGCATCGGCCAGATGC
                                                   850
```
Lys Asn Phe Thr Gly Ser Asn Asn Tyr Pro Asp Gly Ile Gly Gln Met

FIG._4A

```
                AGCACTTCGTCAACGAGGACGGGATGACTATTTTCCGCTTACCTGTCGGA
                                                                  900
    Gln His Phe Val Asn Glu Asp Gly Met Thr Ile Phe Arg Leu Pro Val Gly
                TGGCAGTACCTCGTCAACAACAATTTGGGCGGCAATCTTGATTCCACGAG
                                                                  950
    Trp Gln Tyr Leu Val Asn Asn Asn Leu Gly Gly Asn Leu Asp Ser Thr Ser
                CATTTCCAAGTATGATCAGCTTGTTCAGGGGTGCCTGTCTCTGGGCGCAT
                                                                  1000
        Ile Ser Lys Tyr Asp Gln Leu Val Gln Gly Cys Leu Ser Leu Gly Ala
                ACTGCATCGTCGACATCCACAATTATGCTCGATGGAACGGTGGGATCATT
                                                                  1050
    Tyr Cys Ile Val Asp Ile His Asn Tyr Ala Arg Trp Asn Gly Gly Ile Ile
                GGTCAGGGCGGCCCTACTAATGCTCAATTCACGAGCCTTTGGTCGCAGTT
                                                                  1100
    Gly Gln Gly Gly Pro Thr Asn Ala Gln Phe Thr Ser Leu Trp Ser Gln Leu
                GGCATCAAAGTACGCATCTCAGTCGAGGGTGTGGTTCGGCATCATGAATG
                                                                  1150
        Ala Ser Lys Tyr Ala Ser Gln Ser Arg Val Trp Phe Gly Ile Met Asn
                AGCCCCACGACGTGAACATCAACACCTGGGCTGCCACGGTCCAAGAGGTT
                                                                  1200
    Glu Pro His Asp Val Asn Ile Asn Thr Trp Ala Ala Thr Val Gln Glu Val
                GTAACCGCAATCCGCAACGCTGGTGCTACGTCGCAATTCATCTCTTTGCC
                                                                  1250
    Val Thr Ala Ile Arg Asn Ala Gly Ala Thr Ser Gln Phe Ile Ser Leu Pro
                TGGAAATGATTGGCAATCTGCTGGGGCTTTCATATCCGATGGCAGTGCAG
                                                                  1300
        Gly Asn Asp Trp Gln Ser Ala Gly Ala Phe Ile Ser Asp Gly Ser Ala
                CCGCCCTGTCTCAAGTCACGAACCCGGATGGGTCAACAACGAATCTGATT
                                                                  1350
    Ala Ala Leu Ser Gln Val Thr Asn Pro Asp Gly Ser Thr Thr Asn Leu Ile
                TTTGACGTGCACAAATACTTGGACTCAGACAACTCCGGTACTCACGCCGA
                                                                  1400
    Phe Asp Val His Lys Tyr Leu Asp Ser Asp Asn Ser Gly Thr His Ala Glu
                ATGTACTACAAATAACATTGACGGCGCCTTTTCTCCGCTTGCCACTTGGC
                                                                  1450
        Cys Thr Thr Asn Asn Ile Asp Gly Ala Phe Ser Pro Leu Ala Thr Trp
                TCCGACAGAACAATCGCCAGGCTATCCTGACAGAAACCGGTGGTGGCAAC
                                                                  1500
    Leu Arg Gln Asn Asn Arg Gln Ala Ile Leu Thr Glu Thr Gly Gly Gly Asn
                GTTCAGTCCTGCATACAAGACATGTGCCAGCAAATCCAATATCTCAACCA
                                                                  1550
        Val Gln Ser Cys Ile Gln Asp Met Cys Gln Gln Ile Gln Tyr Leu Asn Gln
                GAACTCAGATGTCTATCTTGGCTATGTTGGTTGGGGTGCCGGATCATTTG
                                                                  1600
    Asn Ser Asp Val Tyr Leu Gly Tyr Val Gly Trp Gly Ala Gly Ser Phe
```

FIG._4B

```
          ATAGCACGTATGTCCTGACGGAAACACCGACTAGCAGTGGTAACTCATGG
          └────┴────┴────┴────┴────┴────┴────┴────┴────┴────┘ 1650
          Asp Ser Thr Tyr Val Leu Thr Glu Thr Pro Thr Ser Ser Gly Asn Ser Trp
          ACGGACACATCCTTGGTCAGCTCGTGTCTCGCAAGAAAGTAGCACTCTGA
          └────┴────┴────┴────┴────┴────┴────┴────┴────┴────┘ 1700
          Thr Asp Thr Ser Leu Val Ser Ser Cys Leu Ala Arg Lys •
          GCTGAATGCAGAAGCCTCGCCAACGTTTGTATCTCGCTATCAAACATAGT
          └────┴────┴────┴────┴────┴────┴────┴────┴────┴────┘ 1750
          AGCTACTCTATGAGGCTGTCTGTTCTCGATTTCAGCTTTATATAGTTTCA
          └────┴────┴────┴────┴────┴────┴────┴────┴────┴────┘ 1800
          TCAAACAGTACATATTCCCTCTGTGGCCACGCAAAAAAAAAAAAAAAAA
          └────┴────┴────┴────┴────┴────┴────┴────┴────┴───→ 1849
```

```
GGGTGGTCTGGATGAAACGTCTTGGCCAAATCGTGATCGATTGATACTCG
|----|----|----|----|----|----|----|----|----|----| 50

CATCTATAAGATGGCACAGATCGACTCTTGATTCACAGACATCCGTCAGC
|----|----|----|----|----|----|----|----|----|----| 100

CCTCAAGCCGTTTGCAAGTCCACAAACACAAGCACAAGCATAGCGTCGCA
|----|----|----|----|----|----|----|----|----|----| 150

ATGAAGTTCCTTCAAGTCCTCCCTGCCCTCATACCGGCCGCCCTGGCCCA
|----|----|----|----|----|----|----|----|----|----| 200
Met Lys Phe Leu Gln Val Leu Pro Ala Leu Ile Pro Ala Ala Leu Ala Gln
                                                            ↑
AACCAGCTGTGACCAGTGGGCAACCTTCACTGGCAACGGCTACACAGTCA
|----|----|----|----|----|----|----|----|----|----| 250
Thr Ser Cys Asp Gln Trp Ala Thr Phe Thr Gly Asn Gly Tyr Thr Val

GCAACAACCTTTGGGGAGCATCAGCCGGCTCTGGATTTGGCTGCGTGACG
|----|----|----|----|----|----|----|----|----|----| 300
Ser Asn Asn Leu Trp Gly Ala Ser Ala Gly Ser Gly Phe Gly Cys Val Thr

GCGGTATCGCTCAGCGGCGGGGCCTCCTGGCACGCAGACTGGCAGTGGTC
|----|----|----|----|----|----|----|----|----|----| 350
Ala Val Ser Leu Ser Gly Gly Ala Ser Trp His Ala Asp Trp Gln Trp Ser

CGGCGGCCAGAACAACGTCAAGTCGTACCAGAACTCTCAGATTGCCATTC
|----|----|----|----|----|----|----|----|----|----| 400
Gly Gly Gln Asn Asn Val Lys Ser Tyr Gln Asn Ser Gln Ile Ala Ile

CCCAGAAGAGGACCGTCAACAGCATCAGCAGCATGCCCACCACTGCCAGC
|----|----|----|----|----|----|----|----|----|----| 450
Pro Gln Lys Arg Thr Val Asn Ser Ile Ser Ser Met Pro Thr Thr Ala Ser

TGGAGCTACAGCGGGAGCAACATCCGCGCTAATGTTGCGTATGACTTGTT
|----|----|----|----|----|----|----|----|----|----| 500
Trp Ser Tyr Ser Gly Ser Asn Ile Arg Ala Asn Val Ala Tyr Asp Leu Phe

CACCGCAGCCAACCCGAATCATGTCACGTACTCGGGAGACTACGAACTCA
|----|----|----|----|----|----|----|----|----|----| 550
Thr Ala Ala Asn Pro Asn His Val Thr Tyr Ser Gly Asp Tyr Glu Leu

TGATCTGGTAAGCCATAAGAAGTGACCCTCCTTGATAGTTTCGACTAACA
|----|----|----|----|----|----|----|----|----|----| 600
Met Ile Trp
```

FIG._5A

```
ACATGTCTTGAGGCTTGGCAAATACGGCGATATTGGGCCGATTGGGTCCT
                                                   650
         Leu Gly Lys Tyr Gly Asp Ile Gly Pro Ile Gly Ser

CACAGGGAACAGTCAACGTCGGTGGCCAGAGCTGGACGCTCTACTATGGC
                                                   700
Ser Gln Gly Thr Val Asn Val Gly Gly Gln Ser Trp Thr Leu Tyr Tyr Gly

TACAACGGAGCCATGCAAGTCTATTCCTTTGTGGCCCAGACCAACACTAC
                                                   750
Tyr Asn Gly Ala Met Gln Val Tyr Ser Phe Val Ala Gln Thr Asn Thr Thr

CAACTACAGCGGAGATGTCAAGAACTTCTTCAATTATCTCCGAGACAATA
                                                   800
Asn Tyr Ser Gly Asp Val Lys Asn Phe Phe Asn Tyr Leu Arg Asp Asn

AAGGATACAACGCTGCAGGCCAATATGTTCTTAGTAAGTCACCCTCACTG
                                                   850
Lys Gly Tyr Asn Ala Ala Gly Gln Tyr Val Leu Ser

TGACTGGGCTGAGTTTGTTGCAACGTTTGCTAACAAAACCTTCGTATAGG
                                                   900

CTACCAATTTGGTACCGAGCCCTTCACGGGCAGTGGAACTCTGAACGTCG
                                                   950
Tyr Gln Phe Gly Thr Glu Pro Phe Thr Gly Ser Gly Thr Leu Asn Val

CATCCTGGACCGCATCTATCAACTAAAACCTGGAAACGTGAGATGTGGTG
                                                   1000
Ala Ser Trp Thr Ala Ser Ile Asn * * *

GGCATACGTTATTGAGCGAGGGAAAAAAAGCATTGGATCCATTGAAGATG
                                                   1050
```

FIG._5B

| FIG._5A |
|---------|
| FIG._5B |

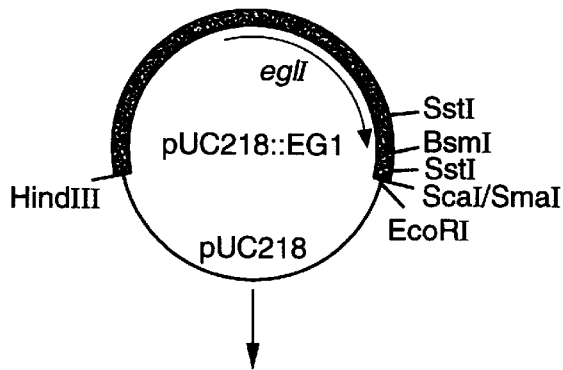

- Digest with BsmI and EcoRI
- Isolate 300bp BsmI/EcoRI Fragment
- Digest pUC218 with SstI and EcoRI
- Ligate pUC218 SstI/EcoRI and BamI/EcoRI
  fragment with the following synthetic oligonucleotides     (SEQ. ID NO:37)

```
    CGTAGAGCGTTGACTTGCCTGTGGTCTGTCCAGACGGGGGACGATAGAATGCG
    TCGAGCATCTCGCAACTGAACGGACACCAGACAGGTCTGCCCCCTGCTATCTTAC
SstI                                                          BsmI
```

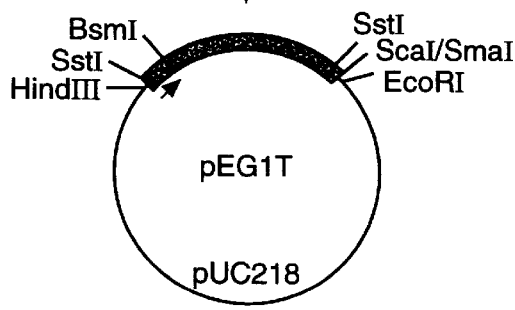

- Digest pEG1T with HindIII and BsmI and Isolate vector fragment
- Digest pUC218::EG1 with HindIII and SstI and Isolate 2.3 kb EG1 fragment
- Ligate pEG1T HindIII/BsmI and 2.3 Kb HindIII/SstI with the
  following synthetic oligonucleotides

```
    CGTAGAGCGTTGACTTGCCTGTGGTCTGTCCAGACGGGGGACGATAGAATGCG
    TCGAGCATCTCGCAACTGAACGGACACCAGACAGGTCTGCCCCCTGCTATCTTAC
SstI                                                          BsmI
```

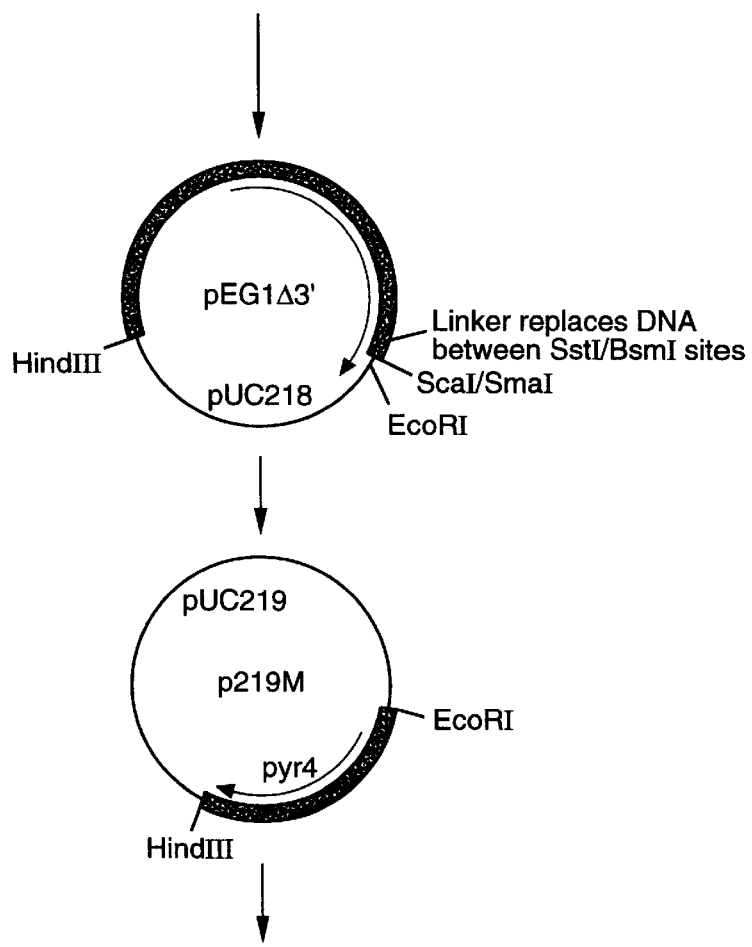
- Digest p219M with EcoRI and HindIII
- Isolate 1.6Kb EcoRI/HindIII *pyr4* gene fragment
- Digest pUC218 with EcoRI SstI and dephosphorylate the ends with calf alkaline phosphotase
- Isolate the HindIII/EcoRI EG1 fragment from pEG1Δ3'
- Ligate together pUC18 EcoRI, EcoRI/HindIII *pyr4* gene fragment and HindIII/EcoRI EG1 fragment
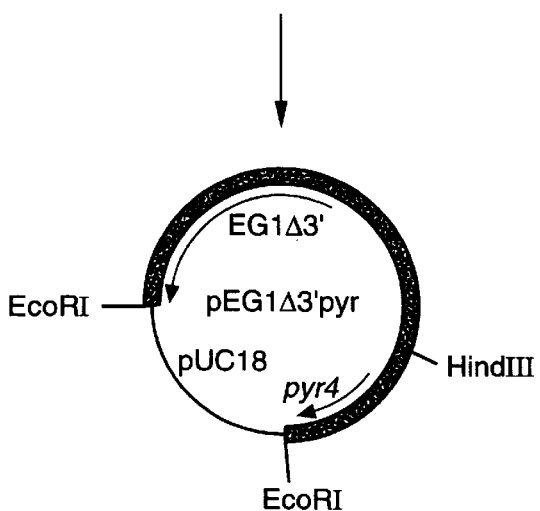
*FIG._6B*

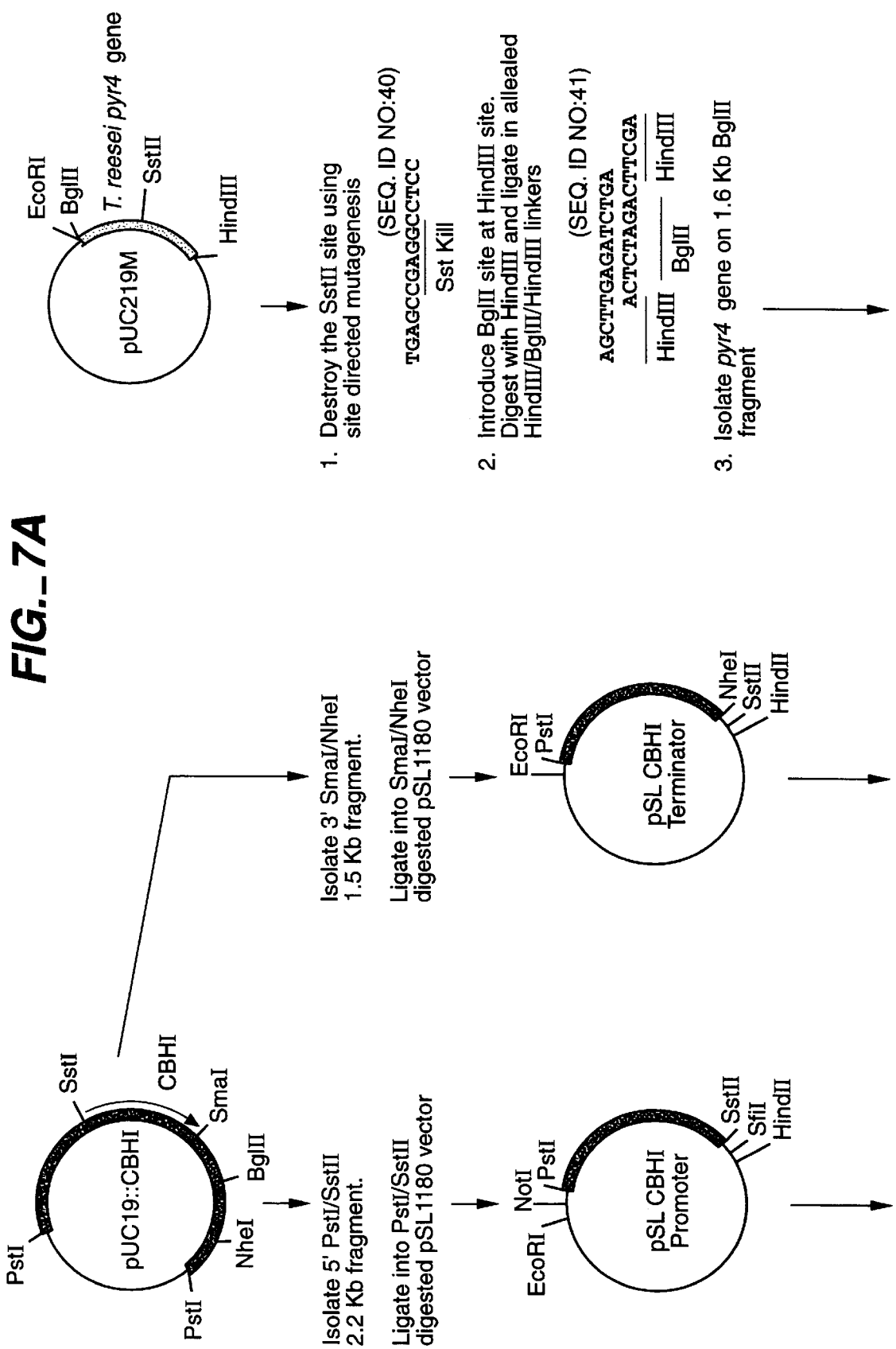
FIG._7A

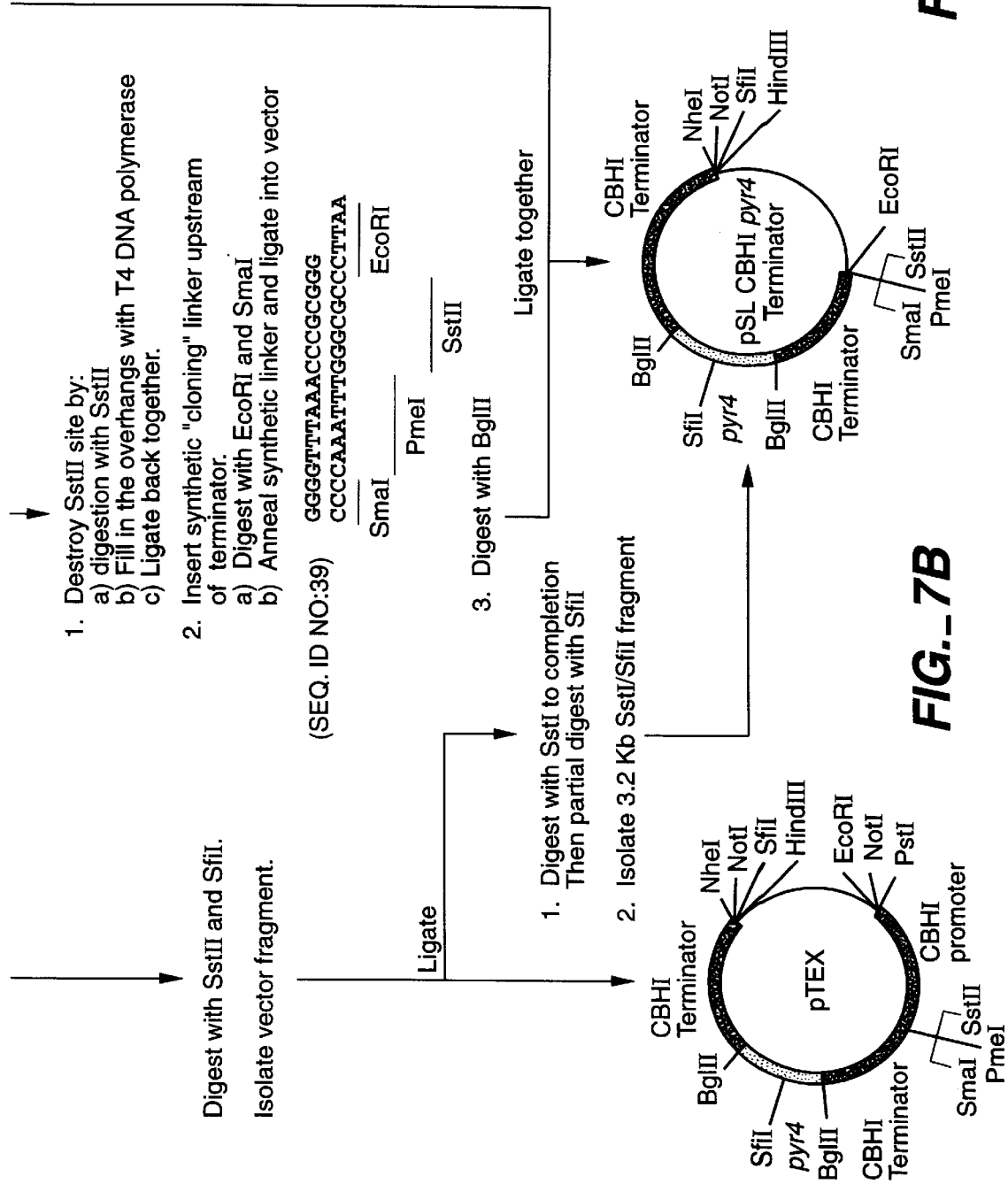

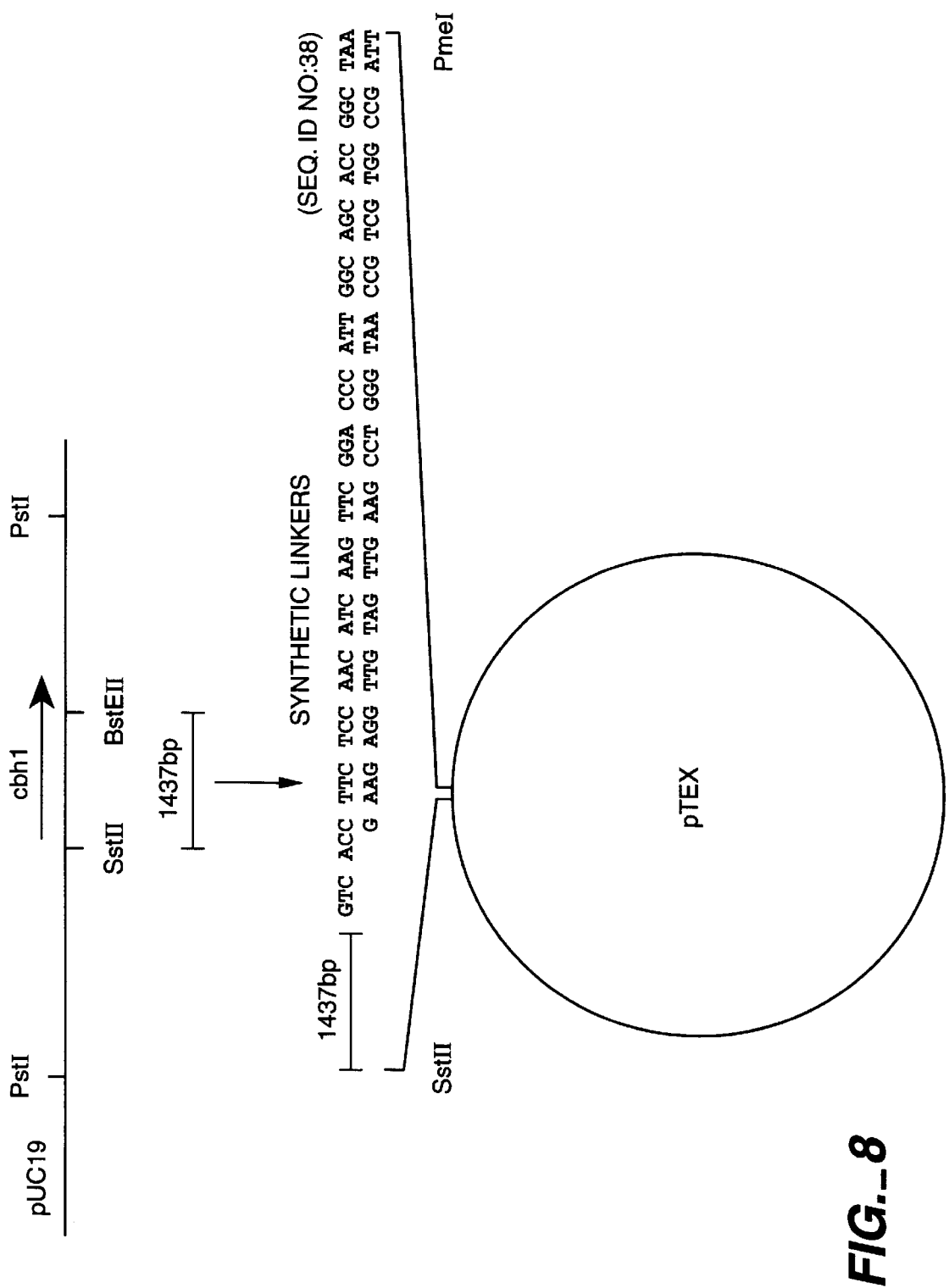
FIG._8

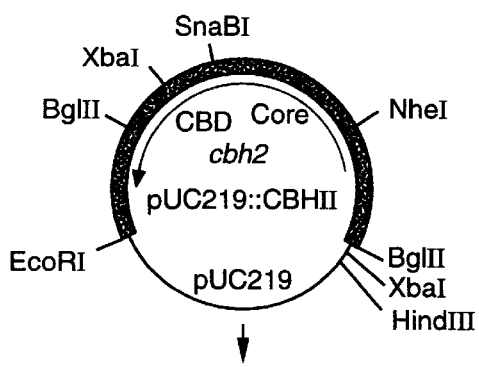

- Partial digest with XbaI. Isolate Linear vector fragment. Fill in the overhangs with T4 DNA polymerase and dNTPs and ligate the blunt ends together. This has the effect of destroying the filled in site.
- Select a plasmid in which the XbaI site in the polylinker has been destroyed.
- Digest the plasmid with the polylinker XbaI site destroyed with XbaI and SnaBI.
- Isolate the vector fragment and ligate with the following synthetic oligonucleotides

```
5'CTA GAG GAG CGG TCG GGA ACC GCT AC 3'
   3' TC CTC GCC AGC CCT TGG CGA TG 5'
  XbaI                            SnaBI
```

- This effectively replaces the CBD with a linker that joins the signal peptidase signal with the papain cleavage point in the linker domain of the CBHII protein

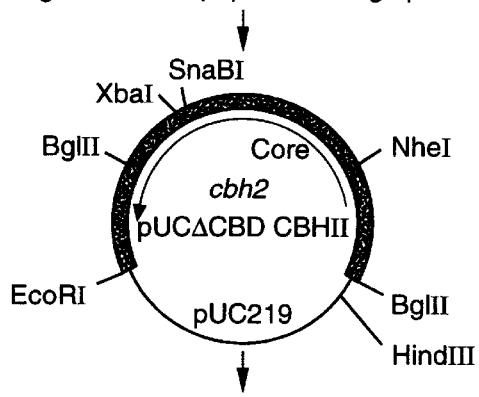

- Digest pUCΔCBD CBHII with NheI
- Blunt the NheI overhangs using T4 DNA polymerase and dNTPs
- Digest with BglII and isolate the NheI (blunt) - BglII cbh2 core domain fragment

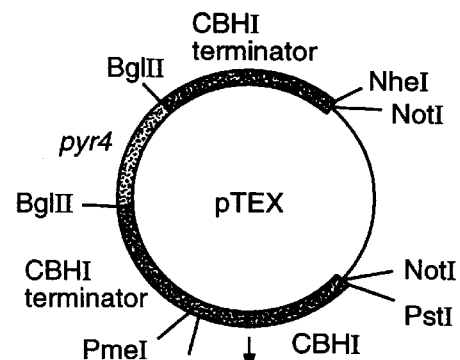

- Digest with SstII and PmeI and isolate the vector fragment

Ligate together with the synthetic oligonucleotide CGCTAG to link the BglII overhang with the SstII overhang

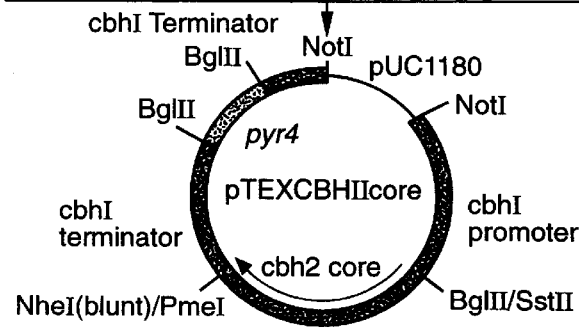

FIG._9

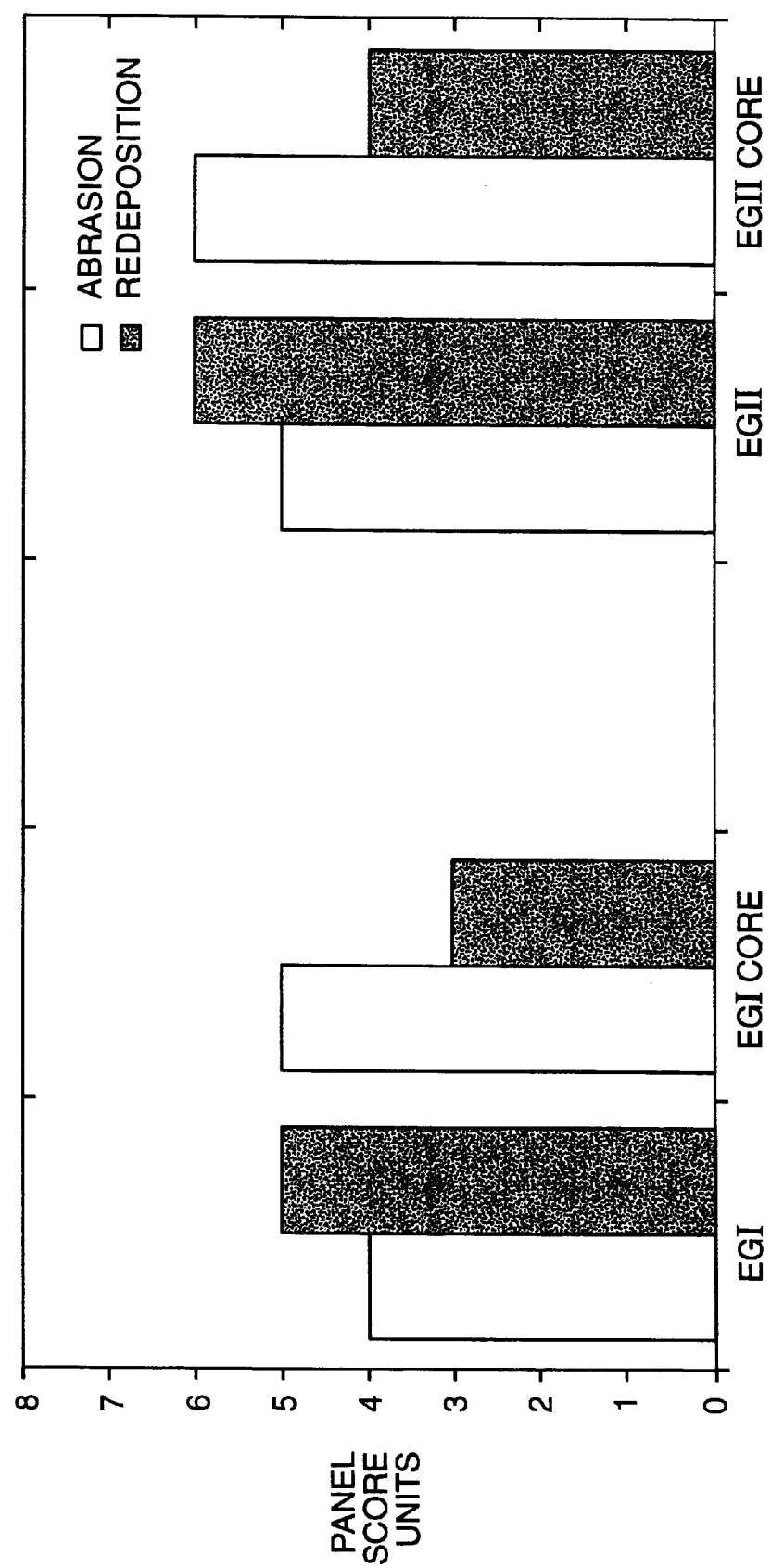
FIG._10

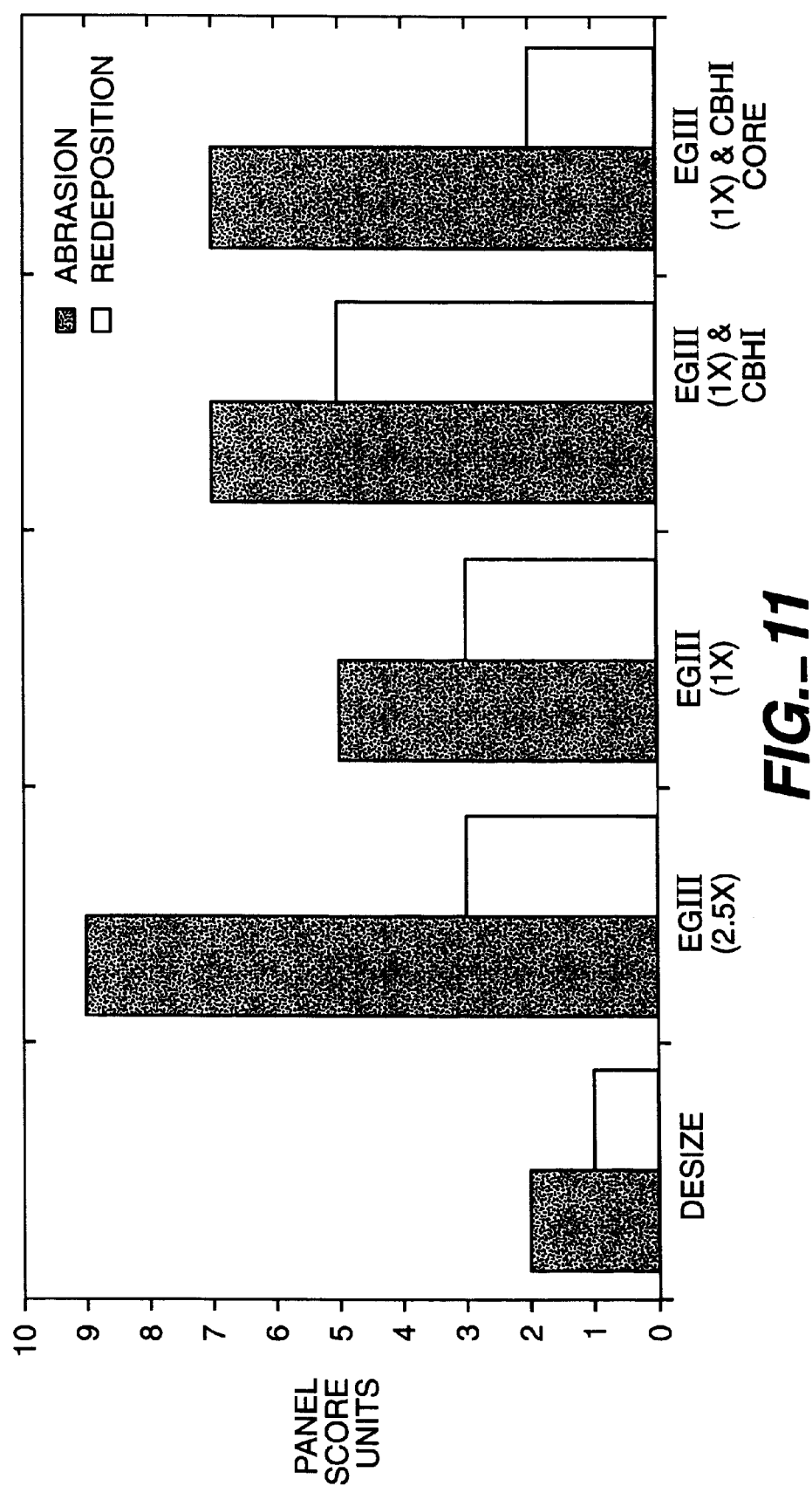
FIG._11

METHOD AND COMPOSITIONS FOR TREATING CELLULOSE CONTAINING FABRICS USING TRUNCATED CELLULASE ENZYME COMPOSITIONS

CROSS-REFERENCE TO RELATED APPLICATIONS

This application is a continuation-in-part of U.S. Ser. No. 08/169,948 filed Dec. 17, 1993, now pending and which is incorporated herein by reference in its entirety.

BACKGROUND OF THE INVENTION

A. Field of the Invention

The present invention is directed to improved methods for treating cotton-containing fabrics and non-cotton containing cellulose fabrics with cellulase as well as to the fabrics produced from these methods. In particular, the improved methods of the present invention are directed to contacting cotton-containing fabrics and non-cotton containing fabrics with an aqueous solution containing a cellulase composition which comprises one or more truncated cellulase enzymes.

B. State of the Art

During or shortly after their manufacture, cotton-containing fabrics can be treated with cellulase in order to impart desirable properties to the fabric. For example, in the textile industry, cellulase has been used to improve the feel and/or appearance of cotton-containing fabrics, to remove surface fibers from cotton-containing knits, for imparting a stone washed appearance to cotton-containing denims and the like.

In particular, Japanese Patent Application Nos. 58-36217 and 58-54032 as well as Ohishi et al., "Reformation of Cotton Fabric by Cellulase" and JTN December 1988 journal article "What's New—Weight Loss Treatment to Soften the Touch of Cotton Fabric" each disclose that treatment of cotton-containing fabrics with cellulase results in an improved feel for the fabric. It is generally believed that this cellulase treatment removes cotton fuzzing and/or surface fibers which reduces the weight of the fabric. The combination of these effects imparts improved feel to the fabric.

Additionally, it was heretofore known in the art to treat cotton-containing knitted fabrics with a cellulase solution under agitation and cascading conditions, for example, by use of a jet, for the purpose of removing broken fibers and threads common to these knitted fabrics.

Clothing made from cellulose fabric, such as cotton denim, is stiff in texture due to the presence of sizing compositions used to ease manufacturing, handling and assembling of clothing items and typically has a fresh dark dyed appearance. One desirable characteristic of indigo-dyed denim cloth is the alteration of dyed threads with white threads, which gives denim a white on blue appearance.

After a period of extended wear and laundering, the clothing items, particularly denim, can develop in the clothing panels and on seams, localized areas of variation in the form of a lightening, in the depth or density of color. In addition, a general fading of the clothes, some pucker in seams and some wrinkling in the fabric panels can often appear. Additionally, after laundering, sizing is substantially removed from the fabric resulting in a softer feel. In recent years such a distressed or "stonewashed" look, particularly in denim clothing, has become very desirable to a substantial proportion of the public.

Previous methods for producing the distressed look included stonewashing of a clothing item or items in a large tub with pumice stones having a particle size of about 1 to 10 inches and with smaller pumice particles generated by the abrasive nature of the process. Typically the clothing item is tumbled with the pumice while wet for a sufficient period such that the pumice abrades the fabric to produce in the fabric panels, localized abraded areas of lighter color and similar lightened areas in the seams. Additionally the pumice softens the fabric and produces a fuzzy surface similar to that produced by the extended wear and laundering of the fabric. This method produced the desired white on blue contrast described above.

The use of the pumice stones has several disadvantages, including overload damage to the machine motors, mechanical damage to transport mechanisms and washing drums, environmental waste problems from the grit produced and high labor costs associated with the manual removal of the stones from the pockets of the garments.

In view of the problems associated with pumice stones in stonewashing, cellulase solutions are used as a replacement for the pumice stones under agitating and cascading conditions, i.e., in a rotary drum washing machine, to impart a "stonewashed" appearance to the denim (U.S. Pat. No. 4,832,864).

Cellulases are enzymes which hydrolyze cellulose ($\beta$-1, 4-D-glucan linkages) and produce as primary products glucose, cellobiose, cellooligosaccharides, and the like. Cellulases are produced by a number of microorganisms and comprise several different enzyme classifications including those identified as exo-cellobiohydrolases (CBH), endoglucanases (EG) and $\beta$-glucosidases (BG) (Schulein, M, 1988 Methods in Enzymology 160:235–242).

The enzymes within these classifications can be separated into individual components. For example, the cellulase produced by the filamentous fungus, *Trichoderma longibrachiatum*, hereafter *T.longibrachiatum*, consists of at least two CBH components, i.e., CBHI and CBHII, and at least four EG components, i.e., EGI, EGII, EGIII and EGV (Saloheimo, A. et al 1993 in Proceedings of the second TRICEL symposium on *Trichoderma reesei* Cellulases and Other Hydrolases, Espoo, Finland, ed by P. Suominen & T. Reinikainen. Foundation for Biotechnical and Industrial Fermentation Research 8:139–146) components, and at least one $\beta$-glucosidase. The genes encoding these components are namely cbh1, cbh2, egl1, egl2, egl3, and egl5 respectively.

The complete cellulase system comprising CBH, EG and BG components synergistically act to convert crystalline cellulose to glucose. The two exo-cellobiohyrolases and the four presently known endoglucanases act together to hydrolyze cellulose to small cello-oligosaccharides. The oligosaccharides (mainly cellobioses) are subsequently hydrolyzed to glucose by a major $\beta$-glucosidase (with possible additional hydrolysis from minor $\beta$-glucosidase components).

A problem with the use of complete cellulase compositions from *Trichoderma sp.* microorganisms and other fungal sources for stonewashing dyed denim is the incomplete removal of colorant caused by redeposition or backstaining of some of the dye back onto the cloth during the stonewashing process. In the case of denim fabric, this causes recoloration of the blue threads and blue coloration of the white threads, resulting in less contrast between the blue and white threads and abrasion points (i.e., a blue on blue look rather than the preferred white on blue). See, *American Dyestuff Reporter,* September 1990, pp. 24–28. This redeposition is objectionable to some users.

Trichoderma cellulases, even though they result in backstaining are preferred because of their higher activity on denim material. In addition, cellulases with a higher degree of purity may be beneficial in the present invention. High specific activity or a high level of purity results in a higher degree of abrasion in a significantly shorter processing time and therefor, is preferable to the denim processors.

Attempts to reduce the amount of redeposition of dye included the addition of extra chemicals or enzymes, such as surfactants, proteases or other agents, into the cellulase wash to help disperse the loosened dye. In addition, processors have used less active whole cellulase, along with extra washings. However, this results in additional chemical costs and longer processing times. Another method includes the use of a mild bleach agent or stain removing agent in the process. This method affects the garment's final shade and increases the processing time. Finally the use of enzymes and stones together leave the processor with all the problems caused by the use of the stones alone. Accordingly, it would be desirable to find a method to prevent redeposition of colorant during stonewashing with cellulases.

Protein analysis of the cellobiohydrolases (CBHI and CBHII) and major endoglucanases (EGI and EGII) of *T. longibrachiatum* has shown that a bifunctional organization exists in the form of a catalytic core domain and a smaller cellulose binding domain separated by a linker or flexible hinge stretch of amino acids rich in proline and hydroxyamino acids. Genes for the two cellobiohydrolases, CBHI and CBHII (Shoemaker, S et al 1983 Bio/Technology 1, 691–696, Teeri, T et al 1983, Bio/Technology 1, 696–699 and Teeri, T. et al, 1987, Gene 51, 43–52) and two major endoglucansases, EGI and EGII (Penttila, M. et al 1986, Gene 45, 253–263, Van Arsdell, J.N/ et al 1987 Bio/Technology 5, 60–64 and Saloheimo, M. et al 1988, Gene 63, 11–21) has been isolated from *T. longibrachiatum* and the protein domain structure has been confirmed.

A similar bifunctional organization of cellulase enzymes is found in bacterial cellulases. The cellulose binding domain (CBD) and catalytic core of *Cellulomonas fimi* endoglucanase A (C. fimi Cen A) has been studied extensively (Ong E. et al 1989, Trends Biotechnol. 7:239–243, Pilz et al 1990, Biochem J. 271:277–280 and Warren et al 1987, Proteins 1:335–341). Gene fragments encoding the CBD and the CBD with the linker have been cloned, expressed in *E. coli* and shown to possess novel activities on cellulose fibers (Gilkes, N. R. et al 1991, Microbiol. Rev. 55:305–315 and Din, N et al 1991, Bio/Technology 9:1096–1099). For example, isolated CBD from *C. fimi* Cen A genetically expressed in *E. coli* disrupts the structure of cellulose fibers and releases small particles but has no detectable hydrolytic activity. CBD further possess a wide application in protein purification and enzyme immobilization. On the other hand, the catalytic domain of *C. fimi* Cen A isolated from protease cleaved cellulase does not disrupt the fibril structure of cellulose and instead smooths the surface of the fiber.

*Trichoderma longibrachiatum* CBHI core domains have been separated proteolytically and purified but only milligram quantities are isolated by this biochemical procedure (Offord D., et al 1991, Applied Biochem. and Biotech. 28/29:377–386). Similar studies were done in an analysis of the core and binding domains of CBHI, CBHII, EGI and EGII isolated from *T. longibrachiatum* after biochemical proteolysis, however, only enough protein was recovered for structural and functional analysis (Tomme, P et al, 1988, Eur.J. Biochem 170:575–581 and Ajo, S, 1991 FEBS 291:45–49). Accordingly, the prior art has failed to recognize the improvements possible in textile processing when using cellulase core domain or cellulose binding domain regions.

SUMMARY OF THE INVENTION

It is an object of the present invention to provide a method of treating cellulose containing fabrics which results in reduced redeposition of dye at an equivalent level of abrasion of the fabric treated over prior art methods.

It is a further object of the present invention to provide a detergent composition having the properties of reduced redeposition of dye at an equivalent level of abrasion over prior art detergent compositions.

It is a further object of the present invention to provide a stonewashing composition having the properties of reduced redeposition of dye at an equivalent level of abrasion over prior art stonewashing compositions.

According to the present invention a method is provided for treating cellulose containing fabrics with cellulase comprising the steps of: (a) contacting said cellulose containing fabric with a treating composition comprising an effective amount of truncated cellulase enzyme, derivative thereof or naturally occurring cellulase containing no cellulase binding domain; and (b) incubating said cellulose containing fabric in contact with said truncated cellulase enzymes, derivative thereof or naturally occurring cellulase containing no cellulase binding domain for a time and under temperature effective to treat said fabric. Also, a composition is provided for treating a cellulose containing fabric comprising a truncated cellulase. In a preferred embodiment the method of treating comprises laundering or stonewashing. Also, preferably, the truncated enzyme comprises a truncated cellulase core. Most preferably the truncated cellulase core comprises EGI core, EGII core, CBHI core, or CBHII core. Further preferably, the cellulase is present in a concentration of from about 0.1 to 1,000 ppm, more preferably from about 0.5 to about 250 ppm.

According to a preferred embodiment of the present invention, a detergent or stonewashing composition is provided comprising truncated cellulase enzyme. Because of the surprising reduced redeposition activity of the truncated cellulase enzyme compositions according to the present invention, cellulose containing fabrics would be enhanced to a surprising extent upon cleaning or stonewashing with a suitable composition comprising truncated enzyme.

An advantage of the present invention is that a cellulase composition comprising truncated cellulase core enzymes, alone or in combination with other truncated cellulase core or non-truncated cellulases, is provided which confers desirable qualities to cellulose containing fabrics.

BRIEF DESCRIPTION OF THE DRAWINGS

FIG. 1(a)–1(c) depicts the genomic DNA and amino acid sequence of CBHI derived from *Trichoderma longibrachiatum*. The signal sequence begins at base pair 210 and ends at base pair 260 (Seq ID No. 25). The catalytic core domain begins at base pair 261 through base pair 671 of the first exon, base pair 739 through base pair 1434 of the second exon, and base pair 1498 through base pair 1713 of the third exon (Seq ID No. 9). The linker sequence begins at base pair 1714 and ends at base pair 1785 (Seq ID No. 17). The cellulose binding domain begins at base pair 1786 and ends at base pair 1888 (Seq ID No. 1). Seq ID Nos. 26, 10, 18 and 2 represent the amino acid sequence of the CBHI signal sequence, catalytic core domain, linker region and binding domain, respectively.

FIG. 2(a)–2(e) depicts the genomic DNA and amino acid sequence of CBHII derived from *Trichoderma longibrachiatum*. The signal sequence begins at base pair 614 and ends at base pair 685 (Seq ID No. 27). The cellulose binding domain begins at base pair 686 through base pair 707 of exon one, and base pair 755 through base pair 851 of exon two (Seq ID No. 3). The linker sequence begins at base pair 852 and ends at base pair 980 (Seq ID No. 19). The catalytic core begins at base pair 981 through base pair 1141 of exon two, base pair 1199 through base pair 1445 of exon three and base pair 1536 through base pair 2221 of exon four (Seq ID No. 11). Seq ID Nos. 28, 4, 20 and 12 represent the amino acid sequence of the CBHII signal sequence, binding domain, linker region and catalytic core domain, respectively.

FIG. 3 depicts the genomic DNA and amino acid sequence of EGI. The signal sequence begins at base pair 113 and ends at base pair 178 (Seq ID No. 29). The catalytic core domain begins at base pair 179 through 882 of exon one, and base pair 963 through base pair 1379 of the second exon (Seq ID No. 13). The linker region begins at base pair 1380 and ends at base pair 1460 (Seq ID No. 21). The cellulose binding domain begins at base pair 1461 and ends at base pair 1616 (Seq ID No. 5). Seq ID Nos. 30, 14, 22 and 6 represent the amino acid sequence of EGI signal sequence, catalytic core domain, linker region and binding domain, respectively.

FIG. 4 depicts the genomic DNA and amino acid sequence of EGII. The signal sequence begins at base pair 262 and ends at base pair 324 (Seq ID No. 31). The cellulose binding domain begins at base pair 325 and ends at base pair 432 (Seq ID No. 7). The linker region begins at base pair 433 and ends at base pair 534 (Seq No. 23). The catalytic core domain begins at base pair 535 through base pair 590 in exon one, and base pair 765 through base pair 1689 in exon two (Seq ID No. 15). Seq ID Nos. 32, 8, 24 and 16 represent the amino acid sequence of EGII signal sequence, binding domain, linker region and catalytic core domain, respectively.

FIG. 5 depicts the genomic DNA and amino acid sequence of EGIII. The signal sequence begins at base pair 151 and ends at base pair 198 (Seq ID No. 35). The catalytic core domain begins at base pair 199 through base pair 557 in exon one, base pair 613 through base pair 833 in exon two and base pair 900 through base pair 973 in exon three (Seq ID No. 33). Seq ID Nos. 36 and 34 represent the amino acid sequence of EGIII signal sequence and catalytic core domain, respectively.

FIG. 6 illustrates the construction of EGI core domain expression vector (Seq ID No. 37).

FIG. 7 depicts the construction of the expression plasmid pTEX (Seq ID Nos. 39–41).

FIG. 8 is an illustration of the construction of CBHI core domain expression vector (Seq ID No. 38).

FIG. 9 is an illustration of the construction of the CBHII core domain expression vector.

FIG. 10 illustrates abrasion/redeposition results obtained which compare EGI with EGI core and EGII with EGII core.

FIG. 11 illustrates the improvement in abrasion/redeposition results of EGIII treated denim when CBHI core is added.

DETAILED DESCRIPTION OF THE INVENTION

I. Definitions

"Cotton-containing fabric" means sewn or unsewn fabrics made of pure cotton or cotton blends including cotton woven fabrics, cotton knits, cotton denims, cotton yarns and the like. When cotton blends are employed, the amount of cotton in the fabric should be at least about 40 percent by weight cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Cellulose containing fabric" means any cotton or non-cotton containing cellulosic fabric or cotton or non-cotton containing cellulose blend including natural cellulosics and manmade cellulosics (such as jute, flax, ramie, rayon, TENCEL™). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g. lyocell). Of course, included within the definition of cellulose containing fabric is any garment or yarn made of such materials. Similarly, "cellulose containing fabric" includes textile fibers made of such materials.

"Treating composition" means a composition comprising a truncated cellulase component which may be used in treating a cellulose containing fabric. Such treating includes, but is not limited to, stonewashing, modifying the texture, feel and/or appearance of cellulose containing fabrics or other techniques used during manufacturing of cellulose containing fabrics. Additionally, treating within the context of this invention contemplates the removal of "dead cotton", from cellolosic fabric or fibers, i.e. immature cotton which is significantly more amorphous than mature cotton. Dead cotton is known to cause uneven dyeing. Additionally, "treating composition" means a composition comprising a truncated cellulase component which may be used in washing of a soiled manufactured cellulose containing fabric. For example, truncated cellulase may be used in a detergent composition for washing laundry. Detergent compositions useful in accordance with the present invention include special formulations such as pre-wash, pre-soak and home-use color restoration compositions. Treating compositions may be in the form of a concentrate which requires dilution or in the form of a dilute solution or form which can be applied directly to the cellulose containing fabric.

It is Applicants' present belief that the action pattern of cellulase upon cellulose containing fabrics does not differ significantly whether used as a stonewashing composition during manufacturing or during laundering of a soiled manufactured cellulose containing fabric. Thus, improved properties such as abrasion, redeposition of dye, strength loss and improved feel conferred by a certain cellulase or mixture of cellulases are obtained in both detergent and manufacturing processes incorporating cellulase. of course, the formulations of specific compositions for the various textile applications of cellulase, e.g., stonewashing or laundry detergent or pre-soak, may differ due to the different applications to which the respective compositions are directed, as indicated herein. However, the improvements effected by the addition of cellulase compositions will be generally consistent through each of the various textile applications.

"Stonewashing composition" means a formulation for use in stonewashing cellulose containing fabrics. Stonewashing compositions are used to modify cellulose containing fabrics prior to presentation for consumer sale, i.e., during the manufacturing process, in contrast to detergent compositions which are intended for the cleaning of soiled garments.

"Stonewashing" means the treatment of colored cellulose containing fabric with a cellulase solution under agitating and cascading conditions, i.e., in a rotary drum washing machine, which impart a "stonewashed" appearance to the denim. Methods for imparting a stonewashed appearance to denim are described in U.S. Pat. No. 4,832,864 which is incorporated herein by reference in its entirety. Generally, stonewashing techniques have been applied to dyed denim.

"Detergent composition" means a mixture which is intended for use in a wash medium for the laundering of soiled cellulose containing fabrics. In the context of the present invention, such compositions may include, in addition to cellulases and surfactants, many additives, including, but not limited to, additional hydrolytic enzymes, builders, bleaching agents, bluing agents and fluorescent dyes, caking inhibitors, masking agents, cellulase activators, antioxidants, and solubilizers may be included. Such compositions are generally used for cleaning soiled garments and are not used during the manufacturing process, in contrast to stonewashing compositions.

"Redepositing cellulase" means cellulases which in the enzymatic stonewashing or other treatment of cellulose containing fabrics using cellulase solutions, particularly denim, result in redeposition of dye onto the substrate. This effect is often referred to as backstaining. Such backstaining of the fabric leads to incomplete stonewashing because instead of the desired blue on white contrast, the redeposition results in blue on blue. Redepositing cellulases include those derived from microorganisms such as the fungal microorganism *Trichoderma sp.* and the like. In particular, EGI, EGII, CBHI and CBHII are known to exhibit significant redeposition behavior in their non-truncated state.

"Surface active agent or surfactant" means anionic, non-ionic and ampholytic surfactants well known for their use in detergent compositions.

"Wash medium" means an aqueous wash solution prepared by adding a requisite amount of a detergent composition to water. The wash medium generally contains a cleaning effective amount of the detergent.

"Cellulolytic enzymes" or "Cellulase enzymes" means fungal exoglucanases or exo-cellobiohydrolases, endoglucanases, and β-glucosidases. These three different types of cellulase enzymes act synergistically to convert cellulose and its derivatives to glucose. Analysis of the genes coding for CBHI, CBHII, EGI, EGII and EGV in *Trichoderma longibrachiatum* shows a domain structure comprising a catalytic core region or domain (CCD), a hinge or linker region (used interchangeably herein) and cellulose binding region or domain (CBD).

A cellulase composition produced by a naturally occurring source and which comprises one or more cellobiohydrolase type and endoglucanase type components wherein each of these components is found at the ratio produced by the source is sometimes referred to herein as a "complete cellulase system" or a "complete cellulase composition" to distinguish it from the classifications and components of cellulase isolated therefrom, from incomplete cellulase compositions produced by bacteria and some fungi, from a cellulase composition obtained from a microorganism genetically modified so as to overproduce, underproduce, or not produce one or more of the cellobiohydrolase type and/or endoglucanase type components of cellulase, or from a truncated cellulase enzyme composition, as defined herein.

The present invention specifically contemplates applicability to cellulases which contain core and binding domain regions as defined herein. For example, bacterial cellulases from *Thermonospora sp., Cellulomonas sp., Bacillus sp., Pseudomonas sp., Streptomyces sp.* are known to possess both a binding domain region and a core region.

Preferred for use in this invention are fungal cellulases. More preferably, the fungal cellulases are derived from *Trichoderma sp.*, including *Trichoderma longibrachiatum, Trichoderma viride, Trichoderma koningii, Penicillium sp., Humicola, sp.*, including *Humicola insolens, Aspergillus sp.*, and *Fumarium sp.* As used herein, the term "Trichoderma" or "*Trichoderma sp.*" refers to any fungal strains which have previously been classified as Trichoderma or which are currently classified as Trichoderma. Most preferably, the cellulase's derived from *Trichoderma longibrachiatum* or *Trichoderma viride.*

"Fungal cellulase" means an enzyme composition derived from fungal sources or microorganisms genetically modified so as to incorporate and express all or part of the cellulase genes obtained from a fungal source. Fungi capable of producing cellulases useful in preparing cellulase compositions described herein are disclosed in British Patent No. 2 094 826A, the disclosure of which is incorporated herein by reference.

Most fungal cellulases generally have their optimum activity in the acidic or neutral pH range although some fungal cellulases are known to possess significant activity under neutral and slightly alkaline conditions, i.e., for example, cellulase derived from *Humicola insolens* is known to have activity in neutral to slightly alkaline conditions.

Fungal cellulases are known to be comprised of several enzyme classifications having different substrate specificity, enzymatic action patterns, and the like. Additionally, enzyme components within each classification can exhibit different molecular weights, different degrees of glycosylation, different isoelectric points, different substrate specificity etc. For example, fungal cellulases can contain cellulase classifications which include endoglucanase type components (hereinafter "EG-type"), exo-cellobiohydrolase type components (hereinafter "CBH-type"), β-glucosidase type components (hereinafter "BG-type"), etc. On the other hand, while bacterial cellulases are reported in the literature as containing little or no CBH-type components, there are a few cases where CBH-type components derived from bacterial cellulases have been reported to possess exo-cellobiohydrolase activity.

The fermentation procedures for culturing fungi and for production of cellulase are known per se in the art. For example, cellulase systems can be produced either by solid or submerged culture, including batch, fed-batch and continuous-flow processes. The collection and purification of the cellulase systems from the fermentation broth can also be effected by procedures known per se in the art.

"Endoglucanase-type components" or "EG-type" means fungal cellulase components or a combination of components which exhibit textile activity properties similar to the endoglucanase components of *Trichoderma longibrachiatum* (previously classified as *Trichoderma reesei*). In this regard, the endoglucanase components of *Trichoderma longibrachiatum* (for example, EGI, EGII, EGIII, and EGV, either alone or in combination) are known to impart improved feel, improved appearance, softening, color enhancement, and/or a stonewashed appearance to denim fabrics (as compared to the fabric prior to treatment) when these components are incorporated into a textile treatment medium and the fabric is treated with this medium.

Accordingly, endoglucanase type components are those cellulase components which impart specific enhancements to cellulose containing fabrics, such as improved feel, improved appearance, softening, color enhancement, and/or a stonewashed appearance (as compared to the fabric before treatment) when these components are incorporated into a medium used to treat the fabrics. Certain EG type components, including EGI, EGII and EGIII, may impart reduced strength loss to denim fabrics as compared to the strength loss arising from treatment with a similar cellulase composition but which additionally contains CBH I type components.

Endoglucanase type components as defined herein may not include components traditionally classified as endoglucanases using activity tests such as the ability of the component (a) to hydrolyze soluble cellulose derivatives such as carboxymethylcellulose (CMC), thereby reducing the viscosity of CMC containing solutions, (b) to readily hydrolyze hydrated forms of cellulose such as phosphoric acid swollen cellulose (e.g., Walseth cellulose) and hydrolyze less readily the more highly crystalline forms of cellulose (e.g., Avicel, Solkafloc, etc.). On the other hand, it is believed that not all endoglucanase components, as defined by such activity tests, will impart one or more of the enhancements to cellulose containing fabrics, including reduced strength loss. Accordingly, for the purposes herein, it is appropriate to define endoglucanase type components as those components of fungal cellulase which possess similar textile modification properties as possessed by the endoglucanase components of *Trichoderma longibrachiatum*.

The different components generally have different properties, such as isoelectric point, molecular weight, degree of glycosylation, substrate specificity and enzymatic action patterns. The different isoelectric points of the components allow for their separation via techniques such as ion exchange chromatography. In fact, the isolation of components from different sources is known in the art. See, for example, Bjork et al., U.S. Pat. No. 5,120,463; Schulein et al., International Application WO 89/09259; Wood et al., *Biochemistry and Genetics of Cellulose Degradation*, pp. 31–52 (1988); Wood et al., *Carbohydrate Research*, Vol. 190, pp. 279–297 (1989); Schulein, *Methods in Enzymology*, Vol. 160, pp. 234–242 (1988); and the like. The entire disclosure of each of these references is incorporated herein by reference.

The term "EGI" refers to an endoglucanase type component typically derived from, or embodying the identifying characteristics of those derived from, EGI of *Trichoderma sp*. Thus, EGI refers to an endoglucanase derived from *Trichoderma sp*. characterized by a pH optimum of about 4.0 to 6.0, an isoelectric point (pI) of from about 4.5 to 4.7, and a molecular weight of about 47 to 49 Kdaltons. Preferably, EGI is derived from either *Trichoderma longibrachiatum* or from *Trichoderma viride*. EGI derived from *Trichoderma longibrachiatum* has a pH optimum of about 5.0, an isoelectric point (pI) of about 4.7 and a molecular weight of about 47 to 49 Kdaltons. EGI cellulase derived from *Trichoderma viride* has a pH optimum of about 5.0, an isoelectric point (pI) of about 5.3 and a molecular weight of about 50 Kdaltons.

The term "EGII" as defined herein refers to an endoglucanase type component typically derived from, or embodying the identifying characteristics of those derived from, EGII of *Trichoderma sp*. It is noted that EGII has been previously referred to by the nomenclature "EGIII" by some authors but current nomenclature uses the term EGII. In any event, the EGII protein defined herein is substantially different from the EGIII protein in its molecular weight, pI and pH optimum. The term "EGII cellulase" refers to the endoglucanase component derived from *Trichoderma spp*. characterized by a pH optimum of about 4.0 to 6.0 an isoelectric point (pI) of from about 5.5, and a molecular weight of about 48 Kdaltons. Preferably, EGII cellulase is derived from either *Trichoderma longibrachiatum* or from *Trichoderma viride*.

The term "EGIII cellulase" as defined herein refers to an endoglucanase type component typically derived from, or embodying the identifying characteristics of those derived from, EGIII of *Trichoderma sp*. Thus, EGIII refers to the endoglucanase component derived from *Trichoderma spp*. characterized by a pH optimum of about 5.0 to 7.0, an isoelectric point (pI) of from about 7.2 to 8.0, and a molecular weight of about 23 to 28 Kdaltons. Preferably, EGIII cellulase is derived from either *Trichoderma longibrachiatum* or from *Trichoderma viride*. EGIII cellulase derived from *Trichoderma longibrachiatum* has a pH optimum of about 5.5 to 6.0, an isoelectric point (pI) of about 7.4 and a molecular weight of about 25 to 28 Kdaltons. EGIII cellulase derived from *Trichoderma viride* has a pH optimum of about 5.5, an isoelectric point (pI) of about 7.7 and a molecular weight of about 23.5 Kdaltons.

The term "EGV cellulase" as defined herein refers to an endoglucanase type component typically derived from, or embodying the identifying characteristics of those derived from, EGV of *Trichoderma sp*. Thus EGV refers to the endoglucanase component derived from *Trichoderma sp*. characterized by Saloheimo et al., *Molecular Microbiology* 13(2):219–228 (1994); and Proceedings of the Second TRICEL Symposium on *Trichoderma reesei* Cellulases and other Hydrolases, Esppo Finland 1993, ed. P. Suominen & J.T. Reinikainen. Foundation for Biotechnical and Industrial Fermentation Research 8, pp. 139–146 (1993).

"Exo-cellobiohydrolase type components" or "CBH-type" means fungal cellulase components which exhibit textile activity properties similar to CBH I and/or CBH II cellulase components of *Trichoderma longibrachiatum*. In this regard, when used in the absence of EG type cellulase components (as defined above), CBH I and CBH II components of *Trichoderma longibrachiatum* alone are recognized as not imparting any significant enhancements in feel, appearance, softening color enhancement and/or stonewashed appearance to denim fabrics. Additionally, when used in combination with some EG type components, in a ratio of approximately 2.5:1 of CBH I to EG components, the CBH I component of *Trichoderma longibrachiatum* imparts enhanced strength loss to the denim fabrics.

Accordingly, CBH I type components and CBH II type components refer to those fungal cellulase components which exhibit textile activity properties similar to CBH I and CBH II components of *Trichoderma longibrachiatum*, respectively. As noted above, for CBH I type components, this includes the property of increasing strength loss in denim fabrics treated with CBH I in the presence of EG type components.

Exo-cellobiohydrolase type components defined herein may not include components traditionally classified as exo-cellobiohydrolases using activity tests such as those used to characterize CBH I and CBH II from *Trichoderma longi-*

*brachiatum*. For example, exo-cellobiohydrolase type components (a) are competitively inhibited by cellobiose ($K_i$ approximately 1 mM); (b) are unable to hydrolyze substituted celluloses to any significant degree, such as carboxymethylcellulose, and (c) hydrolyze phosphoric acid swollen cellulose and to a lesser degree highly crystalline cellulose. On the other hand, it is believed that some cellulase components which are characterized as CBH type components by these activity tests, will impart improved feel, appearance, softening, color enhancement, and/or a stonewashed appearance to cellulose-containing fabrics when used alone in the cellulase composition. Accordingly, it is believed to be more accurate for the purposes herein to define such exo-cellobiohydrolases as EG-type components because these components possess similar functional properties in textile uses to those possessed by the endoglucanase components of *Trichoderma longibrachiatum*.

In general, cellulase compositions comprising the various components of a complete cellulase composition ("whole cellulase" can be obtained by purification techniques based on their known characteristics and properties. Specifically, the whole cellulase can be purified into substantially pure components by recognized separation techniques published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. After purification, the requisite amount of the desired components could be recombined.

The term "truncated cellulase", as used herein, refers to a protein comprising a truncated cellulase catalytic core or truncated cellulose binding domain of exo-cellobiohydrolase or endoglucanase, for example, EGI type, EGII type, EGV type, CBHI type, CBHII type, or derivatives thereof. As stated above, many cellulase enzymes are believed to be bifunctional in that they contain domains which are directed toward both catalytic or hydrolytic activity with respect to the cellulose substrate, and also non-catalytic cellulose binding activity. Thus, a truncated cellulase is a cellulase which in an intact form, contains both a core and a binding domain but which is treated so as to lack one or the other domain.

The catalytic core and the cellulose binding domain of a cellulase enzyme are believed to act together in a synergistic manner to effect efficient and often deleterious hydrolysis of cellulose fibers in a cellulose containing fabric. Further, cellulase catalytic activity and cellulose binding activity are believed to be specific to distinct structural domains. For example, as indicated above, many cellulase enzymes, including cellulases from, for example, *T. longibrachiatum* and *Humicola insolens* are known to incorporate a catalytic core domain subunit which is attached via a linker region to a cellulose binding domain subunit.

A "truncated cellulase derivative" encompasses a truncated cellulase core or truncated cellulose binding domain, as defined herein, wherein there may be an addition or deletion of one or more amino acids to either or both of the C- and N-terminal ends of the truncated cellulase, or a substitution, insertion or deletion of one or more amino acids at one or more sites throughout the truncated cellulase. Derivatives include mutants that preserve their character as truncated cellulase core or truncated cellulose binding domain, as defined below. It is also intended by the term "derivative of a truncated cellulase" to include core or binding domains of the exoglucanase or endoglucanase enzymes that have attached thereto one or more amino acids from the linker region.

A truncated cellulase derivative further refers to a protein substantially similar in structure and biological activity to a truncated cellulase core or truncated cellulose binding domain protein, but which has been genetically engineered to contain a modified amino acid sequence. Thus, provided that the two proteins possess substantially similar activity, they are considered "derivatives" even if the primary structure of one protein does not possess the identical amino acid sequence to that found in the other.

It is contemplated that a truncated cellulase derivative may be derived from a DNA fragment encoding a catalytic truncated core or a truncated cellulose binding domain which further contains an addition of one or more nucleotides internally or at the 5' or 3' end of the DNA fragment, a deletion of one or more nucleotides internally or at the 5' or 3' end of the DNA fragment or a substitution of one or more nucleotides internally or at the 5' or 3' end of the DNA fragment wherein the functional activity of the expressed truncated cellulose binding or catalytic core domain (truncated cellulase derivative) is retained. A DNA fragment encoding a cellulase catalytic core or cellulose binding domain may further include a linker or hinge DNA sequence or portion thereof attached to the core or binding domain DNA sequence at either the 5' or 3' end wherein the functional activity of the encoded truncated cellulose binding domain or cellulase core domain (truncated cellulase derivative) is retained.

The term "truncated cellulase core" or "truncated cellulase region" refers herein to a peptide comprising the catalytic core domain of exo-cellobiohydrolase or endoglucanase, for example, EGI type, EGII type, EGV type, CBHI type or CBHII type, or a derivative thereof that is capable of enzymatically cleaving cellulose polymers, including but not limited to pulp or phosphoric acid swollen cellulose. However, a truncated cellulase core will not possess cellulose binding activity attributable to a cellulose binding domain. A truncated cellulase core is distinguished from a non-truncated cellulase which, in an intact form, possesses poor cellulose binding activity. A truncated cellulase core may include other entities which do not include cellulose binding activity attributable to a cellulose binding domain. For example, the presence of a linker or hinge is specifically contemplated. Similarly, the covalent attachment of another enzymatic entity to the truncated cellulase core is also specifically contemplated.

The performance (or activity) of a protein containing a truncated catalytic core or a derivative thereof may be determined by methods well known in the art. (See Wood, T. M. et al in Methods in Enzymology, Vol. 160, Editors: Wood, W. A. and Kellogg, S. T., Academic Press, pp. 87–116, 1988) For example, such activities can be determined by hydrolysis of phosphoric acid-swollen cellulose and/or soluble oligosaccharides followed by quantification of the reducing sugars released. In this case the soluble sugar products, released by the action of CBH or EG cellulase core domains or derivatives thereof, can be detected by HPLC analysis or by use of calorimetric assays for measuring reducing sugars. It is expected that these catalytic domains or derivatives thereof will retain at least 10% of the activity exhibited by the intact enzyme when each is assayed under similar conditions and dosed based on similar amounts of catalytic domain protein.

The term "truncated cellulose binding domain" refers herein to a peptide or group of related peptides comprising cellulose binding activity of an exo-cellobiohydrolase or an endoglucanase, for example, EGI type, EGII type, EGV type, CBHI type or CBHII type, or a derivative thereof that non-covalently binds to a polysaccharide such as cellulose. It is believed that cellulose binding domains attach the enzyme to cellulose and function independently from the catalytic core of the cellulase enzyme. A truncated cellulose binding domain will not possess the significant hydrolytic activity attributable to a catalytic core. A truncated cellulose binding domain is distinguished from a non-truncated cellulase which, in an intact form, possesses no cellulase catalytic core. A truncated cellulose binding domain may include other entities which do not include cellulose cleavage activity attributable to cellulase catalytic core. For example, the presence of a linker or hinge is specifically contemplated. Similarly, the covalent attachment of another enzymatic entity to the truncated cellulose binding domain is also specifically contemplated.

The performance (or activity) of a truncated cellulose binding domain or derivatives thereof as described in the present invention may be determined by cellulose binding assays using cellulose substrates such as avicel, pulp or cotton. It is expected that these novel truncated cellulose binding domains or derivatives thereof will retain at least 10% of the binding affinity compared to that exhibited by the non-truncated enzyme when each is assayed under similar conditions and dosed based on similar amounts of binding domain protein. The amount of non-bound binding domain may be quantified by direct protein analysis, by chromatographic methods, or possibly by immunological methods.

Other methods well known in the art that measure cellulase catalytic and/or binding activity via the physical or chemical properties of particular treated substrates may also be suitable in the present invention. For example, for methods that measure physical properties of a treated substrate, the substrate is analyzed for modification of shape, texture, surface, or structural properties, modification of the "wet" ability, e.g. substrates ability to absorb water, or modification of swelling. Other parameters which may determine activity include the measuring of the change in the chemical properties of treated solid substrates. For example, the diffusion properties of dyes or chemicals may be examined after treatment of solid substrate with the truncated cellulose binding protein or derivatives thereof described in the present invention. Appropriate substrates for evaluating activity include Avicel, rayon, pulp fibers, cotton or ramie fibers, paper, kraft or ground wood pulp, for example. (See also Wood, T. M. et al in "Methods in Enzymology", Vol. 160, Editors: Wood, W. A. and Kellogg, S. T., Academic Press, pp. 87–116, (1988)).

In addition to truncated cellulase core, naturally occurring cellulases which lack a binding domain possess the advantages of the truncated catalytic cores defined herein. For example, bacterial cellulase derived from *Erwinia carotovora* are believed to possess no binding domain, (see e.g., Saarilahti, et al. Gene, Vol. 90, pp. 9–14 (1990)). Similarly, cellulases derived from *Clostridium thermocellum,* also are believed to possess no binding domain (see e.g. Gilkes, et al., Microbiological Reviews, pp. 303–315 (1991)). Thus, the use of naturally occurring cellulases having no binding domain will provide decreased backstaining at equivalent levels of abrasion to known cellulases.

"β-Glucosidase (BG) components" means components of a complete cellulase composition which exhibit BG activity; that is to say that such components will act from the non-reducing end of cellobiose and other soluble cellooligosaccharides ("cellobiose") and give glucose as the sole product. BG components do not adsorb onto or react with cellulose polymers. Furthermore, such BG components are competitively inhibited by glucose ($K_i$ approximately 1 mM). While in a strict sense, BG components are not literally cellulases because they cannot degrade cellulose, such BG components are included within the definition of the cellulase system because these enzymes facilitate the overall degradation of cellulose by further degrading the inhibitory cellulose degradation products (particularly cellobiose) produced by the combined action of CBH type components and EG type components.

Methods to either increase or decrease the amount of BG components in the cellulase composition is disclosed in WO 92/10581 which application is incorporated herein by reference in its entirety.

"Linker or hinge region" means a short peptide region that links together structurally distinct catalytic core and cellulose binding domains of a cellulase. These domains in *T. longibrachiatum* cellulases, for example, are linked by a peptide rich in Ser, Thr and Pro.

"Signal sequence" means a sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

"Host cell" means a cell which acts as a host for a recombinant DNA vector according to the present invention. In a preferred embodiment according to the present invention, "host cell" means both the cells and protoplasts created from the cells of *Trichoderma sp.*

"DNA construct or vector" (used interchangeably herein) means a nucleotide sequence which comprises one or more DNA fragments or DNA variant fragments encoding any of the novel truncated cellulases or derivatives described above.

"Functionally attached to" means that a regulatory region, such as a promoter, terminator, secretion signal or enhancer region is attached to a structural gene and controls the expression of that gene.

"Buffer" means art recognized acid/base reagents which stabilize the cellulase solution against undesired pH shifts during cellulase treatment of the cellulose containing fabric. In this regard, it is art recognized that cellulase activity is pH dependent. For example, a specific cellulase composition will exhibit cellulolytic activity within a defined pH range with optimal cellulolytic activity generally being found within a small portion of this defined range. The specific pH range for cellulolytic activity will vary with each cellulase composition. As noted above, while most cellulases will exhibit cellulolytic activity within an acidic to neutral pH profile, there are some cellulase compositions which exhibit cellulolytic activity in an alkaline pH environment.

During cellulase treatment of the cellulose containing fabric, it is possible that the pH of the initial cellulase solution could be outside the range required for cellulase activity. It is further possible for the pH to change during treatment of the cellulose containing fabric, for example, by the generation of a reaction product which alters the pH of the solution. In either event, the pH of an unbuffered cellulase solution could be outside the range required for cellulolytic activity. When this occurs, undesired reduction or cessation of cellulolytic activity in the cellulase solution occurs.

In view of the above, the pH of the cellulase solution should be maintained within the range required for cellulolytic activity. One means of accomplishing this is by simply monitoring the pH of the system and adjusting the pH as required by the addition of either an acid or a base. However, in a preferred embodiment, the pH of the system is preferably maintained within the desired pH range by the use of a buffer in the cellulase solution. In general, a sufficient amount of buffer is employed so as to maintain the pH of the solution within the range wherein the employed cellulase exhibits activity. Insofar as different cellulase compositions have different pH ranges for exhibiting cellulase activity, the specific buffer employed is selected in relationship to the specific cellulase composition employed. The buffer(s) selected for use with the cellulase composition employed can be readily determined by the skilled artisan taking into account the pH range and optimum for the cellulase composition employed as well as the pH of the cellulase solution. Preferably, the buffer employed is one which is compatible with the cellulase composition and which will maintain the pH of the cellulase solution within the pH range required for optimal activity. Suitable buffers include sodium citrate, ammonium acetate, sodium acetate, disodium phosphate, and any other art recognized buffers.

II. Preparation of Truncated Cellulase Enzymes

The present invention relates to the use of truncated cellulases and derivatives of truncated cellulases. These enzymes are preferably prepared by recombinant methods. Additionally, truncated cellulase proteins for use in the present invention may be obtained by other art recognized means such as chemical cleavage or proteolysis of complete cellulase protein.

A preferred mode for preparing truncated cellulase according to the present invention comprises obtaining a modified *Trichoderma sp.* host cell that is missing one or more cellulase activities. The modified *Trichoderma sp.* cell is transformed with a DNA construct comprising at least a fragment of DNA encoding a portion or all of the binding or core region of a exo-cellobiohydrolase or an endoglucanase, for example, EGI, EGII, EGV, CBHI or CBHII functionally attached to a promoter. The transformed host cell is then grown under conditions so as to express the desired protein. Subsequently, the desired protein product is purified to substantial homogeneity.

Preferably, the microorganism to be transformed comprises a strain derived from *Trichoderma sp.* More preferably, the strain comprises *T. longibrachiatum* cellulase over-producing strain. For example, RL-P37, described by Sheir-Neiss et al. in Appl. Microbiol. Biotechnology, 20 (1984) pp. 46–53 is known to secrete elevated amounts of cellulase enzymes. Functional equivalents of RL-P37 include *Trichoderma longibrachiatum* strain RUT-C30 (deposited under deposit no. ATCC No. 56765) and ATCC deposit nos. 58351, 58352, and 58353.

Still more preferably, the Trichoderma host cell strains have had one or more cellulase genes deleted prior to introduction of a DNA construct or plasmid containing the DNA fragment encoding the truncated cellulase protein. Such strains may be prepared by the method disclosed in U.S. Pat. No. 5,246,853 and WO 92/06209, which disclosures are hereby incorporated by reference. By expressing a truncated cellulase in a host microorganism that is missing one or more cellulase genes, the identification and subsequent purification procedures are simplified. Any gene from *Trichoderma sp.* which has been cloned can be deleted, for example, the cbh1, cbh2, egl1, and egl3 genes.

Gene deletion may be accomplished by inserting a form of the desired gene to be deleted or disrupted into a plasmid by methods known in the art. An appropriate deletion plasmid will generally have unique restriction enzyme sites present therein to enable the fragment of homologous *Trichoderma sp.* DNA to be removed as a single linear piece. The deletion plasmid is then cut at an appropriate restriction enzyme site(s), internal to the coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene.

A selectable marker must be chosen so as to enable detection of the transformed fungus. Any selectable marker gene which is expressed in the selected microorganism will be suitable. For example, with *Trichoderma sp.*, the selectable marker is chosen so that the presence of the selectable marker in the transformants will not significantly affect the properties thereof. Such a selectable marker may be a gene which encodes an assayable product. For example, a functional copy of a *Trichoderma sp* gene may be used which if lacking in the host strain results in the host strain displaying an auxotrophic phenotype.

In a preferred embodiment, a pyr4$^-$ derivative strain of *Trichoderma sp.* is transformed so that one or more cellulase genes are replaced by the pyr4 gene, thus providing a selectable marker. A pyr4$^-$ derivative strain may be obtained by subjecting *Trichoderma sp.* strains to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4$^-$ derivative strains which lack a functional orotidine monophosphate decarboxylase enzyme and require uridine for growth by selecting for FOA resistance. Using the FOA selection technique it is also possible to obtain uridine requiring strains which lack a functional orotate pyrophosphoribosyl transferase. It is possible to transform these cells with a functional copy of the gene encoding this enzyme (Berges and Barreau, 1991, Curr. Genet. 19 pp 359–365). Selection of derivative strains is easily performed using the FOA resistance technique referred to above, and thus, the pyr4 gene is preferably employed as a selectable marker.

To transform pyr4$^-$ *Trichoderma sp.* so as to be lacking in the ability to express one or more cellulase genes, a single DNA fragment comprising a disrupted or deleted cellulase gene is then isolated from the deletion plasmid and used to transform an appropriate pyr$^-$ Trichoderma host. Transformants are then identified and selected based on their ability to express the pyr4 gene product and thus compliment the uridine auxotrophy of the host strain. Southern blot analysis is then carried out on the resultant transformants to identify and confirm a double cross over integration event which replaces part or all of the coding region of the gene to be deleted with the pyr4 selectable markers.

Although the specific plasmid vectors described above relate to preparation of pyr$^-$ transformants, the present invention is not limited to these vectors. Various genes can be deleted and replaced in the *Trichoderma sp.* strain using the above techniques. In addition, any available selectable markers can be used, as discussed above. In fact, any *Trichoderma sp.* gene which has been cloned, and thus identified, can be deleted from the genome using the above-described strategy.

As stated above, the host strains used are derivatives of *Trichoderma sp.* which lack or have a nonfunctional gene or genes corresponding to the selectable marker chosen. For example, if the selectable marker of pyr4 is chosen, then a specific pyr derivative strain is used as a recipient in the transformation procedure. Similarly, selectable markers comprising *Trichoderma sp.* genes equivalent to the *Aspergillus nidulans* genes argB, trpC, niaD may be used. The corresponding recipient strain must therefore be a derivative strain such as argB⁻, trpC⁻, niaD⁻, respectively.

DNA encoding the truncated cellulase protein is then prepared for insertion into an appropriate microorganism. According to the present invention, DNA encoding for a truncated cellulase enzyme comprises DNA encoding for a protein which corresponds to the catalytic core region of the cellulase enzyme. Accordingly, DNA may be derived from any microbial source which is known to produce cellulase, where the gene is identified and isolated. In a preferred embodiment, the DNA encodes for a truncated cellulase protein derived from *Trichoderma sp.*, and more preferably from *Trichoderma longibrachiatum*. Thus, the DNA may encode for an EGI, EGII, CBHI or CBHII core protein. Preferably, the DNA gene fragment or variant DNA fragment codes for the core or binding domains of a *Trichoderma sp.* cellulase or derivative thereof that additionally retains the functional activity of the truncated core or binding domain, respectively. Further, the DNA fragment or variant thereof comprising the sequence of the core or binding domain regions may additionally have attached thereto a linker, or hinge region DNA sequence or portion thereof wherein the encoded truncated cellulase still retains either cellulase core or binding domain activity, respectively.

The DNA fragment or DNA variant fragment encoding the truncated cellulase or derivative may be functionally attached to a fungal promoter sequence, for example, the promoter of the cbh1 or egi1 gene. It is also contemplated that more than one copy of DNA encoding a truncated cellulase may be recombined into the strain.

The DNA encoding the truncated cellulase protein may be prepared by the construction of an expression vector carrying the DNA encoding the truncated cellulase. The expression vector carrying the inserted DNA fragment encoding the truncated cellulase may be any vector which is capable of replicating autonomously in a given host organism, typically a plasmid. In preferred embodiments two types of expression vectors for obtaining expression of genes or truncations thereof are contemplated. The first contains DNA sequences in which the promoter, gene coding region, and terminator sequence all originate from the gene to be expressed. The gene truncation is obtained by deleting away the undesired DNA sequences (coding for unwanted domains) to leave the domain to be expressed under control of its own transcriptional and translational regulatory sequences. A selectable marker is also contained on the vector allowing the selection for integration into the host of multiple copies of the novel gene sequences.

For example, pEGIΔA3'pyr contains the EGI cellulase core domain under the control of the EGI promoter, terminator, and signal sequences. The 3' end on the EGI coding region containing the cellulose binding domain has been deleted. The plasmid also contains the pyr4 gene for the purpose of selection.

The second type of expression vector is preassembled and contains sequences required for high level transcription and a selectable marker. It is contemplated that the coding region for a gene or part thereof can be inserted into this general purpose expression vector such that it is under the transcriptional control of the expression cassettes promoter and terminator sequences.

For example, PTEX is such a general purpose expression vector. Genes or part thereof can be inserted downstream of the strong CBHI promoter. The Examples disclosed herein are included in which cellulase catalytic core and binding domains are shown to be expressed using this system.

In the vector, the DNA sequence encoding the truncated cellulase or other novel proteins of the present invention should be operably linked to transcriptional and translational sequences, i.e., a suitable promoter sequence and signal sequence in reading frame to the structural gene. The promoter may be any DNA sequence which shows transcriptional activity in the host cell and may be derived from genes encoding proteins either homologous or heterologous to the host cell. The signal peptide provides for extracellular expression of the truncated cellulase or derivatives thereof. The DNA signal sequence is preferably the signal sequence naturally associated with the truncated gene to be expressed, however the signal sequence from any exo-cellobiohydrolases or endoglucanase is contemplated in the present invention.

The procedures used to ligate the DNA sequences coding for the truncated cellulases, derivatives thereof or other novel cellulases of the present invention with the promoter, and insertion into suitable vectors containing the necessary information for replication in the host cell are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall in *Trichoderma sp.* is very low. Accordingly, uptake of the desired DNA sequence, gene or gene fragment is at best minimal. There are a number of methods to increase the permeability of the *Trichoderma sp.* cell wall in the derivative strain (i.e., lacking a functional gene corresponding to the used selectable marker) prior to the transformation process.

The preferred method in the present invention to prepare *Trichoderma sp.* for transformation involves the preparation of protoplasts from fungal mycelium. The mycelium can be obtained from germinated vegetative spores. The mycelium is treated with an enzyme which digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M to 1.2 M. It is preferable to use about a 1.2 M solution of sorbitol in the suspension medium.

Uptake of the DNA into the host *Trichoderma sp.* strain is dependent upon the calcium ion concentration. Generally between about 10 Mm $CaCl_2$ and 50 Mm $CaCl_2$ is used in an uptake solution. Besides the need for the calcium ion in the uptake solution, other items generally included are a buffering system such as TE buffer (10 Mm Tris, Ph 7.4; 1 Mm EDTA) or 10 Mm MOPS, Ph 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the *Trichoderma sp.* strain and the plasmid DNA is transferred to the nucleus. This fusion frequently leaves multiple copies of the plasmid DNA tandemly integrated into the host chromosome.

Usually a suspension containing the *Trichoderma sp.* protoplasts or cells that have been subjected to a permeability treatment at a density of $10^8$ to $10^9$/ml, preferably $2 \times 10^8$/ml are used in transformation. These protoplasts or cells are added to the uptake solution, along with the desired linearized selectable marker having substantially homologous flanking regions on either side of said marker to form a transformation mixture. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if $Pyr^+$ transformants are being selected it is preferable to use a growth medium that contains no uridine. The subsequent colonies are transferred and purified on a growth medium depleted of uridine.

At this stage, stable transformants were distinguished from unstable transformants by their faster growth rate and the formation of circular colonies with a smooth, rather than ragged outline on solid culture medium lacking uridine. Additionally, in some cases a further test of stability was made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the truncated cellulases or derivatives thereof are recovered in active form from the host cell either as a result of the appropriate post translational processing of the novel truncated cellulase or derivative thereof.

The truncated cellulases are recovered from the medium by conventional techniques including separations of the cells from the medium by centrifugation, filtration, and precipitation of the proteins in the supernatant or filtrate with a salt, for example, ammonium sulphate. Additionally, chromatography procedures such as ion exchange chromatography, affinity chromatography may be used. Alternatively, the secreted protein product may be isolated and purified by binding to a polysaccharide substrate or antibody matrix. The antibodies (polyclonal or monoclonal) may be raised against cellulase core or binding domain peptides, or synthetic peptides may be prepared from portions of the core domain or binding domain and used to raise polyclonal antibodies.

The DNA transformed into the host cell may comprise additional embodiments. For example, cellulase enzymes are contemplated which combine a core region derived from either a homologous or heterologous microbial source.

III. Methods Of Treating Cellulose Containing Fabric Using Truncated Cellulase Enzymes As noted above, the present invention pertains to methods for treating cellulose containing fabrics with a truncated cellulase enzyme. The use of the truncated cellulase composition of this invention provides the novel and surprising result of effecting a relatively low level of dye redeposition while maintaining an equivalent level of abrasion compared to prior art cellulase treatment. Because the level of abrasion acts as an indicator of the quality and effectiveness of particular cellulase treatment techniques, e.g., stonewashing or laundering, the use of the instant invention provides a surprisingly high quality textile treatment composition. In the laundering context, abrasion is sometimes referred to as color is clarification, defuzzing or biopolishing.

The present invention specifically contemplates the use of truncated cellulase core, alone or in combination with additional cellulase components, to achieve excellent abrasion with reduced redeposition when compared to non-truncated cellulase. Additionally, naturally occurring cellulase enzymes which lack a binding domain are contemplated as within the scope of the invention. It is also contemplated that the methods of this invention will provide additional enhancements to treated cellulose containing fabric, including improvements in the feel and/or appearance of the fabric.

A. Methodology for Stonewashing With Truncated Cellulase Compositions

According to the present invention, the truncated cellulase compositions described above may be employed as a stonewashing composition. Preferably, the stonewashing composition of the instant comprises an aqueous solution which contains an effective amount of a truncated cellulase together with other optional ingredients including, for example, a buffer, a surfactant, and a scouring agent.

An effective amount of truncated cellulase enzyme composition is a concentration of truncated cellulase enzyme sufficient for its intended purpose. Thus an "effective amount" of truncated cellulase in the stonewashing composition according to the present invention is that amount which will provide the desired treatment, e.g., stonewashing. The amount of truncated cellulase employed is also dependent on the equipment employed, the process parameters employed (the temperature of the truncated cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of truncated cellulase can be readily determined by the skilled artisan based on the above factors as well as the desired result. Preferably the truncated cellulase composition is present in a concentration of from 1–1000 ppm, more preferably 10–400 ppm and most preferably 20–100 ppm total protein.

Optionally, a buffer is employed in the stonewashing composition such that the concentration of buffer is that which is sufficient to maintain the pH of the solution within the range wherein the employed truncated cellulase exhibits activity which, in turn, depends on the nature of the truncated cellulase employed. The exact concentration of buffer employed will depend on several factors which the skilled artisan can readily take into account. For example, in a preferred embodiment, the buffer as well as the buffer concentration are selected so as to maintain the pH of the final truncated cellulase solution within the pH range required for optimal cellulase activity. Preferably, buffer concentration in the stonewashing composition is about 0.001N or greater. Suitable buffers include, for example, citrate and acetate.

In addition to truncated cellulase and a buffer, the stonewashing composition may optionally contain a surfactant. Preferably, the surfactant is present in a concentration in the diluted wash mediums of greater than 100 ppm, preferably from about 200–15,000 ppm. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known in the art.

In a preferred embodiment, a concentrated stonewashing composition can be prepared for use in the methods described herein. Such concentrates would contain concentrated amounts of the truncated cellulase composition described above, buffer and surfactant, preferably in an aqueous solution. When so formulated, the stonewashing concentrate can readily be diluted with water so as to quickly and accurately prepare stonewashing compositions according to the present invention and having the requisite concentration of these additives. Preferably, such concentrates will comprise from about 0.1 to about 50 weight percent of a fungal cellulase composition described above (protein); from about 0.1 to about 80 weight percent buffer; from about 0 to about 50 weight percent surfactant; with the balance being water. When aqueous concentrates are formulated, these concentrates can be diluted so as to arrive at the requisite concentration of the components in the truncated cellulase solution as indicated above. As is readily apparent, such stonewashing concentrates will permit facile formulation of the truncated cellulase solutions as well as permit feasible transportation of the concentration to the location where it will be used. The stonewashing concentrate can be in any art recognized form, for example, liquid, emulsion, gel, or paste. Such forms are well known to the skilled artisan.

When a solid stonewashing concentrate is employed, the cellulase composition may be a granule, a powder, an agglomerate or a solid disk. When granules are used, the granules are preferably formulated so as to contain a cellulase protecting agent. See, for instance, U.S. Ser. No. 07/642,669, filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES," which application is incorporated herein by reference in its entirety. Likewise, the granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the stonewashing composition of the present invention as desired, including stones, pumice, fillers, solvents, enzyme activators, and other anti-redeposition agents.

The cellulose containing fabric is contacted with the stonewashing composition containing an effective amount of the truncated cellulase enzyme or derivative by intermingling the treating composition with the stonewashing composition, and thus bringing the truncated cellulase enzyme into proximity with the fabric. For example, if the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the truncated cellulase enzyme to react efficiently with cellulose containing fabric. The reaction conditions for truncated cellulase core, and thus the conditions effective for the stonewashing compositions of the present invention, are substantially similar to well known methods used with corresponding non-truncated cellulases. Accordingly, the conditions effective for treatment of cellulose containing fabric with a stonewashing composition comprising CBHI type core according to the present invention are substantially similar to those in the prior art using wild-type CBHI type cellulase compositions. Similarly, where a mixture of truncated and non-truncated cellulase is utilized, the conditions should be optimized similar to where a similar combination may have been used. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature which temperature is dependent on the nature of the cellulase used. Thus, if the reaction temperature is permitted to go too high, then the cellulolytic activity is lost as a result of the denaturing of the cellulase. As a result, the maximum reaction temperatures employed herein are generally about 65° C. In view of the above, reaction temperatures are generally from about 30° C. to about 65° C.; preferably, from about 35° C. to about 60° C.; and more preferably, from about 35° C. to about 55° C.

Reaction times are dependent on the specific conditions under which the stonewashing occurs. For example, pH, temperature and concentration of truncated cellulase will all effect the optimal reaction time. Generally, reaction times are from about 5 minutes to about 5 hours, and preferably from about 10 minutes to about 3 hours and, more preferably, from about 20 minutes to about 1 hour.

Cellulose containing fabrics treated in the stonewashing methods described above using truncated cellulase compositions according to the present invention show reduced redeposition of dye as compared to the same cellulose containing fabrics treated in the same manner with an non-truncated cellulase composition.

B. Methodology for Treating Cellulose Containing Fabrics With A Detergent Composition Comprising Truncated Cellulase Enzyme According to the present invention, the truncated cellulase compositons described above may be employed as detergent composition. The detergent compositions according to the present invention are useful as pre-wash compositions, pre-soak compositions, or for detergent cleaning during the regular wash cycle. Preferably, the detergent composition of the present invention comprises an effective amount of truncated cellulase, and a surfactant, and optionally include other ingredients described below.

An effective amount of truncated cellulase employed in the detergent compositions of this invention is an amount sufficient to impart improved abrasion to cellulase containing fabrics. Preferably, the truncated cellulase employed is in a concentration of about 0.001% to about 25%, more preferably, about 0.02% to about 10% by weight percent of detergent.

The specific concentration of truncated cellulase enzyme employed in the detergent composition is preferably selected so that upon dilution into a wash medium, the concentration of truncated cellulase enzyme is in a range of about 0.1 to about 1000 ppm, preferably from about 0.2 ppm to about 500 ppm, and most preferably from about 0.5 ppm to about 250 ppm total protein. Thus, the specific amount of truncated cellulase enzyme employed in the detergent composition will depend on the extent to which the detergent will be diluted upon addition to water so as to form a wash solution.

At lower concentrations of truncated cellulase enzyme, i.e., concentrations of truncated enzyme lower than 20 ppm, the decreased backstaining or redeposition with equivalent surface fiber abrasion when compared to prior art compositions will become evident after repeated washings. At higher concentrations, i.e., concentrations of truncated cellulase enzymes of greater than 40 ppm, the decreased backstaining with equivalent surface fiber removal will become evident after a single wash.

The detergent compositions of the present invention may be in any art recognized form, for example, as a liquid diluent, in granules, in emulsions, in gels, or in pastes. Such forms are well known to the skilled artisan. When a solid detergent composition is employed, the truncated cellulase is preferably formulated as granules. Preferably, the granules can be formulated so as to additionally contain a cellulase protecting agent. See, for instance, U.S. Ser. No. 07/642,669 filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES" which application is incorporated herein by reference in its entirety. Likewise, the granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, nonionic and ampholytic surfactants well known for their use in detergent compositions.

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; alkanesul-fonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants include quaternary ammonium salt sulfonates, betaine-type ampholytic surfactants, and the like. Such ampholytic surfactants have both the positive and negative charged groups in the same molecule.

Nonionic surfactants generally comprise polyoxyalkylene ethers, as well as higher fatty acid alkanolamides or alkylene oxide adduct thereof, fatty acid glycerine monoesters, and the like.

Suitable surfactants for use in this invention are disclosed in British Patent Application No. 2 094 826 A, the disclosure of which is incorporated herein by reference.

Mixtures of such surfactants can also be used.

The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. Upon dilution in the wash medium, the surfactant concentration is generally about 500 ppm or more; and preferably, from about 1000 ppm to 15,000 ppm.

In addition to the cellulase composition and the surfactant (s), the detergent compositions of this invention can optionally contain one or more of the following components:

Hydrolases Except Cellulase

Such hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

Trade names of commercial products and producers are as follows: "Alkalase", "Esperase", "Savinase", "AMG", "BAN", "Fungamill", "Sweetzyme", "Thermamyl" (Novo Industry, Copenhagen, Denmark); "Maksatase", "High-alkaline protease", "Amylase THC", "Lipase" (Gist Brocades, N.V., Delft, Holland); "Protease B-400", "Protease B-4000", "Protease AP", "Protease AP 2100" (Schweizerische Ferment A.G., Basel, Switzerland); "CRD Protease" (Monsanto Company, St. Louis, Mo.); "Piocase" (Piopin Corporation, Monticello, Ill.); "Pronase P", "Pronase AS", "Pronase AF" (Kaken Chemical Co., Ltd., Japan); "Lapidase P-2000" (Lapidas, Secran, France); protease products (Tyler standard sieve, 100% pass 16 mesh and 100% on 150 mesh) (Clington Corn Products, Division of Standard Brands Corp., New York); "Takamine", "Bromelain 1:10", "HT Protease 200", "Enzyme L-W" (obtained from fungi, not from bacteria) (Miles Chemical Company, Elkhart, Ind.); "Rhozyme P-11 Conc.", "Pectinol", "Lipase B", "Rhozyme PF", "Rhozyme J-25" (Rohm & Haas, Genencor, South San Francisco, Calif.); "Ambrozyme 200" (Jack Wolf & Co., Ltd., Subsidiary of Nopco Chemical Company, Newark, N.J.); "ATP 40", "ATP 120", "ATP 160" (Lapidas, Secran, France); "Oripase" (Nagase & Co., Ltd., Japan).

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified one. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic Surfactants and Long-Chain Fatty Acid Salts

Such cationic surfactants and long-chain fatty acid salts include saturated or unsaturated fatty acid salts, alkyl or alkenyl ether carboxylic acid salts, α-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent Sequestering Agents

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or Inorganic Electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, clay, calcium silicate (such as Micro-Cell of Johns Manville Co.), calcium carbonate and magnesium oxide.

Masking Agents for Factors Inhibiting the Cellulase Activity

The cellulase composition of this invention are deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as the inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-Activators

The activators vary depending on variety of the cellulases. In the presence of proteins, cobalt and its salts, magnesium and its salts, and calcium and its salts, potassium and its salts, sodium and its salts or monosac-charides such as mannose and xylose, the cellulases are activated and their deterging powers are improved remarkably.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzene-sulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range of from acidic to alkaline pH. In a preferred embodiment, the detergent composition of the present invention can be used in alkaline detergent wash media and more preferably, alkaline detergent wash media having a pH of from above 7 to no more than about 11.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method and/or spray-drying granulation method are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. The granules have a size of from 50 to 2000 micrometers. After the spray-drying, perfumes, enzymes, bleaching agents, inorganic alkaline builders may be added. With a highly dense, granular detergent base obtained such as by the spray-drying-granulation method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose containing fabrics with detergent compositions according to the present invention, will be readily ascertainable by those of skill in the art. Accordingly, the appropriate conditions effective for treatment with the present detergents will correspond to those using similar detergent compositions which include wild-type cellulase.

As indicated above, detergents according to the present invention may additionally be formulated as a pre-wash in the appropriate solution at an intermediate pH where sufficient activity exists to provide desired improvements in abrasion and reduced strength loss. When the detergent composition is a pre-soak (e.g., pre-wash or pre-treatment) composition, either as a liquid, spray, gel or paste composition, the truncated cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

Also, it is contemplated that compositions comprising truncated cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover.

In order to further illustrate the present invention and advantages thereof, the following specific examples are given with the understanding that they are being offered to illustrate the present invention and should not be construed in any way as limiting its scope.

EXAMPLES

Example 1

Cloning and Expression of EG1 Core Domain Using its Own Promoter, Terminator and Signal Sequence Part 1. Cloning The complete egl1 gene used in the construction of the EG1 core domain expression plasmid, PEGlΔ3'pyr, was obtained from the plasmid PUC218::EG1. (See FIG. 6) The 3' terminator region of egl1 was ligated into PUC218 (Korman, D. et al Curr Genet 17:203–212, 1990) as a 300 bp BsmI-EcoRI fragment along with a synthetic linker designed to replace the 3' intron and cellulose binding domain with a stop codon and continue with the egl1 terminator sequences. The resultant plasmid, PEGlT, was digested with HindIII and BsmI and the vector fragment was isolated from the digest by agarose gel electrophoresis followed by electroelution. The egl1 gene promoter sequence and core domain of egl1 were isolated from PUC218::EG1 as a 2.3kb HindIII-SstI fragment and ligated with the same synthetic linker fragment and the HindIII-BsmI digested PEG1T to form PEG1Δ3'.

The net result of these operations is to replace the 3' intron and cellulose binding domain of egl1 with synthetic oligonucleotides of 53 and 55bp. These place a TAG stop codon after serine 415 and thereafter continued with the egl1 terminator up to the BsmI site.

Next, the T. longibrachiatum selectable marker, pyr4, was obtained from a previous clone p219M (Smith et al 1991), as an isolated 1.6kb EcoRI-HindIII fragment. This was incorporated into the final expression plasmid, PEG1Δ3'pyr, in a three way ligation with PUC18 plasmid digested with EcoRI and dephosphorylated using calf alkaline phosphatase and a HindIII-EcoRI fragment containing the egl1 core domain from PEG1Δ3'.

Part 2. Transformation and Expression

A large scale DNA prep was made of PEG1Δ3'pyr and from this the EcoRI fragment containing the egl1 core domain and pyr4 gene was isolated by preparative gel electrophoresis. The isolated fragment was transformed into the uridine auxotroph version of the quad deleted strain, 1A52 pyr13 (described in U.S. patent application Ser. Nos. 07/770,049, 08/048,728 and 08/048,881, incorporated by reference in its entirety herein), and stable transformants were identified.

To select which transformants expressed egl1 core domain the transformants were grown up in shake flasks under conditions that favored induction of the cellulase genes (Vogels+1% lactose). After 4–5 days of growth, protein from the supernatants was concentrated and either 1) run on SDS polyacrylamide gels prior to detection of the egl1 core domain by Western analysis using EGI polyclonal antibodies or 2) the concentrated supernatants were assayed directly using RBB carboxy methyl cellulose as an endoglucanase specific substrate and the results compared to the parental strain 1A52 as a control. Transformant candidates were identified as possibly producing a truncated EGI core domain protein. Genomic DNA and total mRNA was isolated from these strains following growth on Vogels+1% lactose and Southern and Northern blot experiments performed using an isolated DNA fragment containing only the egl1 core domain. These experiments demonstrated that transformants could be isolated having a copy of the egl1 core domain expression cassette integrated into the genome of 1A52 and that these same transformants produced egl1 core domain mRNA.

One transformant was then grown using media suitable for cellulase production in Trichoderma well known in the art that was supplemented with lactose (Warzymoda, M. et al 1984 French Patent No. 2555603) in a 14L fermentor. The resultant broth was concentrated and the proteins contained therein were separated by SDS polyacrylamide gel electrophoresis and the Egl1 core domain protein identified by Western analysis. (See Example 3 below). It was subsequently estimated that the protein concentration of the fermentation supernatant was about 5–6 g/L of which approximately 1.7–4.4 g/L was EGI core domain based on CMCase activity. This value is based on an average of several EGI core fermentations that were performed.

In a similar manner, any other cellulase domain or derivative thereof may be produced by procedures similar to those discussed above.

Example 2

Purification of EGI and EGII Catalytic Cores

Part 1. EGI catalytic core

The EGI core was purified in the following manner. The concentrated (UF) broth was diluted to 14 mg/ml in 23 mM Na Acetate pH 5.0. Two hundred grams of avicel cellulose gel (FMC Bioproducts, Type PH-101) was added to the diluted EGI core broth and mixed at room temperature for forty five minutes. The avicel was removed from the broth by centrifugation, resulting in an enriched EGI core solution. This solution was then buffer exchanged into 10 mM TES pH 7.5 using a Amicon stirred cell concentrator with a PM 10 membrane (diaflo ultra filtration membranes, Amicon Cat # 13132MEM 5468A). The EGI core sample was then loaded onto an anion exchange column (Q-sepharose fast flow, Pharmacia Cat # 17-0510-01) and eluted in a salt gradient from 0 to 0.5M NaCl in 10 mM TES pH 7.5. The fractions which contained the EGI core were combined and concentrated using the Amicon stirred cell concentrator mentioned above.

Part 2. EGII catalytic core

EGII core was purified in the following manner. The concentrated (UF) broth was filtered using diatomaceous earth. Ammonium sulfate was added to the broth to a final concentration of 1M $(NH_4)_2SO_4$ and this mixture was then loaded on to a hydrophobic column (phenyl-sepharose fast flow, Pharmacia, cat #17-0965-01). The column was washed with 0.75M ammonium sulfate before elution of the EGII core with 0.5M ammonium sulfate. The fractions containing the core were pooled and concentrated using a tangential flow ultra filtration membrane (Filtron Minisette Ultrafiltration System, cat #FS018K01) with an Omega 10K Membrane (Filtron, cat# FS010K75). 100 grams of avicel cellulose gel (FMC Bioproducts, Type PH-101) was added for every gram of concentrated EGII core and mixed for 40 minutes. The avicel was removed by centrifugation resulting in an enriched EGII core solution.

Example 3

Cloning and Expression of CBHII Core Domain Using the CBHI Promoter, Terminator and Signal Sequence from CBHII Part 1. Construction of the T.longibrachiatum general-purpose expression plasmid-PTEX The plasmid, PTEX was constructed following the methods of Sambrook et al. (1989), supra, and is illustrated in FIG. 7. This plasmid has been designed as a multi-purpose expression vector for use in the filamentous fungus Trichoderma longibrachiatum. The expression cassette has several unique features that make it useful for this function. Transcription is regulated using the strong CBH I gene promoter and terminator sequences for T. longibrachiatum. Between the CBHI promoter and terminator there are unique PmeI and SstI restriction sites that are used to insert the gene to be expressed. The T. longibrachiatum pyr4 selectable marker gene has been inserted into the CBHI terminator and the whole expression cassette (CBHI promoter-insertion sites-CBHI terminator-pyr4 gene-CBHI terminator) can be excised utilizing the unique NotI restriction site or the unique NotI and NheI restriction sites.

This vector is based on the bacterial vector, pSL1180 (Pharmacia Inc., Piscataway, N.J.), which is a PUC-type vector with an extended multiple cloning site. One skilled in the art would be able to construct this vector based on the flow diagram illustrated in FIG. 7. (See also U.S. patent application 07/954,113 filed Sep. 30, 1992 entitled "Stonewashing of Denim Garments Using Endoglucanase I & III" for the construction of PTEX expression plasmid.)

It would be possible to construct plasmids similar to PTEX-truncated cellulases or derivatives thereof described in the present invention containing any other piece of DNA sequence replacing the truncated cellulase gene.

Part 2. Cloning

The complete cbh2 gene used in the construction of the CBHII core domain expression plasmid, PTEX CBHII core, was obtained from the plasmid PUC219::CBHII (Korman, D. et al, 1990, Curr Genet 17:203–212). The cellulose binding domain, positioned at the 5' end of the cbh2 gene, is conveniently located between an XbaI and SnaBI restriction sites. In order to utilize the XbaI site an additional XbaI site in the polylinker was destroyed. PUC219::CBHII was partially digested with XbaI such that the majority of the product was linear. The XbaI overhangs were filled in using T4 DNA polymerase and ligated together under conditions favoring self ligation of the plasmid. This has the effect of destroying the blunted site which, in 50% of the plasmids, was the XbaI site in the polylinker. Such a plasmid was identified and digested with XbaI and SnaBI to release the cellulose binding domain. The vector-CBHII core domain was isolated and ligated with the following synthetic oligonucleotides designed to join the XbaI site with the SnaBI site at the signal peptidase cleavage site and papain cleavage point in the linker domain.

```
                                            (SEQ ID NO:42)
    XbaI                          SnaBI
5'  CTA GAG CGG TCG GGA ACC GCT AC 3'

3'      TC CTC GCC AGC CCT TGG CGA TG 5'
                                            (SEQ ID NO:43)
    Leu Glu Glu Arg Ser Gly Thr Ala Thr
```

The resultant plasmid, pUCACBD CBHII, was digested with NheI and the ends blunted by incubation with T4 DNA polymerase and dNTPs. After which the linear blunted plasmid DNA was digested with BglII and the Nhe (blunt)-BglII fragment containing the CBHII signal sequence and core domain was isolated.

The final expression plasmid was engineered by digesting the general purpose expression plasmid, pTEX (disclosed in 07/954,113, incorporated in its entirety by references, and described in Part 3 below), with SstII and PmeI and ligating the CBHII NheI (blunt)-BglII fragment from pUCACBD CBHII downstream of the cbhl promoter using a synthetic oligonucleotide having the sequence CGCTAG to fill in the BglII overhang with the SstII overhang. The construction of the resulting pTEC CBHIIcore expression vector is summarized in FIG. 9.

The pTEX-CBHI core expression plasmid was prepared in a similar manner as pTEX-CBHII core described in the above example. Its construction is exemplified in FIG. 8.

Part 3. Transformation and Expression

A large scale DNA prep was made of PTEX CBHII core and from this the NotI fragment containing the CBHII core domain under the control of the cbh1 transcriptional elements and pyr4 gene was isolated by preparative gel electrophoresis. The isolated fragment was transformed into the uridine auxotroph version of the quad deleted strain, 1A52 pyr13, and stable transformants were identified.

To select which transformants expressed cbh2 core domain genomic DNA was isolated from strains following growth on Vogels+1% glucose and Southern blot experiments performed using an isolated DNA fragment containing only the cbh2 core domain. Transformants were isolated having a copy of the cbh2 core domain expression cassette integrated into the genome of 1A52. Total mRNA was isolated from the two strains following growth for 1 day on Vogels+1k lactose. The mRNA was subjected to Northern analysis using the cbh2 coding region as a probe. Transformants expressing cbh2 core domain mRNA were identified.

Two transformants were grown under the same conditions as previously described in Example 1 in 14L fermentors. The resultant broth was concentrated and the proteins contained therein were separated by SDS polyacrylamide gel electrophoresis and the CBHII core domain protein identified by Western analysis. One transformant, #15, produced a protein of the correct size and reactivity to CBHII polyclonal antibodies.

It was subsequently estimated that the protein concentration of the fermentation supernatant after purification was 10 g/L of which 30–50% was CBHII core domain (See Example 4).

One may obtain any other novel truncated cellulase core domain protein or derivative thereof by employing the methods described above.

Example 4

Purification of CBHI and CBHII Catalytic Cores

Part 1. CBHI catalytic core

The CBHI core was purified from broth in the following manner. The CBHI core ultrafiltered (UF) broth was filtered using diatomaceous earth and diluted in 10 mM TES pH 6.8 to a conductivity of 1.5 mOhm. The diluted CBHI core was then loaded onto an anion exchange column (Q-Sepharose fast flow, Pharmacia cat # 17-0510-01) equilibrated in 10 mM TES pH 6.8. The CBHI core was separated from the majority of the other proteins in the broth using a gradient elution in 10 mM TES pH 6.8 from 0 to 1M NaCl. The fractions containing the CBHI core were then concentrated on an Amicon stirred cell concentrator with a PM 10 membrane (diaflo ultra filtration membranes, Amicon Cat # 13132MEM 5468A). This step concentrated the core, and additionally effected a separation of the core from lower molecular weight proteins. The resulting fractions were greater than 85% pure CBHI core. The purest fraction was sequence verified to be the CBHI core.

Part 2. CBHII catalytic core

It is predicted that CBHII catalytic core will purify in a manner similar to that of CBHII cellulase because of its similar biochemical properties. The theoretical pI of the CBHII core is less than half a pH unit lower than that of CBHII. Additionally, CBHII catalytic core is approximately 80% of the molecular weight of CBHII. Therefore, the following proposed purification protocol is based on the purification method used for CBHII. The diatomaceous earth treated, ultra filtered (UF) CBHII core broth is diluted into 10 mM TES pH 6.8 to a conductivity of <0.7 mOhm. The diluted CBHII core is then loaded onto an anion exchange column (Q-Sepharose fast flow, Pharmacia, cat # 17 0510-01) equilibrated in 10 mM TES pH 6.8. A salt gradient from 0 to 1M NaCl in 10 mM TES pH 6.8 is used to elute the CBHII core off the column. The fractions which contain the CBHII core is then buffer exchanged into 2 mM sodium succinate buffer and loaded onto a cation exchange column (SP-sephadex C-50). The CBHII core is next eluted from the column with a salt gradient from 0 to 100 mM NaCl.

Example 5

Stonewashing With Truncated Cellulase Enzyme

This example demonstrates that the use of truncated cellulase catalytic cores, and in particular truncated endoglucanase catalytic cores, surprisingly results in a reduced redeposition of dye onto a cellulose containing (denim) fabric during stonewashing at an equivalent level of abrasion to non-truncated cellulase. Further, the combination of truncated CBH-type catalytic core and non-truncated EG-type cellulase resulted in significantly improved backstaining characteristics when compared to non-truncated combinations at equivalent levels of abrasion. Denim is cotton cloth which has been dyed. Methods for imparting a stone washed appearance to denim fabrics are described in U.S. Pat. No. 4,832,864 and U.S. Ser. No. 07/954,113 which are incorporated herein by reference in its entirety.

Truncated cellulase catalytic cores and cellulase components were purified for use in this example as follows:

a) EGIII cellulase component was purified according to the method described in U.S. Pat. No. 5,328,841 which disclosure is incorporated herein by reference in its entirety.

b) truncated EGI catalytic cellulase core was purified by the method of Example 2.

c) truncated EGII catalytic cellulase core was purified by the method of Example 2.

d) truncated CBHI catalytic core was prepared according to the method of Example 4.

e) EGI cellulase component was purified for use in stonewashing applications in the following manner. The concentrated (UF) broth was diluted in 25 mM sodium acetate buffer pH 5.0 to a concentration of 7 mg/ml protein. 450 grams of avicel cellulose gel (FMC Bioproducts, Type PH-101) was added to the diluted broth and mixed at room temperature for thirty minutes. The avicel was removed from the broth by centrifugation resulting in an enriched EGI catalytic core.

f) EGII cellulase component was purified for use in stonewashing in the following manner. The concentrated (UF) broth was filtered through diatomaceous earth and buffer exchanged into citrate-phosphate pH 7, 0.4 mOhm using an ultrafiltration unit (Filtron Minisette Ultrafiltration Syustem, cat # FS018K01) with an Omega 10K Membrane (Filtron, cat. # FS010K75). This material was then loaded onto an anion exchange column (Q-sepharose fast flow, Pharmacia, cat. #17-0510-01) equilibrated in the above citrate-phosphate buffer. EGII was collected in the column flow through and fubber exchanged into sodium citrate pH 3.25, 0.5 mOhms using the ultrafiltration unit mentioned above. This material was then loaded onto a cation exchange column (SP-Spherodex LS, IBF Biotechnics, cat #262041). EGII was then eluted off the column in a linear gradient from pH 3.25 to 5.4. The fractions containing EGII were pooled and then used in stonewashing applications.

g) CBH I cellulase component was purified according to the method described in Example 15 of U.S. patent application Ser. No. 07/954,113.

These truncated cellulase catalytic core domains and cellulase components were tested alone or in combination for their ability to impart a stonewashed appearance to dyed denims. Specifically, the stonewashed denim fabrics were prepared using an industrial washer and dryer under the following conditions:

Citrate/phosphate buffer @ pH 5

38L total volume

120–135° F.

Six pair of denim pants with an equal weight of ballast 1 hour run time

15–30 ppm EGI, EGII, EGIII; 50 ppm CBH I and CBHI catalytic core; and 30–70 ppm EGI catalytic core and EGII catalytic core.

A detergent post wash included 90 grams of AATCC detergent without brighteners in the case of CBHI, CBHI catalytic core, EGIII plus CBHI and EGIII plus CBHI catalytic core.

The fabrics were evaluated for their stonewashed appearance (abrasion) and also for redeposition of dye onto the fabric by five panelists. The fabrics were graded using a scale consisting of denim swatches which have incrementally increasing levels of abrasion or redeposition. The scales are numerated from 1–10; 1 representing the jeans with the least amount of abrasion or redeposition (desize denim), and 10 representing a highly abraded or redeposited denim. The appearance of the treated jeans was directly compared to the denim swatches in the scale and give a number based on the swatch in the scale they most closely matched. The results of the evaluation are shown in FIGS. 10 and 11.

As shown in FIG. 10, truncated EGI catalytic core and truncated EGII catalytic core provide significant advantages over their un-modified, native state counterparts in abrasion and reduced redeposition.

As shown in FIG. 11, the addition of CBHI cellulase component to EGIII resulted in a slight enhancement of stonewashing but a large increase in backstaining (redeposition) of dye onto the fabric. However, the addition of truncated CBHI catalytic core to EGIII solution improved results in both increased abrasion and decreased redeposition. In fact, the addition of truncated CBHI catalytic core to EGIII cellulase decreased redeposition to a level below that of EGIII alone.

As these result show, the use of truncated cellulase core during treatment of cellulose containing fabrics surprisingly results in decreased backstaining while either maintaining an equivalent or superior level of abrasion. Further, this result is achieved either when the truncated cellulase is used alone, or when it is mixed with another wild-type or truncated cellulase. These results are both unexpected and surprising.

We claim:

1. A method of treating cellulose containing fabrics with cellulase comprising the steps of:
   (a) contacting said cellulose containing fabric with a treating composition comprising an effective amount of truncated cellulase wherein said truncated cellulase comprises a cellulase which lacks a cellulase binding domain; and
   (b) incubating said cellulose containing fabric in contact with said truncated cellulase under conditions effective to treat said fabric.

2. The method according to claim 1, wherein said treating composition further comprises EGIII.

3. The method according to claim 1, wherein said cellulose containing fabric comprises a cotton containing fabric.

4. The method according to claim 3, wherein said cotton containing fabric comprises dyed denim.

5. The method according to claim 1, wherein said treating composition comprises truncated cellulase or truncated cellulase derivative in a concentration of about 0.1 to about 1,000 ppm total protein.

6. The method according to claim 1, wherein said treating composition comprises truncated cellulase or truncated cellulase derivative in a concentration of about 0.2 to about 500 ppm.

7. The method according to claim 1, wherein said truncated cellulase is derived from a microorganism which is a fungus or bacteria.

8. The method according to claim 7, wherein said fungus is *Trichoderma sp.*

9. The method according to claim 8, wherein said *Trichoderma sp.* is *Trichoderma longibrachiatum*.

10. The method according to claim 1, wherein said treating method comprises stonewashing the cellulose containing fabric and said treating composition comprises a stonewashing composition.

11. The method according to claim 10, wherein said cellulose containing fabric is colored.

12. The method according to claim 11, wherein said colored fabric is dyed denim.

13. The method according to claim 10, comprising the additional step of treating said fabric with pumice simultaneously with, before or after said treating step.

14. The method according to claim 1, wherein said treating method comprises washing the cellulose containing fabric and said treating composition is a detergent composition comprising a surfactant.

15. The method according to claim 14, wherein said surfactant comprises nonionic ethoxylated alkyl phenols or nonionic ethoxylated alcohols.

16. A fabric produced by the process of claim 1.

17. A fabric produced by the process of claim 10.

18. A fabric produced by the process of claim 14.

19. The fabric of claim 16, wherein said fabric comprises dyed denim.

20. The method according to claim 1, wherein said truncated cellulase comprises a naturally occurring cellulase which lacks a cellulose binding domain.

21. The method according to claim 1, wherein said truncated cellulase comprises a cellulase from *Humicola insolens*.

22. A method of treating cellulose containing fabrics with cellulase comprising the steps of:
   a) contacting said cellulose containing fabric with a treating composition comprising an effective amount of truncated cellulase enzyme core; and
   b) incubating said cellulose containing fabric in contact with said truncated cellulase core under conditions effective to treat said fabric.

23. The method according to claim 22, wherein said truncated cellulase core is selected from the group consisting of EGI type core, EGII type core, EGV type core, CBHI type core, and CBHII type core.

24. The method according to claim 22, wherein said treating composition further comprises EGIII.

25. The method according to claim 22, wherein said cellulose containing fabric comprises a cotton containing fabric.

26. The method according to claim 25, wherein said cotton containing fabric comprises dyed denim.

27. The method according to claim 22, wherein said treating composition comprises said truncated cellulase core in a concentration of about 0.1 to about 1,000 ppm total protein.

28. The method according to claim 27, wherein said concentration is about 0.2 to about 500 ppm.

29. The method according to claim 22, wherein said truncated cellulase core is derived from a fungus or bacteria.

30. The method according to claim 29, wherein said fungus is a *Trichoderma sp.*

31. The method according to claim 30, wherein said *Trichoderma sp* is *Trichoderma longibrachiatum*.

32. The method according to claim 2, wherein said treating method comprises stonewashing the cellulose containing fabric and said treating composition comprises a stonewashing composition.

33. The method according to claim 32, wherein said tuncated cellulase core is present in a concentration of about 10 to about 400 ppm total protein.

34. The method according to claim 32, wherein said truncated cellulase core is present in a concentration of about 20 to about 100 ppm total protein.

35. The method according to claim 32, wherein said cellulose containing fabric is colored.

36. The method according to claim 35, wherein said colored fabric is dyed denim.

37. The method according to claim 32, further comprising treating said fabric with pumice simultaneously with, before or after said treating step.

38. The method according to claim 22, wherein said treating method comprises washing the cellulose containing fabric and said treating composition is a detergent composition comprising a surfactant.

39. The method according to claim 38, wherein said surfactant comprises nonionic ethoxylated alkyl phenols or nonionic ethoxylated alcohols.

40. The method according to claim 22, wherein said truncated cellulase core comprises a cellulase from *Humicola insolens*.

41. A fabric produced by the method of claim 22.

42. A fabric produced by the method of claim 32.

43. A fabric produced by the method of claim 38.

44. The fabric of claim 41, wherein said fabric comprises dyed denim.

45. The method according to claim 38, wherein said truncated cellulase core is selected from the group consisting of EGI type core, EGII type core, EGV type core, CBHI type core, and CBHII type core.

46. The method according to claim 38, wherein said truncated cellulase core is present in a concentration of about 0.1 to about 1000 ppm.

47. The method according to claim 38, wherein said truncated cellulase core is present in a concentration of about 0.2 to about 500 ppm.

48. A method of treating cellulose containing fabrics with cellulase comprising the steps of a) contacting said cellulose containing fabric with a treating composition comprising an effective amount of a truncated cellulase enzyme core selected from the group consisting of EGI type core, EGII type core, CBHI type core, CBHII type core, EGV type core and derivative type cores thereof and b) incubating said cellulose containing fabric in contact with said truncated cellulase core under conditions effective to treat said fabric.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:

(A) LENGTH: 93 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..96

(xi) SEQUENCE DESCRIPTION: SEQ ID NO: 1:

```
GGC CAG TGC GGC GGT ATT GGC TAC AGC GGC CCC ACG GTC TGC GCC AGC         48
Gly Gln Cys Gly Gly Ile Gly Tyr Ser Gly Pro Thr Val Cys Ala Ser
 1               5                  10                  15

GGC ACA ACT TGC CAG GTC CTG AAC CCT TAC TAC TCT CAG TGC CTG             93
Gly Thr Thr Cys Gln Val Leu Asn Pro Tyr Tyr Ser Gln Cys Leu
             20                  25                  30
```

(2) INFORMATION FOR SEQ ID NO: 2:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO: 2:

```
Gly Gln Cys Gly Gly Ile Gly Tyr Ser Gly Pro Thr Val Cys Ala Ser
 1               5                  10                  15

Gly Thr Thr Cys Gln Val Leu Asn Pro Tyr Tyr Ser Gln Cys Leu
             20                  25                  30
```

(2) INFORMATION FOR SEQ ID NO: 3:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..20, 70..166)

(xi) SEQUENCE DESCRIPTION: SEQ ID NO: 3:

```
CAA GCT TGC TCA AGC GTC   TG  GTAATTATGT GAACCCTCTC AAGAGACCCA          50
Gln Ala Cys Ser Ser Val   Trp
 1               5

AATACTGAGA TATGTCAAG G GGC CAA TGT GGT GGC CAG AAT TGG TCG GGT         100
                       Gly Gln Cys Gly Gly Gln Asn Trp Ser Gly
                                    10                  15

CCG ACT TGC TGT GCT TCC GGA AGC ACA TGC GTC TAC TCC AAC GAC TAT        148
Pro Thr Cys Cys Ala Ser Gly Ser Thr Cys Val Tyr Ser Asn Asp Tyr
             20                  25                  30

TAC TCC CAG TGT CTT CCC                                                166
Tyr Ser Gln Cys Leu Pro
         35
```

(2) INFORMATION FOR SEQ ID NO: 4:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO: 4:

Gln Ala Cys Ser Ser Val Trp Gly Gln Cys Gly Gly Gln Asn Trp Ser
 1               5                  10                  15

Gly Pro Thr Cys Cys Ala Ser Gly Ser Thr Cys Val Tyr Ser Asn Asp
                20                  25                  30

Tyr Tyr Ser Gln Cys Leu Pro
            35

(2) INFORMATION FOR SEQ ID NO: 5:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..82, 140..159)

(xi) SEQUENCE DESCRIPTION: SEQ ID NO: 5:

CAC TGG GGG CAG TGC GGT GGC ATT GGG TAC AGC GGG TGC AAG ACG TGC      48
His Trp Gly Gln Cys Gly Gly Ile Gly Tyr Ser Gly Cys Lys Thr Cys
 1               5                  10                  15

ACG TCG GGC ACT ACG TGC CAG TAT AGC AAC GAC   T GTTCGTATCC           92
Thr Ser Gly Thr Thr Cys Gln Tyr Ser Asn Asp
                20                  25

CCATGCCTGA CGGGAGTGAT TTTGAGATGC TAACCGCTAA AATACAG  AC TAC TCG     147
                                                    Tyr Tyr Ser
                                                            30

CAA TGC CTT                                                         156
Gln Cys Leu (2) INFORMATION FOR SEQ ID NO: 6:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO: 6:

His Trp Gly Gln Cys Gly Gly Ile Gly Tyr Ser Gly Cys Lys Thr Cys
 1               5                  10                  15

Thr Ser Gly Thr Thr Cys Gln Tyr Ser Asn Asp Tyr Tyr Ser Gln Cys
                20                  25                  30

Leu (2) INFORMATION FOR SEQ ID NO: 7:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS (B) LOCATION: 1..108

(xi) SEQUENCE DESCRIPTION: SEQ ID NO: 7:

| | | | | | | | | | | | | | | | | |
|---|---|---|---|---|---|---|---|---|---|---|---|---|---|---|---|---|
| CAG | CAG | ACT | GTC | TGG | GGC | CAG | TGT | GGA | GGT | ATT | GGT | TGG | AGC | GGA | CCT | 48 |
| Gln | Gln | Thr | Val | Trp | Gly | Gln | Cys | Gly | Gly | Ile | Gly | Trp | Ser | Gly | Pro | |
| 1 | | | | 5 | | | | | 10 | | | | | 15 | | |
| ACG | AAT | TGT | GCT | CCT | GGC | TCA | GCT | TGT | TCG | ACC | CTC | AAT | CCT | TAT | TAT | 96 |
| Thr | Asn | Cys | Ala | Pro | Gly | Ser | Ala | Cys | Ser | Thr | Leu | Asn | Pro | Tyr | Tyr | |
| | | | 20 | | | | | 25 | | | | | 30 | | | |
| GCG | CAA | TGT | ATT | | | | | | | | | | | | | 108 |
| Ala | Gln | Cys | Ile | | | | | | | | | | | | | |
| | | | 35 | | | | | | | | | | | | | |

(2) INFORMATION FOR SEQ ID NO: 8:

(i) SEQUENCE CHARACTERISTICS:
      (A) LENGTH: 36 amino acids
      (B) TYPE: amino acid
      (D) TOPOLOGY: linear (ii) MOLECULE TYPE: protein (xi) SEQUENCE DESCRIPTION: SEQ ID NO: 8:

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile
        35

(2) INFORMATION FOR SEQ ID NO: 9:

(i) SEQUENCE CHARACTERISTICS:
      (A) LENGTH: 1453 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: join(1..410, 478..1174, 1238..1453)

(xi) SEQUENCE DESCRIPTION: SEQ ID NO: 9:

| | | | | | | | | | | | | | | | | |
|---|---|---|---|---|---|---|---|---|---|---|---|---|---|---|---|---|
| CAG | TCG | GCC | TGC | ACT | CTC | CAA | TCG | GAG | ACT | CAC | CCG | CCT | CTG | ACA | TGG | 48 |
| Gln | Ser | Ala | Cys | Thr | Leu | Gln | Ser | Glu | Thr | His | Pro | Pro | Leu | Thr | Trp | |
| 1 | | | | 5 | | | | | 10 | | | | | 15 | | |
| CAG | AAA | TGC | TCG | TCT | GGT | GGC | ACT | TGC | ACT | CAA | CAG | ACA | GGC | TCC | GTG | 96 |
| Gln | Lys | Cys | Ser | Ser | Gly | Gly | Thr | Cys | Thr | Gln | Gln | Thr | Gly | Ser | Val | |
| | | | 20 | | | | | 25 | | | | | 30 | | | |
| GTC | ATC | GAC | GCC | AAC | TGG | CGC | TGG | ACT | CAC | GCT | ACG | AAC | AGC | AGC | ACG | 144 |
| Val | Ile | Asp | Ala | Asn | Trp | Arg | Trp | Thr | His | Ala | Thr | Asn | Ser | Ser | Thr | |
| | | | 35 | | | | | 40 | | | | | 45 | | | |
| AAC | TGC | TAC | GAT | GGC | AAC | ACT | TGG | AGC | TCG | ACC | CTA | TGT | CCT | GAC | AAC | 192 |
| Asn | Cys | Tyr | Asp | Gly | Asn | Thr | Trp | Ser | Ser | Thr | Leu | Cys | Pro | Asp | Asn | |
| | | | 50 | | | | | 55 | | | | | 60 | | | |
| GAG | ACC | TGC | GCG | AAG | AAC | TGC | TGT | CTG | GAC | GGT | GCC | GCC | TAC | GCG | TCC | 240 |
| Glu | Thr | Cys | Ala | Lys | Asn | Cys | Cys | Leu | Asp | Gly | Ala | Ala | Tyr | Ala | Ser | |
| 65 | | | | 70 | | | | | 75 | | | | | | 80 | |
| ACG | TAC | GGA | GTT | ACC | ACG | AGC | GGT | AAC | AGC | CTC | TCC | ATT | GGC | TTT | GTC | 288 |
| Thr | Tyr | Gly | Val | Thr | Thr | Ser | Gly | Asn | Ser | Leu | Ser | Ile | Gly | Phe | Val | |
| | | | | 85 | | | | | 90 | | | | | 95 | | |
| ACC | CAG | TCT | GCG | CAG | AAG | AAC | GTT | GGC | GCT | CGC | CTT | TAC | CTT | ATG | GCG | 336 |

-continued

```
Thr Gln Ser Ala Gln Lys Asn Val Gly Ala Arg Leu Tyr Leu Met Ala
            100                 105                 110
AGC GAC ACG ACC TAC CAG GAA TTC ACC CTG CTT GGC AAC GAG TTC TCT      384
Ser Asp Thr Thr Tyr Gln Glu Phe Thr Leu Leu Gly Asn Glu Phe Ser
            115                 120                 125

TTC GAT GTT GAT GTT TCG CAG CTG  CC GTAAGTGACT TACCATGAAC            430
Phe Asp Val Asp Val Ser Gln Leu  Pro
130                     135

CCCTGACGTA TCTTCTTGTG GGCTCCCAGC TGACTGGCCA ATTTAAG G TGC GGC        484
                                                    Cys Gly

TTG AAC GGA GCT CTC TAC TTC GTG TCC ATG GAC GCG GAT GGT GGC GTG      532
Leu Asn Gly Ala Leu Tyr Phe Val Ser Met Asp Ala Asp Gly Gly Val
140                     145                 150                 155

AGC AAG TAT CCC ACC AAC ACC GCT GGC GCC AAG TAC GGC ACG GGG TAC      580
Ser Lys Tyr Pro Thr Asn Thr Ala Gly Ala Lys Tyr Gly Thr Gly Tyr
                160                 165                 170

TGT GAC AGC CAG TGT CCC CGC GAT CTG AAG TTC ATC AAT GGC CAG GCC      628
Cys Asp Ser Gln Cys Pro Arg Asp Leu Lys Phe Ile Asn Gly Gln Ala
            175                 180                 185

AAC GTT GAG GGC TGG GAG CCG TCA TCC AAC AAC GCA AAC ACG GGC ATT      676
Asn Val Glu Gly Trp Glu Pro Ser Ser Asn Asn Ala Asn Thr Gly Ile
            190                 195                 200

GGA GGA CAC GGA AGC TGC TGC TCT GAG ATG GAT ATC TGG GAG GCC AAC      724
Gly Gly His Gly Ser Cys Cys Ser Glu Met Asp Ile Trp Glu Ala Asn
            205                 210                 215

TCC ATC TCC GAG GCT CTT ACC CCC CAC CCT TGC ACG ACT GTC GGC CAG      772
Ser Ile Ser Glu Ala Leu Thr Pro His Pro Cys Thr Thr Val Gly Gln
220                 225                 230                 235

GAG ATC TGC GAG GGT GAT GGG TGC GGC GGA ACT TAC TCC GAT AAC AGA      820
Glu Ile Cys Glu Gly Asp Gly Cys Gly Gly Thr Tyr Ser Asp Asn Arg
                240                 245                 250

TAT GGC GGC ACT TGC GAT CCC GAT GGC TGC GAC TGG AAC CCA TAC CGC      868
Tyr Gly Gly Thr Cys Asp Pro Asp Gly Cys Asp Trp Asn Pro Tyr Arg
            255                 260                 265

CTG GGC AAC ACC AGC TTC TAC GGC CCT GGC TCA AGC TTT ACC CTC GAT      916
Leu Gly Asn Thr Ser Phe Tyr Gly Pro Gly Ser Ser Phe Thr Leu Asp
            270                 275                 280

ACC ACC AAG AAA TTG ACC GTT GTC ACC CAG TTC GAG ACG TCG GGT GCC      964
Thr Thr Lys Lys Leu Thr Val Val Thr Gln Phe Glu Thr Ser Gly Ala
            285                 290                 295

ATC AAC CGA TAC TAT GTC CAG AAT GGC GTC ACT TTC CAG CAG CCC AAC     1012
Ile Asn Arg Tyr Tyr Val Gln Asn Gly Val Thr Phe Gln Gln Pro Asn
300                 305                 310                 315

GCC GAG CTT GGT AGT TAC TCT GGC AAC GAG CTC AAC GAT GAT TAC TGC     1060
Ala Glu Leu Gly Ser Tyr Ser Gly Asn Glu Leu Asn Asp Asp Tyr Cys
                320                 325                 330

ACA GCT GAG GAG GCA GAA TTC GGC GGA TCC TCT TTC TCA GAC AAG GGC     1108
Thr Ala Glu Glu Ala Glu Phe Gly Gly Ser Ser Phe Ser Asp Lys Gly
            335                 340                 345

GGC CTG ACT CAG TTC AAG AAG GCT ACC TCT GGC GGC ATG GTT CTG GTC     1156
Gly Leu Thr Gln Phe Lys Lys Ala Thr Ser Gly Gly Met Val Leu Val
            350                 355                 360

ATG AGT CTG TGG GAT GAT GTGAGTTTGA TGGACAAACA TGCGCGTTGA            1204
Met Ser Leu Trp Asp Asp
            365

CAAAGAGTCA AGCAGCTGAC TGAGATGTTA CAG TAC TAC GCC AAC ATG CTG TGG    1258
                                    Tyr Tyr Ala Asn Met Leu Trp
                                            370                 375

CTG GAC TCC ACC TAC CCG ACA AAC GAG ACC TCC TCC ACA CCC GGT GCC     1306
```

```
Leu Asp Ser Thr Tyr Pro Thr Asn Glu Thr Ser Ser Thr Pro Gly Ala
            380                 385                 390

GTG CGC GGA AGC TGC TCC ACC AGC TCC GGT GTC CCT GCT CAG GTC GAA    1354
Val Arg Gly Ser Cys Ser Thr Ser Ser Gly Val Pro Ala Gln Val Glu
            395                 400                 405

TCT CAG TCT CCC AAC GCC AAG GTC ACC TTC TCC AAC ATC AAG TTC GGA    1402
Ser Gln Ser Pro Asn Ala Lys Val Thr Phe Ser Asn Ile Lys Phe Gly
            410                 415                 420

CCC ATT GGC AGC ACC GGC AAC CCT AGC GGC GGC AAC CCT CCC GGC GGA    1450
Pro Ile Gly Ser Thr Gly Asn Pro Ser Gly Gly Asn Pro Pro Gly Gly
425             430                 435                 440

AAC                                                                1453
Asn
```

(2) INFORMATION FOR SEQ ID NO: 10:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO: 10:

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65              70                  75                  80

Thr Tyr Gly Val Thr Thr Ser Gly Asn Ser Leu Ser Ile Gly Phe Val
            85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
            115                 120                 125

Phe Asp Val Asp Val Ser Gln Leu Pro Cys Gly Leu Asn Gly Ala Leu
130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
            195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
```

```
                    260                 265                 270
      Phe Tyr Gly Pro Gly Ser Ser Phe Thr Leu Asp Thr Thr Lys Lys Leu
                      275                 280                 285

Thr Val Val Thr Gln Phe Glu Thr Ser Gly Ala Ile Asn Arg Tyr Tyr
              290                 295                 300

Val Gln Asn Gly Val Thr Phe Gln Gln Pro Asn Ala Glu Leu Gly Ser
      305                 310                 315                 320

Tyr Ser Gly Asn Glu Leu Asn Asp Asp Tyr Cys Thr Ala Glu Glu Ala
                      325                 330                 335

Glu Phe Gly Gly Ser Ser Phe Ser Asp Lys Gly Gly Leu Thr Gln Phe
                      340                 345                 350

Lys Lys Ala Thr Ser Gly Gly Met Val Leu Val Met Ser Leu Trp Asp
                      355                 360                 365

Asp Tyr Tyr Ala Asn Met Leu Trp Leu Asp Ser Thr Tyr Pro Thr Asn
              370                 375                 380

Glu Thr Ser Ser Thr Pro Gly Ala Val Arg Gly Ser Cys Ser Thr Ser
      385                 390                 395                 400

Ser Gly Val Pro Ala Gln Val Glu Ser Gln Ser Pro Asn Ala Lys Val
                      405                 410                 415

Thr Phe Ser Asn Ile Lys Phe Gly Pro Ile Gly Ser Thr Gly Asn Pro
                      420                 425                 430

Ser Gly Gly Asn Pro Pro Gly Gly Asn
                      435                 440

(2) INFORMATION FOR SEQ ID NO: 11:

(i) SEQUENCE CHARACTERISTICS:
        (A) LENGTH: 1241 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..161, 218..465, 556..1244)

(xi) SEQUENCE DESCRIPTION: SEQ ID NO: 11:

TCG GGA ACC GCT ACG TAT TCA GGC AAC CCT TTT GTT GGG GTC ACT CCT        48
Ser Gly Thr Ala Thr Tyr Ser Gly Asn Pro Phe Val Gly Val Thr Pro
  1               5                  10                  15

TGG GCC AAT GCA TAT TAC GCC TCT GAA GTT AGC AGC CTC GCT ATT CCT        96
Trp Ala Asn Ala Tyr Tyr Ala Ser Glu Val Ser Ser Leu Ala Ile Pro
             20                  25                  30

AGC TTG ACT GGA GCC ATG GCC ACT GCT GCA GCA GCT GTC GCA AAG GTT       144
Ser Leu Thr Gly Ala Met Ala Thr Ala Ala Ala Ala Val Ala Lys Val
         35                  40                  45

CCC TCT TTT ATG TGG  CT   GTAGGTCCTC CCGGAACCAA GGCAATCTGT            191
Pro Ser Phe Met Trp  Leu
     50

TACTGAAGGC TCATCATTCA CTGCAG A GAT ACT CTT GAC AAG ACC CCT CTC        242
                            Asp Thr Leu Asp Lys Thr Pro Leu
                             55                  60

ATG GAG CAA ACC TTG GCC GAC ATC CGC ACC GCC AAC AAG AAT GGC GGT       290
Met Glu Gln Thr Leu Ala Asp Ile Arg Thr Ala Asn Lys Asn Gly Gly
     65                  70                  75

AAC TAT GCC GGA CAG TTT GTG GTG ATA GAC TTG CCG GAT CGC GAT TGC       338
Asn Tyr Ala Gly Gln Phe Val Val Ile Asp Leu Pro Asp Arg Asp Cys
     80                  85                  90
```

```
GCT GCC CTT GCC TCG AAT GGC GAA TAC TCT ATT GCC GAT GGT GGC GTC      386
Ala Ala Leu Ala Ser Asn Gly Glu Tyr Ser Ile Ala Asp Gly Gly Val
 95             100                 105                 110

GCC AAA TAT AAG AAC TAT ATC GAC ACC ATT CGT CAA ATT GTC GTG GAA      434
Ala Lys Tyr Lys Asn Tyr Ile Asp Thr Ile Arg Gln Ile Val Val Glu
                115                 120                 125

TAT TCC GAT ATC CGG ACC CTC CTG GTT ATT    G GTATGAGTTT AAACACCTGC   485
Tyr Ser Asp Ile Arg Thr Leu Leu Val Ile
            130                 135

CTCCCCCCCC CCTTCCCTTC CTTTCCCGCC GGCATCTTGT CGTTGTGCTA ACTATTGTTC    545

CCTCTTCCAG AG CCT GAC TCT CTT GCC AAC CTG GTG ACC AAC CTC GGT       593
              Glu Pro Asp Ser Leu Ala Asn Leu Val Thr Asn Leu Gly
                                 140                 145

ACT CCA AAG TGT GCC AAT GCT CAG TCA GCC TAC CTT GAG TGC ATC AAC      641
Thr Pro Lys Cys Ala Asn Ala Gln Ser Ala Tyr Leu Glu Cys Ile Asn
150             155                 160                 165

TAC GCC GTC ACA CAG CTG AAC CTT CCA AAT GTT GCG ATG TAT TTG GAC      689
Tyr Ala Val Thr Gln Leu Asn Leu Pro Asn Val Ala Met Tyr Leu Asp
                170                 175                 180

GCT GGC CAT GCA GGA TGG CTT GGC TGG CCG GCA AAC CAA GAC CCG GCC      737
Ala Gly His Ala Gly Trp Leu Gly Trp Pro Ala Asn Gln Asp Pro Ala
                185                 190                 195

GCT CAG CTA TTT GCA AAT GTT TAC AAG AAT GCA TCG TCT CCG AGA GCT      785
Ala Gln Leu Phe Ala Asn Val Tyr Lys Asn Ala Ser Ser Pro Arg Ala
                200                 205                 210

CTT CGC GGA TTG GCA ACC AAT GTC GCC AAC TAC AAC GGG TGG AAC ATT      833
Leu Arg Gly Leu Ala Thr Asn Val Ala Asn Tyr Asn Gly Trp Asn Ile
            215                 220                 225

ACC AGC CCC CCA TCG TAC ACG CAA GGC AAC GCT GTC TAC AAC GAG AAG      881
Thr Ser Pro Pro Ser Tyr Thr Gln Gly Asn Ala Val Tyr Asn Glu Lys
230             235                 240                 245

CTG TAC ATC CAC GCT ATT GGA CCT CTT CTT GCC AAT CAC GGC TGG TCC      929
Leu Tyr Ile His Ala Ile Gly Pro Leu Leu Ala Asn His Gly Trp Ser
                250                 255                 260

AAC GCC TTC TTC ATC ACT GAT CAA GGT CGA TCG GGA AAG CAG CCT ACC      977
Asn Ala Phe Phe Ile Thr Asp Gln Gly Arg Ser Gly Lys Gln Pro Thr
                265                 270                 275

GGA CAG CAA CAG TGG GGA GAC TGG TGC AAT GTG ATC GGC ACC GGA TTT     1025
Gly Gln Gln Gln Trp Gly Asp Trp Cys Asn Val Ile Gly Thr Gly Phe
            280                 285                 290

GGT ATT CGC CCA TCC GCA AAC ACT GGG GAC TCG TTG CTG GAT TCG TTT     1073
Gly Ile Arg Pro Ser Ala Asn Thr Gly Asp Ser Leu Leu Asp Ser Phe
295             300                 305

GTC TGG GTC AAG CCA GGC GGC GAG TGT GAC GGC ACC AGC GAC AGC AGT     1121
Val Trp Val Lys Pro Gly Gly Glu Cys Asp Gly Thr Ser Asp Ser Ser
310             315                 320                 325

GCG CCA CGA TTT GAC TCC CAC TGT GCG CTC CCA GAT GCC TTG CAA CCG     1169
Ala Pro Arg Phe Asp Ser His Cys Ala Leu Pro Asp Ala Leu Gln Pro
                330                 335                 340

GCG CCT CAA GCT GGT GCT TGG TTC CAA GCC TAC TTT GTG CAG CTT CTC     1217
Ala Pro Gln Ala Gly Ala Trp Phe Gln Ala Tyr Phe Val Gln Leu Leu
            345                 350                 355

ACA AAC GCA AAC CCA TCG TTC CTG                                     1241
Thr Asn Ala Asn Pro Ser Phe Leu
            360                 365
```

(2) INFORMATION FOR SEQ ID NO: 12:

(i) SEQUENCE CHARACTERISTICS:

(A) LENGTH: 365 amino acids
(B) TYPE: amino acid
(D) TOPOLOGY: linear (ii) MOLECULE TYPE: protein (xi) SEQUENCE DESCRIPTION: SEQ ID NO: 12:

```
Ser Gly Thr Ala Thr Tyr Ser Gly Asn Pro Phe Val Gly Val Thr Pro
 1               5                  10                  15
Trp Ala Asn Ala Tyr Tyr Ala Ser Glu Val Ser Ser Leu Ala Ile Pro
                20                  25                  30
Ser Leu Thr Gly Ala Met Ala Thr Ala Ala Ala Ala Val Ala Lys Val
            35                  40                  45
Pro Ser Phe Met Trp Leu Asp Thr Leu Asp Lys Thr Pro Leu Met Glu
 50                  55                  60
Gln Thr Leu Ala Asp Ile Arg Thr Ala Asn Lys Asn Gly Gly Asn Tyr
 65                  70                  75                  80
Ala Gly Gln Phe Val Val Ile Asp Leu Pro Asp Arg Asp Cys Ala Ala
                85                  90                  95
Leu Ala Ser Asn Gly Glu Tyr Ser Ile Ala Asp Gly Gly Val Ala Lys
                100                 105                 110
Tyr Lys Asn Tyr Ile Asp Thr Ile Arg Gln Ile Val Val Glu Tyr Ser
            115                 120                 125
Asp Ile Arg Thr Leu Leu Val Ile Glu Pro Asp Ser Leu Ala Asn Leu
130                 135                 140
Val Thr Asn Leu Gly Thr Pro Lys Cys Ala Asn Ala Gln Ser Ala Tyr
145                 150                 155                 160
Leu Glu Cys Ile Asn Tyr Ala Val Thr Gln Leu Asn Leu Pro Asn Val
                165                 170                 175
Ala Met Tyr Leu Asp Ala Gly His Ala Gly Trp Leu Gly Trp Pro Ala
            180                 185                 190
Asn Gln Asp Pro Ala Ala Gln Leu Phe Ala Asn Val Tyr Lys Asn Ala
                195                 200                 205
Ser Ser Pro Arg Ala Leu Arg Gly Leu Ala Thr Asn Val Ala Asn Tyr
210                 215                 220
Asn Gly Trp Asn Ile Thr Ser Pro Pro Ser Tyr Thr Gln Gly Asn Ala
225                 230                 235                 240
Val Tyr Asn Glu Lys Leu Tyr Ile His Ala Ile Gly Pro Leu Leu Ala
                245                 250                 255
Asn His Gly Trp Ser Asn Ala Phe Phe Ile Thr Asp Gln Gly Arg Ser
            260                 265                 270
Gly Lys Gln Pro Thr Gly Gln Gln Gln Trp Gly Asp Trp Cys Asn Val
            275                 280                 285
Ile Gly Thr Gly Phe Gly Ile Arg Pro Ser Ala Asn Thr Gly Asp Ser
290                 295                 300
Leu Leu Asp Ser Phe Val Trp Val Lys Pro Gly Gly Glu Cys Asp Gly
305                 310                 315                 320
Thr Ser Asp Ser Ser Ala Pro Arg Phe Asp Ser His Cys Ala Leu Pro
                325                 330                 335
Asp Ala Leu Gln Pro Ala Pro Gln Ala Gly Ala Trp Phe Gln Ala Tyr
            340                 345                 350
Phe Val Gln Leu Leu Thr Asn Ala Asn Pro Ser Phe Leu
            355                 360                 365
```

(2) INFORMATION FOR SEQ ID NO: 13:

(i) SEQUENCE CHARACTERISTICS:
   (A) LENGTH: 1201 base pairs
   (B) TYPE: nucleic acid
   (C) STRANDEDNESS: single
   (D) TOPOLOGY: linear (ii) MOLECULE TYPE: DNA (genomic)

(ix) FEATURE:
   (A) NAME/KEY: CDS
   (B) LOCATION: join(1..704, 775..1201)

(xi) SEQUENCE DESCRIPTION: SEQ ID NO: 13:

```
CAG CAA CCG GGT ACC AGC ACC CCC GAG GTC CAT CCC AAG TTG ACA ACC        48
Gln Gln Pro Gly Thr Ser Thr Pro Glu Val His Pro Lys Leu Thr Thr
 1               5                  10                  15

TAC AAG TGT ACA AAG TCC GGG GGG TGC GTG GCC CAG GAC ACC TCG GTG        96
Tyr Lys Cys Thr Lys Ser Gly Gly Cys Val Ala Gln Asp Thr Ser Val
                20                  25                  30

GTC CTT GAC TGG AAC TAC CGC TGG ATG CAC GAC GCA AAC TAC AAC TCG       144
Val Leu Asp Trp Asn Tyr Arg Trp Met His Asp Ala Asn Tyr Asn Ser
         35                  40                  45

TGC ACC GTC AAC GGC GGC GTC AAC ACC ACG CTC TGC CCT GAC GAG GCG       192
Cys Thr Val Asn Gly Gly Val Asn Thr Thr Leu Cys Pro Asp Glu Ala
 50                  55                  60

ACC TGT GGC AAG AAC TGC TTC ATC GAG GGC GTC GAC TAC GCC GCC TCG       240
Thr Cys Gly Lys Asn Cys Phe Ile Glu Gly Val Asp Tyr Ala Ala Ser
 65                  70                  75                  80

GGC GTC ACG ACC TCG GGC AGC AGC CTC ACC ATG AAC CAG TAC ATG CCC       288
Gly Val Thr Thr Ser Gly Ser Ser Leu Thr Met Asn Gln Tyr Met Pro
                 85                  90                  95

AGC AGC TCT GGC GGC TAC AGC AGC GTC TCT CCT CGG CTG TAT CTC CTG       336
Ser Ser Ser Gly Gly Tyr Ser Ser Val Ser Pro Arg Leu Tyr Leu Leu
                100                 105                 110

GAC TCT GAC GGT GAG TAC GTG ATG CTG AAG CTC AAC GGC CAG GAG CTG       384
Asp Ser Asp Gly Glu Tyr Val Met Leu Lys Leu Asn Gly Gln Glu Leu
            115                 120                 125

AGC TTC GAC GTC GAC CTC TCT GCT CTG CCG TGT GGA GAG AAC GGC TCG       432
Ser Phe Asp Val Asp Leu Ser Ala Leu Pro Cys Gly Glu Asn Gly Ser
        130                 135                 140

CTC TAC CTG TCT CAG ATG GAC GAG AAC GGG GGC GCC AAC CAG TAT AAC       480
Leu Tyr Leu Ser Gln Met Asp Glu Asn Gly Gly Ala Asn Gln Tyr Asn
145                 150                 155                 160

ACG GCC GGT GCC AAC TAC GGG AGC GGC TAC TGC GAT GCT CAG TGC CCC       528
Thr Ala Gly Ala Asn Tyr Gly Ser Gly Tyr Cys Asp Ala Gln Cys Pro
                165                 170                 175

GTC CAG ACA TGG AGG AAC GGC ACC CTC AAC ACT AGC CAC CAG GGC TTC       576
Val Gln Thr Trp Arg Asn Gly Thr Leu Asn Thr Ser His Gln Gly Phe
            180                 185                 190

TGC TGC AAC GAG ATG GAT ATC CTG GAG GGC AAC TCG AGG GCG AAT GCC       624
Cys Cys Asn Glu Met Asp Ile Leu Glu Gly Asn Ser Arg Ala Asn Ala
        195                 200                 205

TTG ACC CCT CAC TCT TGC ACG GCC ACG GCC TGC GAC TCT GCC GGT TGC       672
Leu Thr Pro His Ser Cys Thr Ala Thr Ala Cys Asp Ser Ala Gly Cys
    210                 215                 220

GGC TTC AAC CCC TAT GGC AGC GGC TAC AAA  AG GTGAGCCTGA                714
Gly Phe Asn Pro Tyr Gly Ser Gly Tyr Lys  Ser
225                 230                 235

TGCCACTACT ACCCCTTTCC TGGCGCTCTC GCGGTTTTCC ATGCTGACAT GGTTTTCCAG     774

C TAC TAC GGC CCC GGA GAT ACC GTT GAC ACC TCC AAG ACC TTC ACC         820
  Tyr Tyr Gly Pro Gly Asp Thr Val Asp Thr Ser Lys Thr Phe Thr
```

|  |  |  |  |  |  |  |  |  |  |  |  |  |  |
|---|---|---|---|---|---|---|---|---|---|---|---|---|---|
|  |  |  | 240 |  |  |  | 245 |  |  |  | 250 |  |  |
| ATC | ATC | ACC | CAG | TTC | AAC | ACG | GAC | AAC | GGC | TCG | CCC | TCG | GGC | AAC | CTT | 868 |
| Ile | Ile | Thr | Gln | Phe | Asn | Thr | Asp | Asn | Gly | Ser | Pro | Ser | Gly | Asn | Leu |  |
|  |  |  | 255 |  |  |  | 260 |  |  |  | 265 |  |  |
| GTG | AGC | ATC | ACC | CGC | AAG | TAC | CAG | CAA | AAC | GGC | GTC | GAC | ATC | CCC | AGC | 916 |
| Val | Ser | Ile | Thr | Arg | Lys | Tyr | Gln | Gln | Asn | Gly | Val | Asp | Ile | Pro | Ser |  |
|  |  |  | 270 |  |  |  | 275 |  |  |  | 280 |  |  |
| GCC | CAG | CCC | GGC | GGC | GAC | ACC | ATC | TCG | TCC | TGC | CCG | TCC | GCC | TCA | GCC | 964 |
| Ala | Gln | Pro | Gly | Gly | Asp | Thr | Ile | Ser | Ser | Cys | Pro | Ser | Ala | Ser | Ala |  |
|  |  |  | 285 |  |  |  | 290 |  |  |  | 295 |  |  |
| TAC | GGC | GGC | CTC | GCC | ACC | ATG | GGC | AAG | GCC | CTG | AGC | AGC | GGC | ATG | GTG | 1012 |
| Tyr | Gly | Gly | Leu | Ala | Thr | Met | Gly | Lys | Ala | Leu | Ser | Ser | Gly | Met | Val |  |
|  |  |  | 300 |  |  |  | 305 |  |  |  | 310 |  |  |
| CTC | GTG | TTC | AGC | ATT | TGG | AAC | GAC | AAC | AGC | CAG | TAC | ATG | AAC | TGG | CTC | 1060 |
| Leu | Val | Phe | Ser | Ile | Trp | Asn | Asp | Asn | Ser | Gln | Tyr | Met | Asn | Trp | Leu |  |
| 315 |  |  |  |  | 320 |  |  |  | 325 |  |  |  |  | 330 |  |
| GAC | AGC | GGC | AAC | GCC | GGC | CCC | TGC | AGC | AGC | ACC | GAG | GGC | AAC | CCA | TCC | 1108 |
| Asp | Ser | Gly | Asn | Ala | Gly | Pro | Cys | Ser | Ser | Thr | Glu | Gly | Asn | Pro | Ser |  |
|  |  |  | 335 |  |  |  | 340 |  |  |  | 345 |  |  |
| AAC | ATC | CTG | GCC | AAC | AAC | CCC | AAC | ACG | CAC | GTC | GTC | TTC | TCC | AAC | ATC | 1156 |
| Asn | Ile | Leu | Ala | Asn | Asn | Pro | Asn | Thr | His | Val | Val | Phe | Ser | Asn | Ile |  |
|  |  |  | 350 |  |  |  | 355 |  |  |  | 360 |  |  |
| CGC | TGG | GGA | GAC | ATT | GGG | TCT | ACT | ACG | AAC | TCG | ACT | GCG | CCC | CCG |  | 1201 |
| Arg | Trp | Gly | Asp | Ile | Gly | Ser | Thr | Thr | Asn | Ser | Thr | Ala | Pro | Pro |  |  |
|  |  |  | 365 |  |  |  | 370 |  |  |  | 375 |  |  |

(2) INFORMATION FOR SEQ ID NO: 14:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO: 14:

```
Gln Gln Pro Gly Thr Ser Thr Pro Glu Val His Pro Lys Leu Thr Thr
  1               5                  10                  15

Tyr Lys Cys Thr Lys Ser Gly Gly Cys Val Ala Gln Asp Thr Ser Val
             20                  25                  30

Val Leu Asp Trp Asn Tyr Arg Trp Met His Asp Ala Asn Tyr Asn Ser
         35                  40                  45

Cys Thr Val Asn Gly Gly Val Asn Thr Thr Leu Cys Pro Asp Glu Ala
     50                  55                  60

Thr Cys Gly Lys Asn Cys Phe Ile Glu Gly Val Asp Tyr Ala Ala Ser
 65                  70                  75                  80

Gly Val Thr Thr Ser Gly Ser Ser Leu Thr Met Asn Gln Tyr Met Pro
                 85                  90                  95

Ser Ser Ser Gly Gly Tyr Ser Ser Val Ser Pro Arg Leu Tyr Leu Leu
            100                 105                 110

Asp Ser Asp Gly Glu Tyr Val Met Leu Lys Leu Asn Gly Gln Glu Leu
        115                 120                 125

Ser Phe Asp Val Asp Leu Ser Ala Leu Pro Cys Gly Glu Asn Gly Ser
    130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175
```

-continued

```
Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205

Leu Thr Pro His Ser Cys Thr Ala Thr Ala Cys Asp Ser Ala Gly Cys
    210                 215                 220

Gly Phe Asn Pro Tyr Gly Ser Gly Tyr Lys Ser Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
    290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                325                 330                 335

Pro Cys Ser Ser Thr Glu Gly Asn Pro Ser Asn Ile Leu Ala Asn Asn
            340                 345                 350

Pro Asn Thr His Val Val Phe Ser Asn Ile Arg Trp Gly Asp Ile Gly
        355                 360                 365

Ser Thr Thr Asn Ser Thr Ala Pro Pro
    370                 375
```

(2) INFORMATION FOR SEQ ID NO: 15:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..56, 231..1158)

(xi) SEQUENCE DESCRIPTION: SEQ ID NO: 15:

```
GGG GTC CGA TTT GCC GGC GTT AAC ATC GCG GGT TTT GAC TTT GGC TGT      48
Gly Val Arg Phe Ala Gly Val Asn Ile Ala Gly Phe Asp Phe Gly Cys
  1               5                  10                  15

ACC ACA GA  GTGAGTACCC TTGTTTCCTG GTGTTGCTGG CTGGTTGGGC              96
Thr Thr Asp

GGGTATACAG CGAAGCGGAC GCAAGAACAC CGCCGGTCCG CCACCATCAA GATGTGGGTG   156

GTAAGCGGCG GTGTTTTGTA CAACTACCTG ACAGCTCACT CAGGAAATGA GAATTAATGG   216

AAGTCTTGTT ACAG T GGC ACT TGC GTT ACC TCG AAG GTT TAT CCT CCG       264
              Gly Thr Cys Val Thr Ser Lys Val Tyr Pro Pro
                  20                  25                  30

TTG AAG AAC TTC ACC GGC TCA AAC AAC TAC CCC GAT GGC ATC GGC CAG     312
Leu Lys Asn Phe Thr Gly Ser Asn Asn Tyr Pro Asp Gly Ile Gly Gln
              35                  40                  45

ATG CAG CAC TTC GTC AAC GAG GAC GGG ATG ACT ATT TTC CGC TTA CCT     360
Met Gln His Phe Val Asn Glu Asp Gly Met Thr Ile Phe Arg Leu Pro
          50                  55                  60
```

```
GTC GGA TGG CAG TAC CTC GTC AAC AAC AAT TTG GGC GGC AAT CTT GAT        408
Val Gly Trp Gln Tyr Leu Val Asn Asn Asn Leu Gly Gly Asn Leu Asp
             65                  70                  75

TCC ACG AGC ATT TCC AAG TAT GAT CAG CTT GTT CAG GGG TGC CTG TCT        456
Ser Thr Ser Ile Ser Lys Tyr Asp Gln Leu Val Gln Gly Cys Leu Ser
 80                  85                  90

CTG GGC GCA TAC TGC ATC GTC GAC ATC CAC AAT TAT GCT CGA TGG AAC        504
Leu Gly Ala Tyr Cys Ile Val Asp Ile His Asn Tyr Ala Arg Trp Asn
 95                 100                 105                 110

GGT GGG ATC ATT GGT CAG GGC GGC CCT ACT AAT GCT CAA TTC ACG AGC        552
Gly Gly Ile Ile Gly Gln Gly Gly Pro Thr Asn Ala Gln Phe Thr Ser
                115                 120                 125

CTT TGG TCG CAG TTG GCA TCA AAG TAC GCA TCT CAG TCG AGG GTG TGG        600
Leu Trp Ser Gln Leu Ala Ser Lys Tyr Ala Ser Gln Ser Arg Val Trp
            130                 135                 140

TTC GGC ATC ATG AAT GAG CCC CAC GAC GTG AAC ATC AAC ACC TGG GCT        648
Phe Gly Ile Met Asn Glu Pro His Asp Val Asn Ile Asn Thr Trp Ala
            145                 150                 155

GCC ACG GTC CAA GAG GTT GTA ACC GCA ATC CGC AAC GCT GGT GCT ACG        696
Ala Thr Val Gln Glu Val Val Thr Ala Ile Arg Asn Ala Gly Ala Thr
160                 165                 170

TCG CAA TTC ATC TCT TTG CCT GGA AAT GAT TGG CAA TCT GCT GGG GCT        744
Ser Gln Phe Ile Ser Leu Pro Gly Asn Asp Trp Gln Ser Ala Gly Ala
175                 180                 185                 190

TTC ATA TCC GAT GGC AGT GCA GCC GCC CTG TCT CAA GTC ACG AAC CCG        792
Phe Ile Ser Asp Gly Ser Ala Ala Ala Leu Ser Gln Val Thr Asn Pro
                195                 200                 205

GAT GGG TCA ACA ACG AAT CTG ATT TTT GAC GTG CAC AAA TAC TTG GAC        840
Asp Gly Ser Thr Thr Asn Leu Ile Phe Asp Val His Lys Tyr Leu Asp
            210                 215                 220

TCA GAC AAC TCC GGT ACT CAC GCC GAA TGT ACT ACA AAT AAC ATT GAC        888
Ser Asp Asn Ser Gly Thr His Ala Glu Cys Thr Thr Asn Asn Ile Asp
            225                 230                 235

GGC GCC TTT TCT CCG CTT GCC ACT TGG CTC CGA CAG AAC AAT CGC CAG        936
Gly Ala Phe Ser Pro Leu Ala Thr Trp Leu Arg Gln Asn Asn Arg Gln
240                 245                 250

GCT ATC CTG ACA GAA ACC GGT GGT GGC AAC GTT CAG TCC TGC ATA CAA        984
Ala Ile Leu Thr Glu Thr Gly Gly Gly Asn Val Gln Ser Cys Ile Gln
255                 260                 265                 270

GAC ATG TGC CAG CAA ATC CAA TAT CTC AAC CAG AAC TCA GAT GTC TAT       1032
Asp Met Cys Gln Gln Ile Gln Tyr Leu Asn Gln Asn Ser Asp Val Tyr
                275                 280                 285

CTT GGC TAT GTT GGT TGG GGT GCC GGA TCA TTT GAT AGC ACG TAT GTC       1080
Leu Gly Tyr Val Gly Trp Gly Ala Gly Ser Phe Asp Ser Thr Tyr Val
            290                 295                 300

CTG ACG GAA ACA CCG ACT AGC AGT GGT AAC TCA TGG ACG GAC ACA TCC       1128
Leu Thr Glu Thr Pro Thr Ser Ser Gly Asn Ser Trp Thr Asp Thr Ser
305                 310                 315

TTG GTC AGC TCG TGT CTC GCA AGA AAG                                   1155
Leu Val Ser Ser Cys Leu Ala Arg Lys
320                 325

(2) INFORMATION FOR SEQ ID NO: 16:

(i) SEQUENCE CHARACTERISTICS:
        (A) LENGTH: 327 amino acids
        (B) TYPE: amino acid
        (D) TOPOLOGY: linear (ii) MOLECULE TYPE: protein (xi) SEQUENCE DESCRIPTION: SEQ ID NO: 16:
```

```
Gly Val Arg Phe Ala Gly Val Asn Ile Ala Gly Phe Asp Phe Gly Cys
  1               5                  10                  15
Thr Thr Asp Gly Thr Cys Val Thr Ser Lys Val Tyr Pro Pro Leu Lys
                 20                  25                  30
Asn Phe Thr Gly Ser Asn Asn Tyr Pro Asp Gly Ile Gly Gln Met Gln
             35                  40                  45
His Phe Val Asn Glu Asp Gly Met Thr Ile Phe Arg Leu Pro Val Gly
         50                  55                  60
Trp Gln Tyr Leu Val Asn Asn Leu Gly Gly Asn Leu Asp Ser Thr
 65              70                  75                  80
Ser Ile Ser Lys Tyr Asp Gln Leu Val Gln Gly Cys Leu Ser Leu Gly
                 85                  90                  95
Ala Tyr Cys Ile Val Asp Ile His Asn Tyr Ala Arg Trp Asn Gly Gly
             100                 105                 110
Ile Ile Gly Gln Gly Gly Pro Thr Asn Ala Gln Phe Thr Ser Leu Trp
         115                 120                 125
Ser Gln Leu Ala Ser Lys Tyr Ala Ser Gln Ser Arg Val Trp Phe Gly
130                 135                 140
Ile Met Asn Glu Pro His Asp Val Asn Ile Asn Thr Trp Ala Ala Thr
145                 150                 155                 160
Val Gln Glu Val Val Thr Ala Ile Arg Asn Ala Gly Ala Thr Ser Gln
                 165                 170                 175
Phe Ile Ser Leu Pro Gly Asn Asp Trp Gln Ser Ala Gly Ala Phe Ile
             180                 185                 190
Ser Asp Gly Ser Ala Ala Leu Ser Gln Val Thr Asn Pro Asp Gly
         195                 200                 205
Ser Thr Thr Asn Leu Ile Phe Asp Val His Lys Tyr Leu Asp Ser Asp
210                 215                 220
Asn Ser Gly Thr His Ala Glu Cys Thr Thr Asn Ile Asp Gly Ala
225                 230                 235                 240
Phe Ser Pro Leu Ala Thr Trp Leu Arg Gln Asn Asn Arg Gln Ala Ile
             245                 250                 255
Leu Thr Glu Thr Gly Gly Gly Asn Val Gln Ser Cys Ile Gln Asp Met
             260                 265                 270
Cys Gln Gln Ile Gln Tyr Leu Asn Gln Asn Ser Asp Val Tyr Leu Gly
         275                 280                 285
Tyr Val Gly Trp Gly Ala Gly Ser Phe Asp Ser Thr Tyr Val Leu Thr
         290                 295                 300
Glu Thr Pro Thr Ser Ser Gly Asn Ser Trp Thr Asp Thr Ser Leu Val
305                 310                 315                 320
Ser Ser Cys Leu Ala Arg Lys
                 325
```

(2) INFORMATION FOR SEQ ID NO: 17:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..72

(xi) SEQUENCE DESCRIPTION: SEQ ID NO: 17:

```
CGT GGC ACC ACC ACC ACC CGC CGC CCA GCC ACT ACC ACT GGA AGC TCT        48
Arg Gly Thr Thr Thr Thr Arg Arg Pro Ala Thr Thr Thr Gly Ser Ser
 1               5                  10                  15

CCC GGA CCT ACC CAG TCT CAC TAC                                        72
Pro Gly Pro Thr Gln Ser His Tyr
             20
```

(2) INFORMATION FOR SEQ ID NO: 18:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO: 18:

```
Arg Gly Thr Thr Thr Thr Arg Arg Pro Ala Thr Thr Thr Gly Ser Ser
 1               5                  10                  15

Pro Gly Pro Thr Gln Ser His Tyr
             20
```

(2) INFORMATION FOR SEQ ID NO: 19:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..129

(xi) SEQUENCE DESCRIPTION: SEQ ID NO: 19:

```
GGC GCT GCA AGC TCA AGC TCG TCC ACG CGC GCC GCG TCG ACG ACT TCT        48
Gly Ala Ala Ser Ser Ser Ser Ser Thr Arg Ala Ala Ser Thr Thr Ser
 1               5                  10                  15

CGA GTA TCC CCC ACA ACA TCC CGG TCG AGC TCC GCG ACG CCT CCA CCT        96
Arg Val Ser Pro Thr Thr Ser Arg Ser Ser Ser Ala Thr Pro Pro Pro
                 20                  25                  30

GGT TCT ACT ACT ACC AGA GTA CCT CCA GTC GGA                           129
Gly Ser Thr Thr Thr Arg Val Pro Pro Val Gly
             35                  40
```

(2) INFORMATION FOR SEQ ID NO: 20:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO: 20:

```
Gly Ala Ala Ser Ser Ser Ser Ser Thr Arg Ala Ala Ser Thr Thr Ser
 1               5                  10                  15

Arg Val Ser Pro Thr Thr Ser Arg Ser Ser Ser Ala Thr Pro Pro Pro
                 20                  25                  30

Gly Ser Thr Thr Thr Arg Val Pro Pro Val Gly
             35                  40
```

(2) INFORMATION FOR SEQ ID NO: 21:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..81

(xi) SEQUENCE DESCRIPTION: SEQ ID NO: 21:

```
CCC CCG CCT GCG TCC AGC ACG ACG TTT TCG ACT ACA CCG AGG AGC TCG      48
Pro Pro Pro Ala Ser Ser Thr Thr Phe Ser Thr Thr Pro Arg Ser Ser
 1               5                  10                  15

ACG ACT TCG AGC AGC CCG AGC TGC ACG CAG ACT                          81
Thr Thr Ser Ser Ser Pro Ser Cys Thr Gln Thr
             20                  25
```

(2) INFORMATION FOR SEQ ID NO: 22:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO: 22:

```
Pro Pro Pro Ala Ser Ser Thr Thr Phe Ser Thr Thr Pro Arg Ser Ser
 1               5                  10                  15

Thr Thr Ser Ser Ser Pro Ser Cys Thr Gln Thr
             20                  25
```

(2) INFORMATION FOR SEQ ID NO: 23:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..102

(xi) SEQUENCE DESCRIPTION: SEQ ID NO: 23:

```
CCG GGA GCC ACT ACT ATC ACC ACT TCG ACC CGG CCA CCA TCC GGT CCA      48
Pro Gly Ala Thr Thr Ile Thr Thr Ser Thr Arg Pro Pro Ser Gly Pro
 1               5                  10                  15

ACC ACC ACC ACC AGG GCT ACC TCA ACA AGC TCA TCA ACT CCA CCC ACG      96
Thr Thr Thr Thr Arg Ala Thr Ser Thr Ser Ser Thr Pro Pro Thr
             20                  25                  30

AGC TCT                                                             102
Ser Ser
```

(2) INFORMATION FOR SEQ ID NO: 24:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO: 24:

Pro Gly Ala Thr Thr Ile Thr Thr Ser Thr Arg Pro Pro Ser Gly Pro
 1               5                  10                  15

Thr Thr Thr Thr Arg Ala Thr Ser Thr Ser Ser Ser Thr Pro Pro Thr
             20                  25                  30

Ser Ser (2) INFORMATION FOR SEQ ID NO: 25:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..51

(xi) SEQUENCE DESCRIPTION: SEQ ID NO: 25:

ATG TAT CGG AAG TTG GCC GTC ATC TCG GCC TTC TTG GCC ACA GCT CGT     48
Met Tyr Arg Lys Leu Ala Val Ile Ser Ala Phe Leu Ala Thr Ala Arg
 1               5                  10                  15

GCT                                                                 51
Ala (2) INFORMATION FOR SEQ ID NO: 26:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO: 26:

Met Tyr Arg Lys Leu Ala Val Ile Ser Ala Phe Leu Ala Thr Ala Arg
 1               5                  10                  15

Ala (2) INFORMATION FOR SEQ ID NO: 27:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..72

(xi) SEQUENCE DESCRIPTION: SEQ ID NO: 27:

ATG ATT GTC GGC ATT CTC ACC ACG CTG GCT ACG CTG GCC ACA CTC GCA     48
Met Ile Val Gly Ile Leu Thr Thr Leu Ala Thr Leu Ala Thr Leu Ala
 1               5                  10                  15

GCT AGT GTG CCT CTA GAG GAG CGG                                     72
Ala Ser Val Pro Leu Glu Glu Arg
             20

(2) INFORMATION FOR SEQ ID NO: 28:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO: 28:

Met Ile Val Gly Ile Leu Thr Thr Leu Ala Thr Leu Ala Thr Leu Ala
 1               5                  10                  15

Ala Ser Val Pro Leu Glu Glu Arg
            20

(2) INFORMATION FOR SEQ ID NO: 29:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..66

(xi) SEQUENCE DESCRIPTION: SEQ ID NO: 29:

ATG GCG CCC TCA GTT ACA CTG CCG TTG ACC ACG GCC ATC CTG GCC ATT    48
Met Ala Pro Ser Val Thr Leu Pro Leu Thr Thr Ala Ile Leu Ala Ile
 1               5                  10                  15

GCC CGG CTC GTC GCC GCC                                            66
Ala Arg Leu Val Ala Ala
            20

(2) INFORMATION FOR SEQ ID NO: 30:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO: 30:

Met Ala Pro Ser Val Thr Leu Pro Leu Thr Thr Ala Ile Leu Ala Ile
 1               5                  10                  15

Ala Arg Leu Val Ala Ala
            20

(2) INFORMATION FOR SEQ ID NO: 31:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..63

(xi) SEQUENCE DESCRIPTION: SEQ ID NO: 31:

ATG AAC AAG TCC GTG GCT CCA TTG CTG CTT GCA GCG TCC ATA CTA TAT    48
Met Asn Lys Ser Val Ala Pro Leu Leu Leu Ala Ala Ser Ile Leu Tyr
 1               5                  10                  15

```
GGC GGC GCC GTC GCA                                              63
Gly Gly Ala Val Ala
            20

(2) INFORMATION FOR SEQ ID NO: 32:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO: 32:

Met Asn Lys Ser Val Ala Pro Leu Leu Leu Ala Ala Ser Ile Leu Tyr
  1               5                  10                  15

Gly Gly Ala Val Ala
            20

(2) INFORMATION FOR SEQ ID NO: 33:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

AAACCAGCTG TGACCAGTGG GCAACCTTCA CTGGCAACGG CTACACAGTC AGCAACAACC    60

TTTGGGGAGC ATCAGCCGGC TCTGGATTTG GCTGCGTGAC GGCGGTATCG CTCAGCGGCG   120

GGGCCTCCTG GCACGCAGAC TGGCAGTGGT CCGGCGGCCA GAACAACGTC AAGTCGTACC   180

AGAACTCTCA GATTGCCATT CCCCAGAAGA GGACCGTCAA CAGCATCAGC AGCATGCCCA   240

CCACTGCCAG CTGGAGCTAC AGCGGGAGCA ACATCCGCGC TAATGTTGCG TATGACTTGT   300

TCACCGCAGC CAACCCGAAT CATGTCACGT ACTCGGGAGA CTACGAACTC ATGATCTGGT   360

AAGCCATAAG AAGTGACCCT CCTTGATAGT TTCGACTAAC AACATGTCTT GAGGCTTGGC   420

AAATACGGCG ATATTGGGCC GATTGGGTCC TCACAGGGAA CAGTCAACGT CGGTGGCCAG   480

AGCTGGACGC TCTACTATGG CTACAACGGA GCCATGCAAG TCTATTCCTT TGTGGCCCAG   540

ACCAACACTA CCAACTACAG CGGAGATGTC AAGAACTTCT TCAATTATCT CCGAGACAAT   600

AAAGGATACA ACGCTGCAGG CCAATATGTT CTTAGTAAGT CACCCTCACT GTGACTGGGC   660

TGAGTTTGTT GCAACGTTTG CTAACAAAAC CTTCGTATAG GCTACCAATT TGGTACCGAG   720

CCCTTCACGG GCAGTGGAAC TCTGAACGTC GCATCCTGGA CCGCATCTAT CAACTAA     777

(2) INFORMATION FOR SEQ ID NO: 34:

(i) SEQUENCE CHARACTERISTICS:
        (A) LENGTH: 218 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 34:

Gln Thr Ser Cys Asp Gln Trp Ala Thr Phe Thr Gly Asn Gly Tyr Thr
  1               5                  10                  15

Val Ser Asn Asn Leu Trp Gly Ala Ser Ala Gly Ser Gly Phe Gly Cys
```

```
            20                  25                  30
Val Thr Ala Val Ser Leu Ser Gly Gly Ala Ser Trp His Ala Asp Trp
            35                  40                  45

Gln Trp Ser Gly Gly Gln Asn Asn Val Lys Ser Tyr Gln Asn Ser Gln
 50                  55                  60

Ile Ala Ile Pro Gln Lys Arg Thr Val Asn Ser Ile Ser Ser Met Pro
 65                  70                  75                  80

Thr Thr Ala Ser Trp Ser Tyr Ser Gly Ser Asn Ile Arg Ala Asn Val
                 85                  90                  95

Ala Tyr Asp Leu Phe Thr Ala Ala Asn Pro Asn His Val Thr Tyr Ser
                100                 105                 110

Gly Asp Tyr Glu Leu Met Ile Trp Leu Gly Lys Tyr Gly Asp Ile Gly
                115                 120                 125

Pro Ile Gly Ser Ser Gln Gly Thr Val Asn Val Gly Gly Gln Ser Trp
            130                 135                 140

Thr Leu Tyr Tyr Gly Tyr Asn Gly Ala Met Gln Val Tyr Ser Phe Val
145                 150                 155                 160

Ala Gln Thr Asn Thr Thr Asn Tyr Ser Gly Asp Val Lys Asn Phe Phe
                165                 170                 175

Asn Tyr Leu Arg Asp Asn Lys Gly Tyr Asn Ala Ala Gly Gln Tyr Val
                180                 185                 190

Leu Ser Tyr Gln Phe Gly Thr Glu Pro Phe Thr Gly Ser Gly Thr Leu
                195                 200                 205

Asn Val Ala Ser Trp Thr Ala Ser Ile Asn
            210                 215

(2) INFORMATION FOR SEQ ID NO: 35:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

ATGAAGTTCC TTCAAGTCCT CCCTGCCCTC ATACCGGCCG CCCTGGCC                    48

(2) INFORMATION FOR SEQ ID NO: 36:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

Met Lys Phe Leu Gln Val Leu Pro Ala Leu Ile Pro Ala Ala Leu Ala
 1               5                  10                  15

(2) INFORMATION FOR SEQ ID NO: 37:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (xi) SEQUENCE DESCRIPTION: SEQ ID NO: 37:
```

```
AGCTCGTAGA GCGTTGACTT GCCTGTGGTC TGTCCAGACG GGGGACGATA GAATGCG              57

(2) INFORMATION FOR SEQ ID NO: 38:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (xi) SEQUENCE DESCRIPTION: SEQ ID NO: 38:

GTCACCTTCT CCAACATCAA GTTCGGACCC ATTGGCAGCA CCGGCTAA                        48

(2) INFORMATION FOR SEQ ID NO: 39:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO: 39:

GGGGTTTAAA CCCGCGGGGA TT                                                    22

(2) INFORMATION FOR SEQ ID NO: 40:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 40:

TGAGCCGAGG CCTCC                                                            15

(2) INFORMATION FOR SEQ ID NO: 41:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (xi) SEQUENCE DESCRIPTION: SEQ ID NO: 41:

AGCTTGAGAT CTGAAGCT                                                         18

(2) INFORMATION FOR SEQ ID NO: 42:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 42:

CTAGAGGAGC GGTCGGGAAC CGCTAC                                                26

(2) INFORMATION FOR SEQ ID NO: 43:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide
```

-continued (xi) SEQUENCE DESCRIPTION: SEQ ID NO: 43:

Leu Glu Glu Arg Ser Gly Thr Ala Thr
1               5